United States Patent
Ahlquist et al.

(10) Patent No.: US 12,319,969 B2
(45) Date of Patent: *Jun. 3, 2025

(54) DETECTING ESOPHAGEAL DISORDERS

(71) Applicants: Exact Sciences Corporation, Madison, WI (US); Mayo Foundation for Medical Education and Research, Rochester, MN (US)

(72) Inventors: David A. Ahlquist, Rochester, MN (US); William R. Taylor, Lake City, MN (US); John B. Kisiel, Rochester, MN (US); Douglas W. Mahoney, Elgin, MN (US); Tracy C. Yab, Rochester, MN (US); Graham P. Lidgard, Middleton, WI (US); Hatim T. Allawi, Middleton, WI (US)

(73) Assignees: Exact Sciences Corporation, Madison, WI (US); Mayo Foundation for Medical Education and Research, Rochester, MN (US)

( * ) Notice: Subject to any disclaimer, the term of this patent is extended or adjusted under 35 U.S.C. 154(b) by 831 days.

This patent is subject to a terminal disclaimer.

(21) Appl. No.: 17/410,383

(22) Filed: Aug. 24, 2021

(65) Prior Publication Data
US 2021/0381066 A1 Dec. 9, 2021

Related U.S. Application Data

(63) Continuation of application No. 16/570,782, filed on Sep. 13, 2019, now Pat. No. 11,104,960, which is a continuation of application No. 15/550,703, filed as application No. PCT/US2016/023782 on Mar. 23, 2016, now Pat. No. 10,435,755.

(60) Provisional application No. 62/139,243, filed on Mar. 27, 2015.

(51) Int. Cl.
| | |
|---|---|
| *C12Q 1/68* | (2018.01) |
| *C07H 21/04* | (2006.01) |
| *C12Q 1/6883* | (2018.01) |
| *C12Q 1/6886* | (2018.01) |
| *G01N 33/574* | (2006.01) |

(52) U.S. Cl.
CPC ......... *C12Q 1/6886* (2013.01); *C12Q 1/6883* (2013.01); *G01N 33/57407* (2013.01); *C12Q 2600/112* (2013.01); *C12Q 2600/154* (2013.01); *C12Q 2600/166* (2013.01); *G01N 2440/12* (2013.01); *G01N 2800/14* (2013.01)

(58) Field of Classification Search
None
See application file for complete search history.

(56) References Cited

U.S. PATENT DOCUMENTS

| | | |
|---|---|---|
| 3,683,890 A | 8/1972 | Beal et al. |
| 4,376,110 A | 3/1983 | David et al. |
| 4,437,975 A | 3/1984 | Gillespie et al. |
| 4,445,235 A | 5/1984 | Slover et al. |
| 4,486,530 A | 12/1984 | David et al. |
| 4,582,811 A | 4/1986 | Pucci et al. |
| 4,683,195 A | 7/1987 | Mullis et al. |
| 4,683,197 A | 7/1987 | Gallati |
| 4,683,202 A | 7/1987 | Mullis |
| 4,735,214 A | 4/1988 | Berman |
| 4,859,610 A | 8/1989 | Maggio |
| 4,889,818 A | 12/1989 | Gelfand et al. |
| 4,965,188 A | 10/1990 | Mullis et al. |
| 5,011,769 A | 4/1991 | Duck et al. |
| 5,124,246 A | 6/1992 | Urdea et al. |
| 5,137,806 A | 8/1992 | Lemaistre et al. |
| 5,196,167 A | 3/1993 | Guadagno et al. |
| 5,198,365 A | 3/1993 | Grow et al. |
| 5,288,609 A | 2/1994 | Engelhardt et al. |
| 5,338,671 A | 8/1994 | Scalice et al. |
| 5,352,775 A | 10/1994 | Albertsen |

(Continued)

FOREIGN PATENT DOCUMENTS

| | | |
|---|---|---|
| CA | 2902916 C | 8/2018 |
| CN | 102021233 A | 4/2011 |

(Continued)

OTHER PUBLICATIONS

Yang B., et al., "Methylation Profiling Defines an Extensive Field Defect in Histologically Normal Prostate Tissues Associated with Prostate Cancer", Neoplasia, vol. 15, No. 4, Apr. 2013, pp. 399-408.

(Continued)

*Primary Examiner* — Jeanine A Goldberg

(74) *Attorney, Agent, or Firm* — Casimir Jones, S.C.; Peter J. Schlueter

(57) ABSTRACT

Provided herein is technology for esophageal disorder screening and particularly, but not exclusively, to methods, compositions, and related uses for detecting the presence of esophageal disorders (e.g., Barrett's esophagus, Barrett's esophageal dysplasia, etc.). In addition, the technology provides methods, compositions and related uses for distinguishing between Barrett's esophagus and Barrett's esophageal dysplasia, and between Barrett's esophageal low-grade dysplasia, Barrett's esophageal high-grade dysplasia, and esophageal adenocarcinoma within samples obtained through endoscopic brushing or nonendoscopic whole esophageal brushing or swabbing using a tethered device (e.g. such as a capsule sponge, balloon, or other device).

14 Claims, 4 Drawing Sheets

Specification includes a Sequence Listing.

(56) References Cited

U.S. PATENT DOCUMENTS

| | | |
|---|---|---|
| 5,362,623 A | 11/1994 | Vogelstein |
| 5,403,711 A | 4/1995 | Walder et al. |
| 5,409,818 A | 4/1995 | Davey et al. |
| 5,475,610 A | 12/1995 | Atwood et al. |
| 5,494,810 A | 2/1996 | Barany et al. |
| 5,508,169 A | 4/1996 | Deugau et al. |
| 5,527,676 A | 6/1996 | Vogelstein |
| 5,538,871 A | 7/1996 | Nuovo et al. |
| 5,541,308 A | 7/1996 | Hogan |
| 5,602,756 A | 2/1997 | Atwood et al. |
| 5,612,473 A | 3/1997 | Wu et al. |
| 5,624,802 A | 4/1997 | Urdea et al. |
| 5,639,611 A | 6/1997 | Wallace et al. |
| 5,648,212 A | 7/1997 | Albertsen |
| 5,660,988 A | 8/1997 | Duck et al. |
| 5,670,325 A | 9/1997 | Lapidus et al. |
| 5,691,454 A | 11/1997 | Albertsen |
| 5,710,264 A | 1/1998 | Urdea et al. |
| 5,741,650 A | 4/1998 | Lapidus et al. |
| 5,773,258 A | 6/1998 | Birch et al. |
| 5,783,666 A | 7/1998 | Albertsen |
| 5,786,146 A | 7/1998 | Herman |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,891,651 A | 4/1999 | Roche |
| 5,914,230 A | 6/1999 | Liu et al. |
| 5,928,870 A | 7/1999 | Lapidus et al. |
| 5,952,178 A | 9/1999 | Lapidus et al. |
| 5,955,263 A | 9/1999 | Vogelstein |
| 5,958,692 A | 9/1999 | Cotton et al. |
| 5,965,408 A | 10/1999 | Short |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,020,137 A | 2/2000 | Lapidus et al. |
| RE36,713 E | 5/2000 | Vogelstein |
| 6,063,573 A | 5/2000 | Kayyem |
| 6,090,543 A | 7/2000 | Prudent et al. |
| 6,090,566 A | 7/2000 | Vogelstein |
| 6,110,677 A | 8/2000 | Western et al. |
| 6,110,684 A | 8/2000 | Kemper et al. |
| 6,114,124 A | 9/2000 | Albertsen |
| 6,121,001 A | 9/2000 | Western et al. |
| 6,143,529 A | 11/2000 | Lapidus et al. |
| 6,150,097 A | 11/2000 | Tyagi et al. |
| 6,183,960 B1 | 2/2001 | Lizardi |
| 6,210,884 B1 | 4/2001 | Lizardi |
| 6,221,583 B1 | 4/2001 | Kayyem et al. |
| 6,235,470 B1 | 5/2001 | Sidransky |
| 6,235,502 B1 | 5/2001 | Weissman et al. |
| 6,245,515 B1 | 6/2001 | Vogelstein |
| 6,248,229 B1 | 6/2001 | Meade |
| 6,251,594 B1 | 6/2001 | Gonzalgo et al. |
| 6,265,171 B1 | 7/2001 | Herman et al. |
| 6,329,178 B1 | 12/2001 | Patel et al. |
| 6,335,167 B1 | 1/2002 | Pinkel et al. |
| 6,395,524 B2 | 5/2002 | Loeb et al. |
| 6,406,857 B1 | 6/2002 | Shuber et al. |
| 6,410,276 B1 | 6/2002 | Burg et al. |
| 6,413,727 B1 | 7/2002 | Albertsen |
| 6,541,217 B2 | 4/2003 | Hiraoka et al. |
| 6,602,695 B2 | 8/2003 | Patel et al. |
| 6,605,451 B1 | 8/2003 | Marmaro et al. |
| 6,630,314 B2 | 10/2003 | Nair et al. |
| 6,677,312 B1 | 1/2004 | Vogelstein |
| 6,761,702 B2 | 7/2004 | Smith |
| 6,800,617 B1 | 10/2004 | Vogelstein |
| 6,872,816 B1 | 3/2005 | Hall et al. |
| RE38,916 E | 12/2005 | Vogelstein |
| 7,037,650 B2 | 5/2006 | Gonzalgo et al. |
| 7,087,414 B2 | 8/2006 | Gerdes et al. |
| 7,087,583 B2 | 8/2006 | Vogelstein |
| 7,122,364 B1 | 10/2006 | Lyamichev et al. |
| 7,195,878 B2 | 3/2007 | Cleator |
| 7,267,955 B2 | 9/2007 | Vogelstein |
| 7,288,413 B2 | 10/2007 | Goulden |
| 7,368,233 B2 | 5/2008 | Shuber et al. |
| 7,371,527 B1 | 5/2008 | Baylin et al. |
| 7,432,050 B2 | 10/2008 | Markowitz |
| 7,485,402 B2 | 2/2009 | Arai |
| 7,485,418 B2 | 2/2009 | Goggins |
| 7,485,420 B2 | 2/2009 | Markowitz |
| 7,514,219 B2 | 4/2009 | Showe et al. |
| 7,662,594 B2 | 2/2010 | Kong et al. |
| 7,695,913 B2 | 4/2010 | Cowens et al. |
| 7,794,929 B2 | 9/2010 | Baylin et al. |
| 7,960,112 B2 | 6/2011 | Budiman et al. |
| 8,067,178 B2 | 11/2011 | Baker et al. |
| 8,114,587 B2 | 2/2012 | Gite et al. |
| 8,198,024 B2 | 6/2012 | Watson et al. |
| 8,304,214 B2 | 11/2012 | Gerdes et al. |
| 8,343,738 B2 | 1/2013 | Millar et al. |
| 8,361,720 B2 | 1/2013 | Oldham-Haltom |
| RE44,596 E | 11/2013 | Stroun et al. |
| 8,673,555 B2 | 3/2014 | Taylor et al. |
| 8,715,937 B2 | 5/2014 | Zou et al. |
| 8,741,567 B2 | 6/2014 | He et al. |
| 8,808,990 B2 | 8/2014 | Lidgard et al. |
| 8,916,344 B2 | 12/2014 | Zou et al. |
| 8,969,046 B2 | 3/2015 | Van Engeland et al. |
| 8,980,107 B2 | 3/2015 | Domanico et al. |
| 8,993,341 B2 | 3/2015 | Bruinsma et al. |
| 8,999,176 B2 | 4/2015 | Ahlquist et al. |
| 9,000,146 B2 | 4/2015 | Bruinsma et al. |
| 9,096,893 B2 | 8/2015 | Allawi et al. |
| 9,115,386 B2 | 8/2015 | Rao et al. |
| 9,121,070 B2 | 9/2015 | Taylor et al. |
| 9,163,278 B2 | 10/2015 | Bruinsma et al. |
| 9,169,511 B2 | 10/2015 | Bruinsma et al. |
| 9,212,392 B2 | 12/2015 | Allawi et al. |
| 9,315,853 B2 | 4/2016 | Domanico et al. |
| 9,399,800 B2 | 7/2016 | Taylor et al. |
| 9,422,592 B2 | 8/2016 | Morris et al. |
| 9,428,746 B2 | 8/2016 | Holmberg et al. |
| 9,506,116 B2 | 11/2016 | Ahlquist et al. |
| 9,518,990 B2 | 12/2016 | Wild et al. |
| 9,546,403 B1 | 1/2017 | Warren et al. |
| 9,632,093 B2 | 4/2017 | Taylor et al. |
| 9,637,792 B2 | 5/2017 | Ahlquist et al. |
| 9,657,511 B2 | 5/2017 | Pfau et al. |
| 9,726,670 B2 | 8/2017 | Ataman-Onal et al. |
| 9,803,249 B2 | 10/2017 | Taylor et al. |
| 9,891,223 B2 | 2/2018 | Beaulieu et al. |
| 9,896,730 B2 | 2/2018 | Kan et al. |
| 9,982,310 B2 | 5/2018 | Ahlquist et al. |
| 9,994,911 B2 | 6/2018 | Ahlquist et al. |
| 10,011,878 B2 | 7/2018 | Ahlquist et al. |
| 10,030,272 B2 | 7/2018 | Ahlquist et al. |
| 10,106,854 B2 | 10/2018 | Ørntoft et al. |
| 10,167,513 B2 | 1/2019 | Ahuja et al. |
| 10,184,154 B2 | 1/2019 | Kisiel |
| 10,292,687 B2 | 5/2019 | Maguire et al. |
| 10,301,680 B2 * | 5/2019 | Ahlquist ............ C12Q 1/6886 |
| 10,327,742 B2 | 6/2019 | Fitzgerald et al. |
| 10,370,726 B2 | 8/2019 | Ahlquist et al. |
| 10,385,406 B2 | 8/2019 | Allawi et al. |
| 10,435,755 B2 | 10/2019 | Ahlquist et al. |
| 10,465,248 B2 | 11/2019 | Allawi et al. |
| 10,519,510 B2 | 12/2019 | Ahlquist et al. |
| 10,648,025 B2 | 5/2020 | Allawi et al. |
| 10,648,035 B2 | 5/2020 | Agarwal et al. |
| 10,704,081 B2 | 7/2020 | Lidgard et al. |
| 10,822,638 B2 | 11/2020 | Allawi et al. |
| 10,883,144 B2 | 1/2021 | Ahlquist |
| 10,900,090 B2 | 1/2021 | Kisiel |
| 11,078,539 B2 | 8/2021 | Ahlquist et al. |
| 11,104,960 B2 * | 8/2021 | Ahlquist ............ C12Q 1/6886 |
| 11,118,228 B2 | 9/2021 | Allawi et al. |
| 11,298,010 B2 | 4/2022 | Bansal et al. |
| 11,345,949 B2 | 5/2022 | Allawi et al. |

(56) References Cited

U.S. PATENT DOCUMENTS

| | | |
|---|---|---|
| 11,365,451 B2 * | 6/2022 | Ahlquist .............. C12Q 1/6886 |
| 11,634,781 B2 | 4/2023 | Louwagie |
| 2002/0096469 A1 | 7/2002 | Faulkner |
| 2002/0187476 A1 | 12/2002 | Koroulis et al. |
| 2003/0086869 A1 | 5/2003 | Stallings |
| 2003/0096244 A1 | 5/2003 | Rabello et al. |
| 2003/0143606 A1 | 7/2003 | Olek et al. |
| 2003/0186248 A1 | 10/2003 | Erlander et al. |
| 2003/0224040 A1 | 12/2003 | Baylin et al. |
| 2004/0019298 A1 | 1/2004 | Zhou et al. |
| 2004/0033490 A1 | 2/2004 | Laird et al. |
| 2004/0091881 A1 | 5/2004 | Olek et al. |
| 2004/0146907 A1 | 7/2004 | Smith |
| 2004/0175733 A1 | 9/2004 | Andersen et al. |
| 2004/0234960 A1 | 11/2004 | Hogan |
| 2005/0021240 A1 | 1/2005 | Berlin et al. |
| 2005/0048527 A1 | 3/2005 | Allawi et al. |
| 2005/0064401 A1 | 3/2005 | Olek et al. |
| 2005/0075543 A1 | 4/2005 | Calabrese |
| 2005/0214926 A1 | 9/2005 | Zielenski et al. |
| 2005/0239101 A1 | 10/2005 | Sukumar et al. |
| 2005/0244836 A1 | 11/2005 | Tsang et al. |
| 2006/0084054 A1 | 4/2006 | Alsobrook et al. |
| 2006/0134663 A1 | 6/2006 | Harkin et al. |
| 2006/0147955 A1 | 7/2006 | Allawi et al. |
| 2006/0171952 A1 | 8/2006 | Mather et al. |
| 2006/0188939 A1 | 8/2006 | Gao |
| 2006/0210448 A1 | 9/2006 | Wang et al. |
| 2006/0216714 A1 | 9/2006 | Kanaoka |
| 2006/0216830 A1 | 9/2006 | Kikuiri |
| 2006/0253259 A1 | 11/2006 | Fernandez |
| 2007/0015156 A1 | 1/2007 | Goggins |
| 2007/0017015 A1 | 1/2007 | Finell |
| 2007/0048748 A1 | 3/2007 | Williams et al. |
| 2007/0054295 A1 | 3/2007 | Spivack |
| 2007/0072214 A1 | 3/2007 | Garvin et al. |
| 2007/0161062 A1 | 7/2007 | Tacke et al. |
| 2007/0172823 A1 | 7/2007 | Steinberg et al. |
| 2007/0173738 A1 | 7/2007 | Stoltz |
| 2007/0202513 A1 | 8/2007 | Shuber |
| 2007/0202525 A1 | 8/2007 | Quake et al. |
| 2008/0003571 A1 | 1/2008 | McKernan et al. |
| 2008/0039413 A1 | 2/2008 | Morris et al. |
| 2008/0064029 A1 | 3/2008 | Lofton-Day et al. |
| 2008/0081333 A1 | 4/2008 | Mori et al. |
| 2008/0097238 A1 | 4/2008 | Loktionov et al. |
| 2008/0124714 A1 | 5/2008 | Shuber et al. |
| 2008/0213870 A1 | 9/2008 | Cao et al. |
| 2008/0221056 A1 | 9/2008 | Baylin et al. |
| 2008/0227208 A1 | 9/2008 | Yee et al. |
| 2008/0254447 A1 | 10/2008 | Foekens et al. |
| 2009/0004058 A1 | 1/2009 | Liang et al. |
| 2009/0077685 A1 | 3/2009 | Buehler et al. |
| 2009/0203011 A1 | 8/2009 | Liebenberg et al. |
| 2009/0208505 A1 | 8/2009 | Samuels |
| 2009/0239212 A1 | 9/2009 | Beever et al. |
| 2009/0253142 A1 | 10/2009 | Allawi et al. |
| 2009/0286237 A1 | 11/2009 | Fitzgerald et al. |
| 2010/0075334 A1 | 3/2010 | Kim et al. |
| 2010/0092953 A1 | 4/2010 | Dietrich et al. |
| 2010/0136572 A1 | 6/2010 | Ataman-Onal et al. |
| 2010/0167940 A1 | 7/2010 | Feinberg |
| 2010/0317000 A1 | 12/2010 | Zhu |
| 2011/0009277 A1 | 1/2011 | Devos et al. |
| 2011/0045999 A1 | 2/2011 | Willman et al. |
| 2011/0123990 A1 | 5/2011 | Baker et al. |
| 2011/0136687 A1 | 6/2011 | Olek et al. |
| 2011/0160446 A1 | 6/2011 | Ritt et al. |
| 2011/0183328 A1 | 7/2011 | Taylor et al. |
| 2011/0256538 A1 | 10/2011 | Su et al. |
| 2011/0287424 A1 | 11/2011 | Chen |
| 2011/0287968 A1 | 11/2011 | Weinhausel et al. |
| 2011/0318738 A1 | 12/2011 | Jones et al. |
| 2012/0009597 A1 | 1/2012 | Lao-Sirieix et al. |
| 2012/0028835 A1 | 2/2012 | Wild et al. |
| 2012/0034605 A1 | 2/2012 | Hinoda et al. |
| 2012/0053073 A1 | 3/2012 | Kassis |
| 2012/0122088 A1 | 5/2012 | Zou |
| 2012/0122106 A1 | 5/2012 | Zou |
| 2012/0164110 A1 | 6/2012 | Feinberg et al. |
| 2012/0164238 A1 | 6/2012 | Joost |
| 2012/0246748 A1 | 9/2012 | Guo et al. |
| 2012/0288867 A1 | 11/2012 | Lidgard et al. |
| 2012/0288868 A1 | 11/2012 | Bruinsma et al. |
| 2013/0012410 A1 | 1/2013 | Zou et al. |
| 2013/0022974 A1 | 1/2013 | Chinnaiyan |
| 2013/0065228 A1 | 3/2013 | Hinoue et al. |
| 2013/0109035 A1 | 5/2013 | Das et al. |
| 2013/0244235 A1 | 9/2013 | Ahlquist et al. |
| 2013/0288241 A1 | 10/2013 | Ahuja et al. |
| 2013/0288247 A1 | 10/2013 | Mori et al. |
| 2013/0296738 A1 | 11/2013 | Swain et al. |
| 2013/0316931 A1 | 11/2013 | Sigalotti et al. |
| 2014/0017233 A1 | 1/2014 | Bais et al. |
| 2014/0045915 A1 | 2/2014 | Skog et al. |
| 2014/0057262 A1 | 2/2014 | Ahlquist et al. |
| 2014/0087382 A1 | 3/2014 | Allawi et al. |
| 2014/0137274 A1 | 5/2014 | Ishikawa |
| 2014/0162894 A1 | 6/2014 | Hatchwell et al. |
| 2014/0193813 A1 | 7/2014 | Bruinsma et al. |
| 2014/0194607 A1 | 7/2014 | Bruinsma et al. |
| 2014/0194608 A1 | 7/2014 | Bruinsma et al. |
| 2014/0221242 A1 | 8/2014 | Sukumar et al. |
| 2014/0235455 A1 | 8/2014 | Lin et al. |
| 2014/0274748 A1 | 9/2014 | Ahlquist et al. |
| 2014/0274757 A1 | 9/2014 | Kirby et al. |
| 2014/0342946 A1 | 11/2014 | Kuriakose et al. |
| 2014/0358448 A1 | 12/2014 | Tai et al. |
| 2015/0126374 A1 | 5/2015 | Califano |
| 2015/0240318 A1 | 8/2015 | Van Engeland et al. |
| 2015/0259750 A1 | 9/2015 | Andavolu |
| 2015/0275314 A1 | 10/2015 | Ahlquist et al. |
| 2015/0292029 A1 | 10/2015 | Agarwal et al. |
| 2015/0301058 A1 | 10/2015 | Schettini et al. |
| 2016/0010081 A1 | 1/2016 | Allawi et al. |
| 2016/0010163 A1 | 1/2016 | Preston et al. |
| 2016/0017430 A1 | 1/2016 | Badosa |
| 2016/0040246 A1 | 2/2016 | Ahlquist et al. |
| 2016/0045189 A1 | 2/2016 | Maguire et al. |
| 2016/0078167 A1 | 3/2016 | Rosner et al. |
| 2016/0081671 A1 | 3/2016 | Lubinski et al. |
| 2016/0081672 A1 | 3/2016 | Lubinski et al. |
| 2016/0090634 A1 | 3/2016 | Kisiel et al. |
| 2016/0108476 A1 | 4/2016 | Schweiger et al. |
| 2016/0168643 A1 | 6/2016 | Ahlquist et al. |
| 2016/0194721 A1 | 7/2016 | Allawi et al. |
| 2016/0194723 A1 | 7/2016 | Louwagie |
| 2016/0251727 A1 | 9/2016 | Ahlquist et al. |
| 2016/0281175 A1 | 9/2016 | Weinhäusel et al. |
| 2016/0312299 A1 | 10/2016 | Tyler et al. |
| 2016/0333424 A1 | 11/2016 | Morris et al. |
| 2016/0355892 A1 | 12/2016 | Ahlquist et al. |
| 2017/0058356 A1 | 3/2017 | Ahlquist et al. |
| 2017/0073772 A1 | 3/2017 | Ahlquist et al. |
| 2017/0121704 A1 | 5/2017 | Allawi et al. |
| 2017/0121757 A1 | 5/2017 | Lidgard et al. |
| 2017/0253924 A1 | 9/2017 | Lu et al. |
| 2017/0283886 A1 | 10/2017 | Clark et al. |
| 2017/0292163 A1 | 10/2017 | Salhia |
| 2017/0298439 A1 | 10/2017 | Ahlquist et al. |
| 2017/0321286 A1 | 11/2017 | Allawi et al. |
| 2017/0335401 A1 | 11/2017 | Allawi et al. |
| 2018/0037958 A1 | 2/2018 | Ahlquist et al. |
| 2018/0066320 A1 | 3/2018 | Taylor et al. |
| 2018/0087113 A1 | 3/2018 | Knudsen |
| 2018/0143198 A1 | 5/2018 | Wen et al. |
| 2018/0245157 A1 | 8/2018 | Allawi et al. |
| 2018/0251859 A1 | 9/2018 | Ahlquist et al. |
| 2018/0258498 A1 | 9/2018 | Ahlquist et al. |
| 2018/0291469 A1 | 10/2018 | Ahlquist et al. |
| 2019/0085406 A1 | 3/2019 | Mortimer et al. |
| 2019/0112659 A1 | 4/2019 | Carrell et al. |
| 2019/0127808 A1 | 5/2019 | Kisiel et al. |
| 2019/0161804 A1 | 5/2019 | Ahlquist et al. |

(56) References Cited

U.S. PATENT DOCUMENTS

| | | |
|---|---|---|
| 2019/0161805 A1 | 5/2019 | Ahlquist et al. |
| 2019/0161806 A1 | 5/2019 | Ahlquist et al. |
| 2019/0177769 A1 | 6/2019 | Allawi et al. |
| 2019/0218601 A1 | 7/2019 | Allawi et al. |
| 2019/0249263 A1 | 8/2019 | Ahlquist et al. |
| 2019/0256924 A1 | 8/2019 | Vogelstein et al. |
| 2019/0323090 A1 | 10/2019 | Widschwendter et al. |
| 2019/0330702 A1 | 10/2019 | Allawi et al. |
| 2020/0071767 A1 | 3/2020 | Sepulveda et al. |
| 2020/0131588 A1 | 4/2020 | Ahlquist |
| 2020/0172982 A1 | 6/2020 | Ahlquist et al. |
| 2020/0248233 A1 | 8/2020 | Allawi et al. |
| 2020/0291458 A1 | 9/2020 | Lidgard et al. |
| 2020/0299778 A1 | 9/2020 | Ahlquist et al. |
| 2020/0370114 A1 | 11/2020 | Song et al. |
| 2021/0102263 A1 | 4/2021 | Ahlquist et al. |
| 2021/0130907 A1 | 5/2021 | Taylor et al. |
| 2021/0348239 A1 | 11/2021 | Ahlquist et al. |
| 2022/0042111 A1 | 2/2022 | Ahlquist et al. |
| 2022/0071605 A1 | 3/2022 | Eisele et al. |
| 2022/0349009 A1 | 11/2022 | Taylor et al. |
| 2023/0046033 A1 | 2/2023 | Gagrat et al. |
| 2023/0048152 A1 | 2/2023 | Louwagie |

FOREIGN PATENT DOCUMENTS

| | | |
|---|---|---|
| CN | 102292458 A | 12/2011 |
| CN | 102711628 A | 10/2012 |
| CN | 103649298 A | 3/2014 |
| CN | 104762301 A | 7/2015 |
| CN | 104781421 A | 7/2015 |
| DE | 102010043541 A1 | 6/2011 |
| DE | 102010043541 B4 | 1/2012 |
| EP | 1269918 A1 | 1/2003 |
| EP | 1366715 A1 | 12/2003 |
| EP | 2201131 A1 | 6/2010 |
| EP | 2391729 | 12/2011 |
| EP | 2481813 A1 | 8/2012 |
| EP | 2497834 A2 | 9/2012 |
| EP | 2698436 A1 | 2/2014 |
| EP | 2201131 B1 | 11/2014 |
| EP | 3301446 A1 | 4/2018 |
| FR | 2919065 A1 | 1/2009 |
| JP | 2003508106 A | 3/2003 |
| JP | 2004529630 A | 9/2004 |
| JP | 2005304497 A | 11/2005 |
| JP | 2008502890 A | 1/2008 |
| JP | 2009512850 A | 3/2009 |
| JP | 2009095262 A | 5/2009 |
| JP | 2010533853 A | 10/2010 |
| JP | 2013510615 A | 3/2013 |
| JP | 2014525268 A | 9/2014 |
| JP | 2015006163 A | 1/2015 |
| JP | 2017086043 A | 5/2017 |
| KR | 20160128136 A | 11/2016 |
| WO | WO-9006995 A1 | 6/1990 |
| WO | WO-9202258 A1 | 2/1992 |
| WO | WO-9310820 A1 | 6/1993 |
| WO | WO-9422892 A1 | 10/1994 |
| WO | WO-9424144 A2 | 10/1994 |
| WO | WO-9500669 A1 | 1/1995 |
| WO | WO-9515373 A2 | 6/1995 |
| WO | WO-9725925 A2 | 7/1997 |
| WO | WO-9746705 A1 | 12/1997 |
| WO | WO-9928498 A2 | 6/1999 |
| WO | WO 00/26401 | 5/2000 |
| WO | WO-0050640 A1 | 8/2000 |
| WO | WO-0142781 A2 | 6/2001 |
| WO | WO-0194634 A2 | 12/2001 |
| WO | WO-0200928 A2 | 1/2002 |
| WO | WO-02070755 A2 | 9/2002 |
| WO | WO-03076594 A2 | 9/2003 |
| WO | WO-03087390 A2 | 10/2003 |
| WO | WO-2004067726 A2 | 8/2004 |
| WO | WO-2004083399 A2 | 9/2004 |
| WO | WO-2004092709 A2 | 10/2004 |
| WO | WO-2005014154 A1 | 2/2005 |
| WO | WO-2005017207 A2 | 2/2005 |
| WO | WO-2005023091 A2 | 3/2005 |
| WO | WO-2005038041 A2 | 4/2005 |
| WO | WO-2005038051 A2 | 4/2005 |
| WO | WO-2005098050 A2 | 10/2005 |
| WO | WO-2005113769 A1 | 12/2005 |
| WO | WO-2005124356 A2 | 12/2005 |
| WO | WO-2006084132 A2 | 8/2006 |
| WO | WO-2006094149 A2 | 9/2006 |
| WO | WO-2006113671 A2 | 10/2006 |
| WO | WO-2006113770 A1 | 10/2006 |
| WO | WO-2006119434 A2 | 11/2006 |
| WO | WO 2007/116417 | 10/2007 |
| WO | WO-2007121489 A2 | 10/2007 |
| WO | WO-2007123761 A2 | 11/2007 |
| WO | WO-2007134779 A1 | 11/2007 |
| WO | WO-2008010975 A2 | 1/2008 |
| WO | WO-2008073303 A2 | 6/2008 |
| WO | WO 2008/084219 | 7/2008 |
| WO | WO-2008100913 A2 | 8/2008 |
| WO | WO-2008102002 A2 | 8/2008 |
| WO | WO-2009035447 A1 | 3/2009 |
| WO | WO-2009102788 A2 | 8/2009 |
| WO | WO-2009114836 A1 | 9/2009 |
| WO | WO-2010074924 A1 | 7/2010 |
| WO | WO 2010/086389 | 8/2010 |
| WO | WO 2010/089538 | 8/2010 |
| WO | WO-2011002029 A1 | 1/2011 |
| WO | WO-2011058316 A1 | 5/2011 |
| WO | WO-2011084108 A1 | 7/2011 |
| WO | WO 2011/119934 | 9/2011 |
| WO | WO 2011/133935 | 10/2011 |
| WO | WO-2011126768 A2 | 10/2011 |
| WO | WO-2012012693 A2 | 1/2012 |
| WO | WO-2012034170 A1 | 3/2012 |
| WO | WO-2012037128 A2 | 3/2012 |
| WO | WO-2011133935 A3 | 4/2012 |
| WO | WO-2012067831 A1 | 5/2012 |
| WO | WO-2012088298 A2 | 6/2012 |
| WO | WO-2012106525 A2 | 8/2012 |
| WO | WO-2012155072 A2 | 11/2012 |
| WO | WO 2012/175562 | 12/2012 |
| WO | WO-2012167145 A2 | 12/2012 |
| WO | WO-2012174256 A2 | 12/2012 |
| WO | WO-2013026104 A1 | 2/2013 |
| WO | WO-2013058868 A2 | 4/2013 |
| WO | WO-2013070950 A1 | 5/2013 |
| WO | WO-2013103889 A1 | 7/2013 |
| WO | WO-2013116375 A1 | 8/2013 |
| WO | WO-2013142545 A1 | 9/2013 |
| WO | WO 2013/171504 | 11/2013 |
| WO | WO-2014026768 A1 | 2/2014 |
| WO | WO-2014039556 A1 | 3/2014 |
| WO | WO-2014046200 A1 | 3/2014 |
| WO | WO-2014062218 A1 | 4/2014 |
| WO | WO-2014082067 A1 | 5/2014 |
| WO | WO-2014089241 A2 | 6/2014 |
| WO | WO-2014133089 A1 | 9/2014 |
| WO | WO-2014159650 A2 | 10/2014 |
| WO | WO-2014159652 A2 | 10/2014 |
| WO | WO-2014160117 A1 | 10/2014 |
| WO | WO-2015066695 A1 | 5/2015 |
| WO | WO-2015095689 A1 | 6/2015 |
| WO | WO-2015116837 A1 | 8/2015 |
| WO | WO-2015153283 A1 | 10/2015 |
| WO | WO-2015153284 A1 | 10/2015 |
| WO | WO-2016094813 A1 | 6/2016 |
| WO | WO-2016094839 A2 * | 6/2016 ........... C12Q 1/6886 |
| WO | WO-2016097120 A1 | 6/2016 |
| WO | WO-2016109782 A1 | 7/2016 |
| WO | WO-2016160454 A1 | 10/2016 |
| WO | WO-2017040627 A1 | 3/2017 |
| WO | WO-2017075061 A1 | 5/2017 |
| WO | WO-2017129716 A1 | 8/2017 |
| WO | WO-2017176630 A1 | 10/2017 |
| WO | WO-2017180886 A1 | 10/2017 |
| WO | WO-2017191274 A2 | 11/2017 |

(56) References Cited

FOREIGN PATENT DOCUMENTS

| | | |
|---|---|---|
| WO | WO-2017192221 A1 | 11/2017 |
| WO | WO-2017210372 A1 | 12/2017 |
| WO | WO-2017223216 A1 | 12/2017 |
| WO | WO-2018017740 A1 | 1/2018 |
| WO | WO-2018045322 A1 | 3/2018 |
| WO | WO-2018140781 A1 | 8/2018 |
| WO | WO-2018160576 A1 | 9/2018 |
| WO | WO-2019010429 A1 | 1/2019 |
| WO | WO-2019035100 A2 | 2/2019 |
| WO | WO-2019067092 A1 | 4/2019 |
| WO | WO-2019108626 A1 | 6/2019 |
| WO | WO-2019144057 A1 | 7/2019 |
| WO | WO-2019195268 A2 | 10/2019 |
| WO | WO-2020089691 A1 | 5/2020 |
| WO | WO-2020112869 A1 | 6/2020 |
| WO | WO-2020118274 A1 | 6/2020 |
| WO | WO-2020154665 A1 | 7/2020 |
| WO | WO-2020206256 A1 | 10/2020 |
| WO | WO-2020236939 A2 | 11/2020 |
| WO | WO-2020254405 A1 | 12/2020 |
| WO | WO-2021041726 A1 | 3/2021 |
| WO | WO-2021055508 A1 | 3/2021 |
| WO | WO-2021076969 A1 | 4/2021 |
| WO | WO-2021087275 A1 | 5/2021 |
| WO | WO-2021212031 A1 | 10/2021 |
| WO | WO-2021226071 A2 | 11/2021 |
| WO | WO-2021226074 A2 | 11/2021 |
| WO | WO-2022039904 A2 | 2/2022 |
| WO | WO-2022040306 A1 | 2/2022 |
| WO | WO-2022165247 A1 | 8/2022 |
| WO | WO-2022187227 A1 | 9/2022 |
| WO | WO-2022187695 A1 | 9/2022 |
| WO | WO-2023081796 A1 | 5/2023 |

OTHER PUBLICATIONS

Yegnasubramanian S., et al., "Chromosome-wide Mapping of Dna Methylation Patterns in Normal and Malignant Prostate Cells Reveals Pervasive Methylation of Gene-associated and Conserved Intergenic Sequences", BMC Genornics, 2011, vol. 12, No. 313, 19 Pages.

Abbaszadegan, "Stool-based DNA testing, a new noninvasive method for colorectal cancer screening, the first report from Iran," World Journal of gastroenterology: WJG, vol. 13, p. 1528-1533, 2007.

Ahlquist D et al. (2010) "Next Generation Stool DNA Testing for Detection of Colorectal Neoplasia—Early Marker Evaluation", presented at *Colorectal Cancer: Biology to Therapy*, American Association for Cancer Research, 1 page.

Ahlquist D.A. et al., "Novel use of hypermethylated DNA markers in stool for detection of colorectal cancer: a feasibility study." Gastroenterology, 2002;122(Suppl):A40.

Ahlquist D.A., et al., "Colorectal cancer screening by detection of altered human DNA in stool: feasibility of a multitarget assay panel." Gastroenterology, 2000, 119(5):1219-27.

Ahlquist et al., "Next-generation stool DNA test accurately detects colorectal cancer and large adenomas." Gastroenterology (2012), 142, pp. 248-256.

Ahlquist et al., 1984, "HemoQuant, a new quantitative assay for fecal hemoglobin. Comparison with Hemoccult." Ann Intern Med, 101: 297-302.

Ahlquist et al., 1985, "Fecal blood levels in health and disease. A study using HemoQuant." N Engl J Med, 312: 1422-8.

Ahlquist et al., 1989, "Patterns of occult bleeding in asymptomatic colorectal cancer." Cancer, 63: 1826-30.

Ahlquist et al., 1993, "Accuracy of fecal occult blood screening for colorectal neoplasia. A prospective study using Hemoccult and HemoQuant tests." JAMA, 269: 1262-7.

Ahlquist et al., 2000, "Colorectal cancer screening by detection of altered human DNA in stool: feasibility of a multitarget assay panel." Gastroenterology, 119: 1219-27.

Ahlquist et al., 2008, "Stool DNA and occult blood testing for screen detection of colorectal neoplasia." Ann Intern Med, 149: 441-501.

Allison et al., 2007, "Screening for colorectal neoplasms with new fecal occult blood tests: update on performance characteristics." J Natl Cancer Inst, 99: 1462-70.

Anderson et al. Am. J. of Gastroenterology, Abstracts S1033, Oct. 2015.

Asai et al. "IKZF1 deletion is associated with a poor outcome in pediatric B-cell precursor acute lymphoblastic leukemia in Japan." Cancer Med. 2013; 2:412-9.

Aust De, "Mutations of the BRAF gene in ulcerative colitis-related colorectal carcinoma." Int. J. Cancer (2005), 115, pp. 673-677.

Azuara et al. "Novel Methylation Panel for the Early Detection of Colorectal Tumors in Stool DNA." Clinical Colorectal Cancer, vol. 9, No. 3, pp. 168-176, Jul. 2010.

Baxter, Eva "Investigating the association between BRAFv600E and methylation in sporadic colon cancer" PhD The University of Edinburgh, 2011.

Belinsky S.A., et al., "Promoter Hypermethylation of Multiple Genes in Sputum Precedes Lung Cancer Incidence in a High-Risk Cohort." Cancer Res, 2006;66:3338-44.

Bell et al., "c-Ki-ras gene mutations in dysplasia and carcinomas complicating ulcerative colitis." Br J Cancer (1991), 64, pp. 174-178.

Biankin et al. (2003) "Molecular pathogenesis of precursor lesions of pancreatic ductal adenocarcinoma" Pathology 35:14-24.

Brune, et al. (2008). "Genetic and epigenetic alterations of familial pancreatic cancers." Cancer Epidemiol Biomarkers Prev. 17 (12): 3536-3542.

Buck et al. "Design Strategies and Performance of Custom DNA Sequencing Primers" Biotechniques, 1999, 27(3): 528-536.

Cairns et al., "Guidelines for colorectal cancer screening and surveillance in moderate and high risk groups." Gut (2010); 59, pp. 666-689.

Cameron et al (1995) "Adenocarcinoma of the esophagogastric junction and Barrett's esophagus" Gastroenterology 109: 1541-1546.

Cameron et al. Blood, vol. 94, No. 7, pp. 2445-2451, Oct. 1999.

Camoes et al. "Potential downstream target genes of aberrant ETS transcription factors are differentially affected in Ewing's sarcoma and prostate carcinoma." PLoS ONE. 2012;7:e49819.

Campbell et al. "Aberrant expression of the neuronal transcription factor FOXP2 in neoplastic plasma cells." British journal of haematology. 2010; 149:221-30.

Chen "Expression and promoter methylation analysis of ATP-binding cassette genes in pancreatic cancer" Oncology Reports, 2012, 27:265-269.

Chen W.D., et al., "Detection in Fecal DNA of Colon Cancer-Specific Methylation of the Nonexpressed Vimentin Gene." J Natl Cancer Inst 2005;97:1124-32.

Crespi et al. "Colorectal cancer: a spreading but preventable disease" European Journal of Oncology. vol. 13(1). Mar. 2008. pp. 21-32.

De Kok, 2003, "Quantification and integrity analysis of DNA in the stool of colorectal cancer patients may represent a complex alternative to fecal occult blood testing." Clin Chem, 49: 2112-3.

Dulak, Austin M. et al. "Exome and whole-genome sequencing of esophageal adenocarcinoma identifies recurrent driver events and mutational complexity" Nature Genetics, vol. 45, No. 5, Mar. 24, 2013, 23 pages.

Eads, et al. (1999). "CpG island hypermethylation in human colorectal tumors is not associated with DNA methyltransferase overexpression." Cancer Res. 59: 2302-2306.

Ebert M.P., et al., "Aristaless-like homeobox-4 gene methylation is a potential marker for colorectal adenocarcinomas." Gastroenterology 2006;131:1418-30.

Edge, S.; Fritz, A.G.; Greene, F.L.; Trotti, A. (Eds.), AJCC Cancer Staging Manual. 7th ed: Springer, New York; 2010; Book—only table of contents provided.

EP Search Report, EP Patent Application No. 16773766.7, dated Jan. 22, 2019, 4 pages.

Esteller et al. "Inactivation of Glutathione S-Transferase P1 Gene by Promoter Hypermethylation in Human Neoplasia" Cancer Resarch, vol. 58, pp. 4515-4518, Oct. 1998.

(56) References Cited

OTHER PUBLICATIONS

Feng "Conservation and divergence of methylation patterning in plants and animals" PNAS 2010 vol. 107, No. 19, pp. 8689-8694.
Garrity-Park et al. "Methylation status of genes in non-neoplastic mucosa from patients with ulcerative colitis-associated colorectal cancer." Am J Gastroenterol (2010), 105, pp. 1610-9.
Glockner, et al. (2009). "Methylation of TFPI2 in stool DNA: a potential novel biomarker for the detection of colorectal cancer." Cancer Res. 69: 4691-4699.
Goggins, M. "Molecular markers of early pancreatic cancer." J Clin Oncol 2005; 23:4524.
Gonzalgo, et al. (1997) "Identification and characterization of differentially methylated regions of genomic DNA by methylation-sensitive arbitrarily primed PCR." Cancer Res. 57: 594-599.
Gonzalgo, et al. (1997). "Rapid quantitation of methylation differences at specific sites using methylation-sensitive single nucleotide primer extension (Ms-SNuPE)." Nucleic Acids Res. 25 (12): 2529-2531.
Grady W.M., et al., "Detection of Aberrantly Methylated hMLH1 Promoter DNA in the Serum of Patients with Microsatellite Unstable Colon Cancer 1." Cancer Res, 2001;61:900-2.
Grutzmann, et al. (2008), "Sensitive detection of colorectal cancer in peripheral blood by septin—DNA methylation assay," PLoS ONE 3(11): e3759 which is 8 pages long.
Gu et al. "Genome-scale DNA methylation mapping of clinical samples at single-nucleotide resolution." Nat Methods. 2010; 7:133-6.
Gu, et al. (2011). "Preparation of reduced representation bisulfite sequencing libraries for genome-scale DNA methylation profiling." Nature Protocols. 6 (4): 468-481.
Gurung et al. "Menin epigenetically represses Hedgehog signaling in MEN1 tumor syndrome." Cancer research. 2013;73:2650-8.
Guzinska-Ustymowicz et al., (2009), "Correlation between proliferation makers: PCNA, Ki-67, MCM-2 and antiapoptopic protein Bcl2 in colorectal cancer," Anticancer Research. 29:3049-3052.
Haag S, et al., "Regression of Barrett's esophagus: the role of acid suppression, surgery, and ablative methods." Gastrointest Endosc. Aug. 1999;50(2):229-40.
Hardcastle et al., 1996, "Randomised controlled trial of faecal-occult-blood screening for colorectal cancer." Lancet, 348: 1472-7.
Harewood et al., 2000, "Fecal occult blood testing for iron deficiency: a reappraisal." Dig Dis, 18(2): 75-82.
Harewood et al., 2002, "Detection of occult upper gastrointestinal tract bleeding: performance differences in fecal occult blood tests." Mayo Clin Proc, 77: 23-28.
Heresbach et al., 2006, "Review in depth and meta-analysis of controlled trials on colorectal cancer screening by faecal occult blood test." Eur J Gastroenterol Hepatol, 18: 427-33.
Herman, et al. (1996). "Methylation-specific PCR: A novel PCR assay for methylation status of CpG islands." Proc. Natl. Acad. Sci. USA. 93: 9821-9826.
Hibi et al. (2010) "Methylation of the TFPI2 gene is frequently detected in advanced gastric carcinoma" *Anticancer Res* 30: 4131-3.
Hibi, et al. (2010). "Methylation of TFPI2 gene is frequently detected in advanced well-differentiated colorectal cancer." Anticancer Res. 30: 1205-1207.
Hirota et al., "pS2 expression as a possible diagnostic marker of colorectal carcinoma in ulcerative colitis." Oncol Rep (2000), 7, pp. 233-239.
Hoang et al., 1997, "BAT-26, an indicator of the replication error phenotype in colorectal cancers and cell lines." Cancer Res, 57: 300-3.
Holzmann et al., "Comparative analysis of histology, DNA content, p53 and Ki-ras mutations in colectomy specimens with long-standing ulcerative colitis." Int J Cancer (1998) 76, pp. 1-6.
Hong, et al. (2008). "Multiple genes are hypermethylated in intraductal papillary mucinous neoplasms of the pancreas." Mod Pathol. 21 912): 1499-1507.
Hoque M.O., et al., "Quantitative methylation-specific polymerase chain reaction gene patterns in urine sediment distinguish prostate cancer patients from control subjects." J Clin Oncol, 2005;23:6569-75.
Howe, et al., "Annual report to the nation on the status of cancer, 1975-2003, featuring cancer among U.S. Hispanic/Latino populations." Cancer (2006) 107, pp. 1711-1742.
Imperiale et al. "Multitarget Stool DNA Testing for Colorectal-Cancer Screening" New England Journal of Medicine, vol. 370, No. 14, Apr. 3, 2014, pp. 1287-1297.
Imperiale et al., 2004, "Fecal DNA versus fecal occult blood for colorectal-cancer screening in an average-risk population." N Engl J Med, 351: 2704-14.
International Search Report and Written Opinion mailed Dec. 28, 2011 from International Patent Application No. PCT/US2011/029959, international filing date Mar. 25, 2011.
International Search Report and Written Opinion, Int'l Patent Application No. PCT/US2015/022749, mailed Aug. 19, 2015, 12 pages.
International Search Report and Written Opinion, Int'l Patent Application No. PCT/US2015/022751, mailed Aug. 26, 2015, 25 pages.
International Search Report mailed Jun. 10, 2013 from related International Patent Application No. PCT/US2013/027227.
International Search Report, International Application No. PCT/US2016/023782, mailed Sep. 1, 2016.
Issa et al., "Accelerated Age-related CpG Island Methylation in Ulcerative Colitis." Cancer Res (2001), 61, pp. 3573-3577.
Itzkowitz et al. "Diagnosis and management of dysplasia in patients with inflammatory bowel diseases." Gastroenterology (2004) 126, pp. 1634-1648.
Itzkowitz S.H., et al., "Improved fecal DNA test for colorectal cancer screening." Clin Gastroenterol Hepatol 2007;5:111-7.
Jacobs et al. "Dysregulated methylation at imprinted genes in prostate tumor tissue detected by methylation microarray." BMC Urol. 2013;13:37.
Jemal et al., 2007, "Cancer statistics, 2007." CA Cancer J Clin, 57: 43-66.
Jess et al., "Risk of intestinal cancer in inflammatory bowel disease: a population-based study from olmsted county, Minnesota." Gastroenterology (2006) 130, pp. 1039-1046.
Jiao et al. "Somatic mutations in the Notch, NF-KB, PIK3CA, and Hedgehog pathways in human breast cancers." Genes, chromosomes & cancer. 2012; 51:480-9.
Jin et al. "A multicenter, Double-blinded Validation study of methylation biomarkers for progression prediction in Barrett's Esophagus" Cancer Research, May 15, 2009, vol. 69, pp. 4112-4115.
Kaiser. (2008). "Cancer genetics. A detailed genetic portrait of the deadliest human cancers." Science. 321: 1280-1281.
Kann L., et al., "Improved marker combination for detection of de novo genetic variation and aberrant DNA in colorectal neoplasia." Clin Chem 2006;52:2299-302.
Kariya et al., 1987, "Revision of consensus sequence of human Alu repeats—a review." Gene, 53: 1-10.
Kawai, et al. (1994). "Comparison of DNA methylation patterns among mouse cell lines by restriction landmark genomic screening." Mol. Cell Biol. 14 (11): 7421-7427.
Kaz et al. "DNA methylation profiling in Barrett's esophagus and esophageal adenocarcinoma reveals unique methylation signatures and molecular subclasses" Epigenetics, Dec. 1, 2011, vol. 6, pp. 1403-1412.
Kim, H., et al., "Noninvasive molecular biomarkers for the detection of colorectal cancer," BMB Reports, 2008, vol. 41, No. 10, pp. 685-692.
Kisiel et al. "New DNA Methylation Markers for Pancreatic Cancer: Discovery, Tissue Validation, and Pilot Testing in Pancreatic Juice" Clinical Cancer Research, vol. 21, No. 19, May 28, 2015, pp. 4473-4481.
Kisiel et al. "Stool DNA testing for the detection of pancreatic cancer: assessment of methylation marker candidates." Cancer. 2012; 118:2623-31.
Kisiel et al. (AGA Abstracts, VS-68, vol. 138, No. 5, May 2010).
Kisiel, et al. (2011). "Stool DNA screening for colorectal cancer: opportunities to improve value with next generation tests." J Clin Gastroenterol. 45 (4): 301-8.

(56) References Cited

OTHER PUBLICATIONS

Kober et al. "Methyl-CpG binding column-based identification of nine genes hypermethylated in colorectal cancer." Molecular carcinogenesis. 2011; 50:846-56.
Kraus, et al., "Inflammation and colorectal cancer," Current Opinion in Pharmacology, vol. 9, No. 4, pp. 405-410 (2009).
Kronborg et al., 1996, "Randomised study of screening for colorectal cancer with faecal-occult-blood test." Lancet, 348: 1467-71.
Kronborg et al., 2004, "Randomized study of biennial screening with a faecal occult blood test: results after nine screening rounds." Scand J Gastroenterol, 39: 846-51.
Kuppuswamy et al. "Single nucleotide primer extension to detect genetic diseases: Experimental application to hemophilia B (factor IX) and cystic fibrosis genes" (1991) Proc. Natl. Acad. Sci. USA 88: 1143-1147.
Laird. (2010). "Principles and challenges of genome-wide DNA methylation analysis." Nat Rev Genet. 11: 191-203.
Lashner Ba, "Evaluation of the Usefulness of Testing for p53 Mutations in Colorectal Cancer Surveillance for Ulcerative Colitis" Am J Gastroenterol (1999), 94, pp. 456-462.
Lee et al. "Pituitary homeobox 2 (PITX2) protects renal cancer cell lines against doxorubicin toxicity by transcriptional activation of the multidrug transporter ABCB1." International journal of cancer Journal international du cancer. 2013; 133:556-67.
Leung W.K., et al., "Detection of epigenetic changes in fecal DNA as a molecular screening test for colorectal cancer: A feasibility study." Clin Chem 2004; 50(11):2179-82.
Levin B, "Screening and Surveillance for Early Detection of Colorectal Cancer . . . " Gastroenterology (2008); 134, pp. 1570-1595.
Levin et al., 2008, "Screening and surveillance for the early detection of colorectal cancer and adenomatous polyps, 2008: a joint guideline from the American Cancer Society, the US Multi-Society Task Force on Colorectal Cancer, and the American College of Radiology." CA Cancer J Clin, 58: 130-60.
Li et al. "Association between Galphai2 and ELMO1/Dock180 connects chemokine signalling with Rac activation and metastasis." Nat Commun. 2013; 4:1706.
Lim, et al. (2010). "Cervical dysplasia: assessing methylation status (Methylight) of CCNA1, DAPK1, HS3ST2, PAX1 and TFPI2 (to improve diagnostic accuracy." Gynecol Oncol. 119: 225-231.
Lin, et al., Identification of disease-associated DNA methylation in intestinal tissues from patients with inflammatory bowel disease, Clinical Genetics, vol. 80, No. 1, pp. 59-67 (2011).
Liu et al. "Medulloblastoma expresses CD1d and can be targeted for immunotherapy with NKT cells." Clin Immunol. 2013;149:55-64.
Lokk et al. "Methylation Markers of Early-Stage Non-Small Cell Lung Cancer" PLOS ONE, vol. 7, No. 6, e398013, Jun. 2012.
Ma, et al. (2011). "MicroRNA-616 induces androgen-independent growth of prostate cancer cells by suppressing expression of tissue factor pathway inhibitor TFPI-2." Cancer Res. 71: 583-592.
Maeda, et al., "DNA hypermethylation in colorectal neoplasms and inflammatory bowel disease: a mini review," Inflammapharmacology, vol. 14, No. 5-6, pp. 204-206 (2006).
Mandel et al., 1993, "Reducing mortality from colorectal cancer by screening for fecal occult blood. Minnesota Colon Cancer Control Study." N Engl J Med, 328: 1365-71.
Matsubayashi, et al. (2006). "DNA methylation alterations in the pancreatic juice of patients with suspected pancreatic disease." Cancer Res. 66: 1208-1217.
Meissner et al. (2008). "Genome-scale DNA methylation maps of pluripotent and differentiated cells." Nature. 454: 766-70.
Meissner, 2006, "Patterns of colorectal cancer screening uptake among men and women in the United States." Cancer Epidemiol Biomarkers Prev, 15: 389-94.
Melle, et al. (2005), "Discovery and identification of a-defensins as low abundant, tumor-derived serum markers in colorectal cancer," 129(1): 66-73 abstract only.
Melotte et al., "N-Myc Downstream-Regulated Gene 4 (NDRG4): A Candidate Tumor Suppressor Gene and Potential Biomarker for Colorectal Cancer" (JNCL, vol. 101, No. 13, pp. 916-927, Jul. 2009).
Meuwis, "Contribution of proteomics to colorectal cancer diagnosis," Acta Endoscopica, vol. 37, p. 295-303, including translation, 2007.
Muller et al., 2004, "Methylation changes in faecal DNA: a marker for colorectal cancer screening?" Lancet, 363: 1283-5.
Naumov "Genome-scale analysis of DNA methylation in colorectal cancer using Infinium HumanMethylation450 BeadChips" Epigenetics, 2013, vol. 8, issue 9, pp. 921-934.
Nosho, et al. (2008): "PIK3CA mutation in colorectal cancer: Relationship with genetic and epigenetic alterations," Neoplasia. 10(6) 034-541, abstract only.
Obusez et al. "Adenocarcinoma in the ileal pouch: early detection and potential role of fecal DNA methylated markers in surveillance" (Int. J. Colorectal Dis. vol. 26, pp. 951-953, 2011).
Obusez et al. "Fecal methylated markers for the detection of adenocarcinoma in ileal pouches of patients with underlying ulcerative colitis" (Inflammatory Bowel Diseases: vol. 14, Issue pS42, Dec. 2008, P-0106).
Odze Rd, "Genetic Alterations in Chronic Ulcerative Colitis-Associated Adenoma-Like DALMs Are Similar to Non-Colitic Sporadic Adenomas" Am J Surg Pathol (2000), 24, pp. 1209-1216.
Olaru, et al., "Unique patterns of CpG island methylation in inflammatory bowel disease-associated colorectal cancers," Inflammatory Bowel Diseases, vol. 18, No. 4, pp. 641-648 (Epub Aug. 9, 2011).
Olson et al., 2005, "DNA stabilization is critical for maximizing performance of fecal DNA-based colorectal cancer tests." Diagn Mol Pathol, 14: 183-91.
Omura, et al. (2008). "Genome-wide profiling of methylated promoters in pancreatic adenocarcinoma." Cancer Biol Ther. 7 (7): 1146-1156.
Omura, et al. (2009). "Epigenetics and epigenetic alterations in pancreatic cancer." Int. J. Clin Exp Pathol. 2: 310-326.
Osborn et al., 2005, "Stool screening for colorectal cancer: molecular approaches." Gastroenterology, 128: 192-206.
Osborn NK, and Ahlquist DA, "Stool screening for colorectal cancer: molecular approaches." Gastroenterology 2005;128:192-206.
Osborn, et al., "Aberrant methylation of the eyes absent 4 gene in ulcerative colitis-associated dysplasia," Clinical Gastroenterology and Hepatology, vol. 4, No. 2, pp. 212-218 (2006).
Oster, B. et al., "Identification and validation of highly frequent CpG island hypermethylation in colorectal adenomas and carcinomas." Int J Cancer. 2011;129(12):2855-66.
Pao et al. "The endothelin receptor B (EDNRB) promoter displays heterogeneous, site specific methylation patterns in normal and tumor cells" Human Molecular Genetics, vol. 10, No. 9, pp. 903-910.
Park, et al. (2002), "Expressiono f melanoma antigen-encoding genes (MAGE) by common primers for MAGE-A1 to -A6 in colorectal carcinomas among Koreans," J. Korean Med. Sci 17: 497-501.
Person et al. "Chronic cadmium exposure in vitro induces cancer cell characteristics in human lung cells." Toxicol Appl Pharmacol. 2013; 273(2):281-8.
Petko Z., et al., "Aberrantly Methylated CDKN2A, MGMT, and MLH1 in Colon Polyps and in Fecal DNA from Patients with Colorectal Polyps." Clin Cancer Res 2005;11:1203-9.
Raimondo et al. "Methylated DNA Markers in Pancreatic Juice Discriminate Pancreatic Cancer From Chronic Pancreatitis and Normal Controls" Gastroenterology 2013; 144:S-90.
Raimondo, M. et al. "Sensitive DNA Marker Panel for Detection of Pancreatic Cancer by Assay in Pancreatic Juice", Gastroenterology, May 2, 2014, vol. 146, Iss. 5, Suppl. 1, p. S-132.
Rex et al. "American College of Gastroenterology guidelines for colorectal cancer screening 2008." Am J Gastroenterol (2009); 104, pp. 739-750.
Ruppenthal et al. "TWIST1 Promoter Methylation in Primary Colorectal Carcinoma" Pathol. Oncol. Res., 2011, 17:867-872.

(56) References Cited

OTHER PUBLICATIONS

Sadri and Hornsby "Rapid Analysis of DNA Methylation Using New Restriction Enzyme Sites Created by Bisulfite Modification." (1996) *Nucl. Acids Res.* 24: 5058-5059.
Saitoh et al. (1995), "Intestinal protein loss and bleeding assessed by fecal hemoglobin, transferrin, albumin, and alpha-1-antitrypsin levels in patients with colorectal diseases," Digestion. 56(1): 67-75, abstract only.
Sambrook et al., 1989, Fritsch, E.F., Maniatis, T. (ed.), Molecular Cloning, Cold Spring Harbor Lab. Press, Cold Spring Harbor, N.Y., 30 pages.
Samowitz et al., 1999, "BAT-26 and BAT-40 instability in colorectal adenomas and carcinomas and germline polymorphisms." Am J Path, 154: 1637-41.
Sato et al., "Aberrant methylation of the HPP1 gene in ulcerative colitis-associated colorectal carcinoma." Cancer Res (2002), 62, pp. 6820-6822.
Sato, et al. (2003). "Discovery of novel targets of aberrant methylation in pancreatic carcinoma using high-throughput microarrays." Cancer Res. 63: 3735-3742.
Sato, et al. (2008). "CpG island methylation profile of pancreatic intraepithelial neoplasia." Mod Pathol. 21 93): 238-244.
Schulmann, et al., Molecular phenotype of inflammatory bowel disease-associated neoplasms with microsatellite instability, Gastroenterology, vol. 129, No. 1, pp. 74-85 (2005).
Schwartz et al., 1983, "The "HemoQuant" test: a specific and quantitative determination of heme (hemoglobin) in feces and other materials." Clin Chem, 29:2061-7.
Schwartz et al., 1985, "Quantitative fecal recovery of ingested hemoglobin-heme in blood: comparisons by HemoQuant assay with ingested meat and fish." Gastroenterology, 89: 19-26.
Sen-Yo et al. "TWIST1 hypermethylation is observed in pancreatic cancer" Biomedical Reports; 1:33-33, 2013.
Seshagiri et al. "Recurrent R-spondin fusions in colon cancer." Nature. 2012; 488:660-4.
Shin et al. "Bile-based detection of extrahepatic cholangiocarcinoma with quantitative DNA methylation markers and its high sensitivity." The Journal of molecular diagnostics : JMD. 2012;14:256-63.
Singer-Sam et al. "A quantitative HpaII-PCR assay to measure methylation of DNA from a small number of cells" (1990) *Nucl. Acids Res.* 18(3): 687.
Singer-Sam et al. "A sensitive, quantitative assay for measurement of allele-specific transcripts differing by a single nucleotide." (1992) PCR Methods Appl. 1: 160-163.
Singh et al., 2006, "Risk of developing colorectal cancer following a negative colonoscopy examination: evidence for a 10-year interval between colonoscopies." JAMA, 295: 2366-73.
Stumm et al. "Strong expression of the neuronal transcription factor FOXP2 is linked to an increased risk of early PSA recurrence in ERG fusion-negative cancers." Journal of clinical pathology. 2013;66:563-8.
Summons to attend oral proceedings, European patent application No. 11760295.3, mailed Mar. 4, 2016.
Surdez et al. "Targeting the EWSR1-FLI1 oncogene-induced protein kinase PKC-beta abolishes ewing sarcoma growth." Cancer research. 2012;72:4494-503.
Szabo and Mann "Allele-specific expression and total expression levels of imprinted genes during early mouse development: implications for imprinting mechanisms." (1995) Genes Dev. 9(24): 3097-3108.
Tan et al. Carcinogenesis. 2002 23(2): 231-236.
Tang, et al. (2010). "Prognostic significance of tissue factor pathway inhibitor 2 in pancreatic carcinoma and its effect on tumor invasion and metastatis." Med Oncol. 27: 867-875.
Taylor et al. "Expression of p53 in colorectal cancer and dysplasia complicating ulcerative colitis." Br J Surg (1993), 80, pp. 442-444.
Tibble, et al. (2001), "Faecal capprotectin and faecal occult blood tests in the diagnosis of colorectal carcinoma and adenoma.," Gut. 49:402-408.

Tonack, et al. (2009). "Pancreatic cancer: proteomic approaches to a challenging disease." Pancreatology. 9: 567-576.
Toyota, et al. (1999). "Identification of differentially methylated sequences in colorectal cancer by methylated CpG island amplification." Cancer Res. 59: 2307-2312.
Tsunoda, et al. (2009). "Methylation of CLDN6, FBN2, RBP1, RBP4, TFPI2 and TMEFF2 in esophageal squamous cell carcinoma." Oncol Rep. 21: 1067-1073.
Uchida, et al. (1994), "Immunochemical detection of human lactoferrin in feces as a new marker for inflammatorygastrointestinal disorders and colon cancer," Clinical Biochemistry. 27(4)L 259-264, abstract only.
Vincent et al. "Genome-wide analysis of promoter methylation associated with gene expression profile in pancreatic adenocarcinoma." Clinical cancer research : an official journal of the American Association for Cancer Research. 2011; 17:4341-54.
Wang, "Gene expression profiles and molecular markers to predict recurrence of duke's B Colon Cancer," vol. 22, p. 1564-1571, 2004.
Watanabe, T., "RUNX3 copy number predicts the development of UC-associated colorectal cancer" International Journal of Oncology (2011), 38, pp. 201-207.
Wen, et al. (2006), "Frequence epigenetic silencing of the bome morphogenic protein 2 gene through methylation in gastric carcinomas," Onogene. 25:2666-2673.
Wheeler et al. "Hypermethylation of the promoter region of the E-cadherin gene (CDH1) in sporadic and ulcerative colitis associated colorectal cancer." Gut (2001), 48, pp. 367-371.
Winawer et al., 1993, "Screening for colorectal cancer with fecal occult blood testing and sigmoidoscopy." J Natl Cancer Inst, 85: 1311-8.
Wittekind et al. (1986), "Localization of CEA, HCG, lysozyme, alpha-1-antitrypsin, and alpha-1-antichymotrypsin in gastric cancer and prognosis," Virchows Arch 409:715-724.
Wu, "Aberrant Gene Methylation in the Neoplastic Progression of Barrett's Esophagus: Identification of Candidate Diagnostic Markers" Gastroenterology (2011) 14: S-222.
Xiong, et al. (1997). Nucleic Acids Res. 25 (12): 2532-2534.
Xu, et al. Genome-wide methylation analysis shows similar patterns in Barrett's esophagus and esophageal adenocarcinoma. Carcinogenesis. Dec. 2013;34(12):2750-6.
Yachida, et al. (2010). "Distant metastasis occurs late during the genetic evolution of pancreatic cancer." Nature. 467: 1114-1117.
Yamaguchi, et al. (2005). "Pancreatic juice cytology in intraductal papillary mucinous neoplasm of the pancreas." Pancreatology. 5: 416-421.
Yang N. et al. "Methylation markers for CCNA1 and C13ORF18 are strongly associated with high-grade cervical intraepithelial neoplasia and cervical cancer in cervical scrapings." Cancer epidemiology, biomarkers & prevention : a publication of the American Association for Cancer Research, cosponsored by the American Society of Preventive Oncology. 2009;18:3000-7.
Young, "Fecal Immunochemical Tests (FIT) vs. Office-based guaiac fecal occult blood test (FOBT)," Practical Gastroenterology, Colorectal Cancer, series 3, p. 46-56, 2004.
Zhai et al. "Genome-wide DNA Methylation Profiling of Cell-Free Serum DNA in Esophageal Adenocarcinoma and Barrett Esophagus" Neoplasia, Jan. 11, 2012, vol. 14, No. 1, pp. 29-33.
Zhang et al. (2009). "DNA methylation analysis of chromosome 21 gene promoters at single base pair and single allele resolution." PLoS Genet. 5 (3): e1000438.
Zhao et al. "Genome-wide identification of Epstein-Barr virus-driven promoter methylation profiles of human genes in gastric cancer cells." Cancer. 2013;119:304-12.
Zijlstra et al., 2002, "A quantitative analysis of rate-limiting steps in the metastatic cascade using human-specific real-time polymerase chain reaction." Cancer Res, 62: 7083-92.
Zou et al., 2006, "A sensitive method to quantify human long DNA in stool: relevance to colorectal cancer screening." Cancer Epidemiol Biomarkers Prev, 15: 1115-9.
Zou H.Z., et al., "Detection of aberrant p16 methylation in the serum of colorectal cancer patients." Clin Cancer Res 2002;8(1):188-91.

(56) References Cited

OTHER PUBLICATIONS

Zou, et al. (2007), "Highly methylated genes in colorectal neoplasia: Implications for screening," Cancer Epidemilogy Biomarkers Prev. 16(12): 2686-2696.
Zou, et al. (2009). "T2036 Pan-Detection of Gastrointestinal Neoplasms By Stool DNA Testing Establishment of Feasibility." *Gastroenterology*. 136: A-625.
Zou, et al., "High Detection Rates of Colorectal Neoplasia by Stool DNA Testing with a Novel Digital Melt Curve Assay," Gastroenterology, vol. 136, No. 2, Feb. 1, 2009, pp. 459-470.
Zou, et al., "T2034 Stool DNA and Occult Blood for Detection of Colorectal Cancer: Complementary Markers," Gastroenterology, vol. 136, No. 5, May 1, 2009, p A-625.
Ahlquist D.A., et al., "A Stool Collection Device: The First Step in Occult Blood Testing," Annals of Internal Medicine, 1988, vol. 108, No. 4, pp. 609-612.
Ahlquist D.A., et al., "Cologuard Primed to Change Landscape of CRC Screening," Mayo Clinic Clinical Updates, Dec. 3, 2014, pp. 1-4, [Retrieved on Jul. 6, 2016] Retrieved from URL: http://www.mayoclinic.org/medical-professionals/clinical-updates/digestivediseases/cologuard-primed-to-change-landscape-of-crc-screening.
Ahlquist D.A., et al., "Molecular Stool Screening for Colorectal Cancer. Using DNA Markers May Be Beneficial, But Large Scale Evaluation is Needed," BMJ, Jul. 29, 2000, vol. 321, pp. 254-255.
Ahmed F.E., et al., "Transcriptomic Molecular Markers for Screening Human Colon Cancer in Stool and Tissue," Cancer Genomics and Proteomics, 2007, vol. 4, pp. 1-20.
Allawi et al., Abstract 712: Detection of lung cancer by assay of novel methylated DNA markers in plasma. Proceedings: AACR Annual Meeting Apr. 1-5, 2017, Washington, DC. 3 pages.
Anderson B.W., et al., "Aberrant Methylation During Gastric Carcinogenesis: Patterns of Acquisition Using Novel Methylated DNA Markers From Whole Methylome Discovery," Gastroenterology, Apr. 1, 2016, vol. 150, No. 4, pp. S863-S864.
Anderson B.W., et al., "Su2013 Methylated DNA Markers for Detection of Sporadic Colorectal Neoplasia: Comparison Between Age Groups Younger Than and Older Than 50," Gastroenterology, Apr. 1, 2016, vol. 150, No. 4, p. S611, Doi: 10.1016/S0016-5085(16)32095-9, XP055725829, abstract.
Andersson D., et al., "Properties of Targeted Preamplification in DNA and cDNA Quantification," Expert Reviews in Molecular Diagnostics, GB, Aug. 3, 2015, vol. 15, No. 8, pp. 1085-1100, Doi:10.1586/14737159.2015.1057124, ISSN 1473-7159, XP055341095.
Antequera et al.. High levels of de novo methylation and altered chromatin structure at CpG islands in cell lines. Cell. Aug. 10, 1990;62(3):503-14.
Arneson N., et al., "Genomeplex Whole-genome Amplification," Cold Spring Harbor protocols, 2008, 7 Pages, DOI: 10.1101/pdb.prot4920.
Aronchick C.A., et al., "A Novel Tableted Purgative for Colonoscopic Preparation: Efficacy and Safety Comparisons with Colyte and Fleet Phospho-soda," Gastrointestinal endoscopy, 2000, vol. 52, No. 3, pp. 346-352 (8 Pages).
Auerkari E.I., "Methylation of Tumor Suppressor Genes P16(INK4a), p27(Kip1) and E-cadherin in Carcinogenesis," Oral Oncology, Jan. 2006, vol. 42, No. 1, pp. 5-13.
Aust D.E., et al., "Mutations of the BRAF Gene in Ulcerative Colitis-related Colorectal Carcinoma," International Journal of Cancer, 2005, vol. 115, pp. 673-677.
Ballabio et al., Screening for steroid sulfatase (STS) gene deletions by multiplex DNA amplification, Human Genetics, 1990, 84(6): 571-573.
Ballester V., et al., "Novel Methylated DNA Markers for the Detection of Colorectal Neoplasia in Lynch Syndrome," Abstract 307, Gastroenterology, 2016, vol. 150, No. 4, p. S-70.
Baranay F., "Genetic Disease Detection and DNA Amplification Using Cloned Thermostable Ligase," Proceedings of the National Academy of Sciences of the United States of America, Jan. 1991, vol. 88, pp. 189-193.
Barat A., et al., "Comparative Correlation Structure of Colon Cancer Locus Specific Methylation: Characterisation of Patient Profiles and Potential Markers Across 3 Array-Based Datasets," Journal of Cancer, Jul. 2015, vol. 6, pp. 795-811.
Bardan E., et al., "Colonoscopic Resection of Large Colonic Polyps-A Prospective Study," Israel Journal of Medical Sciences, Dec. 1997, vol. 33, No. 12, pp. 777-780 (7 Pages).
Baylin., et al., Certified Copy of U.S. Appl. No. 60/900,713, filed Feb. 12, 2007, 188 Pages.
Beeker C., et al., "Colorectal Cancer Screening in Older Men and Women: Qualitative Research Findings and Implications for Interventions," Journal of Community Health, 2000, vol. 25, No. 3, pp. 263-278.
Belshaw N.J., et al., "Use of DNA From Human Stools to Detect Aberrant Cpg Island Methylation of Genes Implicated in Colorectal Cancer," Cancer Epidemiology, Biomarkers & Prevention, Sep. 2004, vol. 13, No. 9, pp. 1495-1501.
Bennett L.B., et al., "DNA Hypermethylation Accompanied by Transcriptional Repression in Follicular Lymphoma," Genes Chromosomes Cancer, Sep. 2009, vol. 48, No. 9, pp. 828-841 (23 Pages).
Bentley D.R., et al., "Accurate Whole Human Genome Sequencing Using Reversible Terminator Chemistry," Nature, Nov. 6, 2008, vol. 456, No. 7218, pp. 53-59, 20 Pages.
Berezikov E., et al., "Approaches to MicroRNA Discovery," Nature Genetics Supplement, Jun. 2006, vol. 38, pp. S2-S7.
Berger B.M., et al., "Stool DNA Screening for Colorectal Neoplasia: Biological and Technical Basis for High Detection Rates," Pathology, Feb. 2012, vol. 44, No. 2, pp. 80-88 (10 Pages).
Bert S.A., et al., "Regional Activation of the Cancer Genome by Long-range Epigenetic Remodeling," Cancer Cell, Jan. 14, 2013, vol. 23, No. 1, pp. 9-22.
Bibikova, "GoldenGate Assay for Methylation of BeadArray(TM) Technology," Technical Note, Jan. 1, 2009, 7 Pages, [Retrieved on Aug. 29, 2016], Retrieved from URL: http://agtc.wayne.edu/pdfs/goldengate_methylation_brochure.pdf.
Bonin C.A., et al., "Identification of Differentially Methylated Regions in New Genes Associated With Knee Osteoarthritis," Gene, Jan. 15, 2016, vol. 576, pp. 312-318 (19 Pages).
Boynton K.A., et al., "DNA Integrity as a Potential Marker for Stool-based Detection of Colorectal Cancer," Clinical Chemistry, 2003, vol. 49, No. 7, pp. 1058-1065.
Breivik J., et al., "K-ras Mutation in Colorectal Cancer: Relations to Patient Age, Sex and Tumour Location," British Journal of Cancer, Feb. 1994, vol. 69, No. 2, pp. 367-371.
Bryson G.L.M., et al., "Gene Structure, Sequence, and Chromosomal Localization of the Human Red Cell-type Low-molecular-weight Acid Phosphotyrosyl Phosphatase Gene ACP1," Genomics, Nov. 20, 1995, vol. 30, No. 2, pp. 133-140.
Budd G.T., et al., "Circulating Tumor Cells Versus Imaging-Predicting Overall Survival in Metastatic Breast Cancer," Clinical Cancer Research, Nov. 1, 2006, vol. 12, No. 21, pp. 6403-6409 (8 Pages).
Bustin S A., "Absolute Quantification of Mrna Using Real-time Reverse Transcription Polymerase Chain Reaction Assays," Journal of Molecular Endocrinology, Oct. 2000, vol. 25, No. 2, pp. 163-193 (25 pages).
Calvisi D.F., et al., "Inactivation of Ras GTPase-activating Proteins Promotes Unrestrained Activity of Wild-type Ras in Human Liver Cancer," Journal of Hepatology, Feb. 2011, vol. 54, No. 2, pp. 311-319 (15 Pages).
Campan M., et al., "Genome-Scale Screen for DNA Methylation-Based Detection Markers for Ovarian Cancer," PLOS One, Dec. 7, 2011, vol. 6, No. 12(e28141), 10 Pages.
Carvolho R., et al., "Genome-wide DNA Methylation Profiling of Nonsmall Cell Lung Carcinomas. Epigenetics Chromatin," Epigenetics & Chromatin, Jun. 22, 2012, vol. 5, No. 9, pp. 1-18.
Cavestro G.M., et al., "Role of Faecal Elastase 1 in Pancreatic Cancer: A Pilot Study," Pancreas, Raven Press, New York, NY, US, Nov. 5, 2004, vol. 29, No. 4, pp. 349-350, ISSN: 0885-3177, XP008135408.
Ceska et al., Structure-specific DNA cleavage by 5' nucleases. Trends Biochem Sci. Sep. 1998;23(9):331-6.

(56) References Cited

OTHER PUBLICATIONS

Chalasani N.P., et al., "A Novel Blood-Based Panel of Methylated DNA and Protein Markers for Detection of Early-Stage Hepatocellular Carcinoma," Clinical Gastroenterology and Hepatology, Dec. 2021, vol. 19, No. 12, pp. 2597-2605.e4 (13 Pages).
Chamberlain et al., Deletion screening of the Duchenne muscular dystrophy locus via multiplex DNA amplification. Nucleic Acids Res. Dec. 1988;16(23):11141-56.
Chamberlin M., et al., "New RNA Polymerase from *Escherichia Coli* Infected withBacteriophage T7," Nature, Oct. 17, 1970, vol. 228, No. 5268, pp. 227-231.
Chapman C.J., et al., "Autoantibodies in Lung Cancer: Possibilities for Early Detection and Subsequent Cure," Thorax, Mar. 2008, vol. 63, No. 3, pp. 228-233 (7 Pages).
Chatterjee S.K., et al., "Cancer Biomarker: Knowing the Present and Predicting the Future," Future Oncology, 2005, vol. 1, No. 1, pp. 37-50.
Chen C-H., et al., "DNA Methylation Identifies Loci Distinguishing Hereditary Nonpolyposis Colorectal Cancer Without Germ-Line MLH1/MSH2 Mutation from Sporadic Colorectal Cancer," Clinical and Translational Gastroenterology, Dec. 15, 2016, vol. 7, No. 12: e208 (12 pages), XP055756351.
Chen H., et al., "Differential Regulation of the Human Gene DAB2IP in Normal and Malignant Prostatic Epithelia: Cloning and Characterization," Genomics, Apr. 2002, vol. 79, No. 4, pp. 573-581.
Chen Y., et al., "HOPX is Methylated and Exerts Tumour-suppressive Function Through Ras-induced Senescence in Human Lung Cancer," The Journal of Pathology, Feb. 2015, vol. 235, No. 3, pp. 397-407, (Oct. 24, 2014).
Cheng Y., et al., "Analysis of DNA Methylation Patterns Associated with the Gastric Cancer Genome," Oncology Letters, 2014, vol. 7, pp. 1021-1026.
Clayton S.J., et al., "K-ras Point Mutation Detection in Lung Cancer: Comparison of Two Approaches to Somatic Mutation Detection Using ARMS Allele-Specific Amplification," Clinical Chemistry, Dec. 2000, vol. 46, No. 12, pp. 1929-1938.
Cohen S.J., et al., "Relationship of Circulating Tumor Cells to Tumor Response, Progression-Free Survival, and Overall Survival in Patients with Metastatic Colorectal Cancer," Journal of Clinical Oncology, Jul. 1, 2008, vol. 26, No. 19, pp. 3213-3221, 11 Pages.
Cologuard: "Innovation Supports the Cologuard Scientific Platform," Geneoscopy Exhibit, vol. 1079, 2024, 7 Pages, Retrieved from URL: https://www.exactsciences.com/cancer-testing/cologuard-stool-test.
Communication of a Notice of Opposition and Statement for European Application No. 18176135.4, mailed Mar. 5, 2021, 16 Pages.
Conroy K., et al., "Exact Sciences Completes 40,000 Cologuard Tests During First Quarter 2016," Exact Sciences Latest News, May 3, 2016, pp. 1-10.
Co-Pending U.S. Appl. No. 61/149,581, filed Feb. 3, 2009, 59 Pages.
Costello J.F., et al., "Graded Methylation in the Promoter and Body of the 06-Methylguanine DNA Methyltransferase (MGMT) Gene Correlates with MGMT Expression in Human Glioma Cells," Journal of Biological Chemistry, Jun. 24, 1994, vol. 269, No. 25, pp. 17228-17237.
Cristofanilli M., et al., "Circulating Tumor Cells, Disease Progression, and Survival in Metastatic Breast Cancer," The New England Journal of Medicine, Aug. 19, 2004, vol. 351, No. 8, pp. 781-791.
"Curriculum Vitae of Duncan H. Whitney, Ph.D," Jan. 11, 2024, 10 Pages.
Da Riva L., et al., "Proteomic Detection of a Large Amount of SCGF(Alpha) in the Stroma of GISTs After Imatinib Therapy," Journal of Translational Medicine, Sep. 23, 2011, vol. 9, No. 158, pp. 1-13.
Dai Z., et al., "Global Methylation Profiling of Lung Cancer Identifies Novel Methylated Genes," Neoplasia, Jul.-Aug. 2001, vol. 3, No. 4, pp. 314-323.

Dammann R., et al., "The CpG Island of the Novel Tumor Suppressor Gene RASSF1A is Intensely Methylated in Primary Small Cell Lung Carcinomas," Oncogene, Jun. 14, 2001, vol. 20, No. 27, pp. 3563-3567.
Dasari A., et al., "Trends in the Incidence, Prevalence, and Survival Outcomes in Patients With Neuroendocrine Tumors in the United States," JAMA oncology, Oct. 1, 2017, vol. 3, No. 10, pp. 1335-1342.
Dassonville O., et al., "Expression of Epidermal Growth Factor Eeceptor and Survival in Upper Aerodigestive Tract Cancer," Journal of Clinical Oncology, Oct. 1993, vol. 11, No. 10, pp. 1873-1878.
Davies H., et al., "Somatic Mutations of the Protein Kinase Gene Family in Human Lung Cancer," Cancer Research, Sep. 1, 2005, vol. 65, No. 17, pp. 7591-7595.
Decision Granting Institution of Inter Partes Review for IPR2024-00459 for U.S. Pat. No. 11,634,781, dated Jul. 26, 2024, 34 Pages.
Declaration of Brendan T. Jones for U.S. Pat. No. 11,634,781, Dated Jan. 11, 2024, 11 Pages.
Declaration of Brendan T. Jones for U.S. Pat. No. 11,970,746, dated Aug. 20, 2024, 17 Pages.
Declaration of Duncan Whitney Ph.D for U.S. Pat. No. 11,970,746, dated Aug. 20, 2024, 225 Pages.
"Declaration of Duncan Whitney, Ph.D.," Exact Sciences Corporation, dated Jan. 10, 2024, 186 Pages.
"Declaration of Mr. Anthony P. Shuber, MS," Reexamination U.S. Appl. No. 90/015,237, dated May 22, 2023, 63 Pages.
Derks S., et al., "Promoter Methylation Precedes Chromosomal Alterations in Colorectal Cancer Development," Abstract, Cellular Oncology, Dec. 12, 2006, vol. 28, pp. (5-6), 2 Pages, [Retrieved on Sep. 1,2024] Retrieved from URL: https://www.ncbi.nlm.nih.gov/pmc/articles/PMC4618222/.
Derks S., et al., "Promoter Methylation Precedes Chromosomal Alterations in Colorectal Cancer Development," Cellular Oncology, 2006, vol. 28, No. 5-6, pp. 247-257.
Deuter R., et al., "A Method for Preparation of Fecal DNA Suitable for PCR," Nucleic Acids Research, Sep. 25, 1995, vol. 23, No. 18, pp. 3800-3801.
Devos T., et al., "Circulating Methylated SEPT9 DNA in Plasma is a Biomarker for Colorectal Cancer," Clinical Chemistry, Jul. 2009, vol. 55, No. 7, pp. 1337-1346 (20 Pages).
Dollinger M.M., et al., "Screening for Colorectal Cancer: A Blinded Multicenter Phase II Diagnostic Study for Validation of a DNA Based Stool Test (Genefec2)," Gastroenterology, Abstract S1134, 2008, vol. 134, No. 4, Supplement 1, A185, 1 Page.
Don R.H., et al., "'Touchdown' PCR to Circumvent Spurious Priming During Gene Amplification," Nucleic Acids Research, Jul. 25, 1991, vol. 19, No. 4, p. 4008.
Dowdy et al., Statistics for Research, John Wiley & Sons, New York, 1983. TOC only. 6 pages.
Egan J.P., "Signal Detection Theory and ROC Analysis," Academic Press, New York, 1975, 9 Pages, TOC Only.
Egeblad M., et al., "New Functions for the Matrix Metalloproteinases in Cancer Progression," Nature Reviews Cancer, Mar. 2002, vol. 2, No. 3, pp. 161-174.
Eguchi S., et al., "Mutations of the P53 Gene in Stool of Patients With Resectable Colorectal Cancer," Cancer, Apr. 15, 1996, vol. 77, No. 8, pp. 1707-1710.
Elbashir S.M., et al., "RNA Interference is Mediated by 21- and 22-nucleotide RNAs," Genes & Development, Jan. 15, 2001, vol. 15, No. 2, pp. 188-200.
Erlich H A., "PCR Technology: Principles and Applications for DNA Amplification," Stockton Press, TOC Only, 1989, 5 Pages.
Etzioni et al. "The case for early detection". Nature Reviews | Cancer (Apr. 2003) vol. 3, pp. 1-10.
European Supplemental Search Report for EP17792973.4, mailed Jan. 3, 2020, 15 pages.
Ex Parte Reexamination Certificate for U.S. Pat. No. 11,637,781, issued on Dec. 4, 2023, 2 Pages.
Exact Sciences: "Cologuard Patient Guide," 2014, 34 Pages.
Exact Sciences: "Cologuard Physician Brochure," Geneoscopy Exhibit 1080, 12 Pages.
Exact Sciences: "Cologuard(TM) sDNA-based Colorectal Cancer Screening Test-Instructions for Use," 2013, pp. 1-71.

(56) References Cited

OTHER PUBLICATIONS

Exact Sciences Corporation: Cologuard sDNA-based Colorectal Cancer Screening Test—Instructions for Use, 2013, 85 Pages.
Exact Sciences: "Patents & Trademarks," Cologuard Patents, 2014, 4 Pages, [Retrieved on Aug. 9, 2024] Retrieved from URL: https://web.archive.org/web/20141206015245/http://www.exactsciences.com:80/patents-and-trademarks.
Exact Sciences: "Patents & Trademarks," Cologuard Patents, 2024, 4 Pages, [Retrieved on Aug. 9, 2024] Retrieved from URL: https://www.exactsciences.com/patents-and-trademarks.
Extended European Search Report for EP 21788930.2, mailed Mar. 15, 2024, 8 pages.
Extended European Search Report for European Application No. 09711056.3, mailed Apr. 29, 2011, 15 Pages.
Extended European Search Report for European Application No. 11189541.3, mailed Jun. 29, 2012, 09 Pages.
Extended European Search Report for European Application No. 11760295.3, mailed Oct. 7, 2013, 8 Pages.
Extended European Search Report for European Application No. 14176500.8, mailed Nov. 21, 2014, 06 Pages.
Extended European Search Report for European Application No. 15772326.3, mailed Dec. 14, 2017, 18 Pages.
Extended European Search Report for European Application No. 15774156.2, mailed Mar. 28, 2018, 16 Pages.
Extended European Search Report for European Application No. 16842880.3, mailed Jun. 13, 2019, 9 pages.
Extended European Search Report for European Application No. 17783141.9, mailed Mar. 19, 2020, 13 Pages.
Extended European Search Report for European Application No. 17847642.0, mailed Feb. 10, 2021, 20 Pages.
Extended European Search Report for European Application No. 18744801.4, mailed Dec. 14, 2020, 22 Pages.
Extended European Search Report for European Application No. 19150809.2, mailed Dec. 6, 2019, 15 Pages.
Extended European Search Report for European Application No. 19890483.1, mailed Sep. 29, 2022, 10 Pages.
Extended European Search Report for European Application No. 20175912.3, mailed May 20, 2021, 11 Pages.
Extended European Search Report for European Application No. 20782990.4, mailed Dec. 21, 2022, 12 Pages.
Extended European Search Report for European Application No. 21157412.4, mailed Jul. 14, 2021, 05 Pages.
Extended European Search Report for European Application No. 21195952.3, mailed Apr. 12, 2022, 8 Pages.
Extended European Search Report for European Application No. 23161306.8, mailed Sep. 18, 2023, 7 Pages.
Extended European Search Report for European Application No. 23175849.1, mailed Aug. 23, 2023, 8 Pages.
Extended European Search Report for European Application No. 23191397.1, mailed Feb. 16, 2024, 10 Pages.
Extended European Search Report for European Application No. 14776150.6, mailed Jan. 3, 2017, 19 Pages.
Fackler M.J., et al., "Quantitative Multiplex Methylation-specific PCR Assay for the Detection of Promoter Hypermethylation in Multiple Genes in Breast Cancer," Cancer Research Jul. 1, 2004, vol. 64, No. 13, pp. 4442-4452 (12 Pages).
Fasman G.D., Practical Handbook of Biochemistry and Molecular Biology, CRC Press, Boca Raton, FL, 1989, pp. 385-394 (13 Pages).
Fearnhead N.S., et al., "The ABC of APC," Human Molecular Genetics, 2001, vol. 10, No. 7, pp. 721-733.
Fearon E.R., et al., "A Genetic Model for Colorectal Tumorigenesis," Cell, Jun. 1, 1990, vol. 61, pp. 759-767.
Fedurco M., et al., "BTA, a Novel Reagent for DNA Attachment on Glass and Efficient Generation of Solid-Phase Amplified DNA Colonies," Nucleic Acids Research, Feb. 9, 2006, vol. 34, No. 3, Article No. e22, 13 Pages.
Feil R., et al., Methylation Analysis on Individual Chromosomes: Improved Protocol for Bisulfite Genomic Sequencing, Nucleic Acids Research, Feb. 25, 1994, vol. 22, No. 4, pp. 695-696.
Feliciano A., et al., "miR-125b Acts as a Tumor Suppressor in Breast Tumorigenesis via Its Novel Direct Targets ENPEP, CK2-a, CCNJ, and MEGF9," PLoS One, Oct. 3, 2013, vol. 8, No. 10 (e76247), 18 Pages.
Final Office Action for U.S. Appl. No. 15/010,436, mailed Oct. 28, 2016, 15 Pages.
Finger L.D., et al., "The Wonders of Flap Endonucleases: Structure, Function, Mechanism, and Regulation," Subcellular Biochemistry, 2012, vol. 62, pp. 301-326.
"Form 10-K for Exact Sciences Corporation," United States Securities and Exchange Commission, 2023, 151 Pages.
Frommer et al., A genomic sequencing protocol that yields a positive display of 5-methylcytosine residues in individual DNA strands. Proc Natl Acad Sci USA. Mar. 1, 1992;89(5):1827-31.
Gao et al. Global Analysis of DNA Methylation in hepatocellular cariconma by a liquid hybridization cpature-based bisulfite sequencing approach Clin Epigenetics. Aug. 21, 2015;7(1):86.
Gardiner-Garden M., et al., "CpG Islands in Vertebrate Genomes," Journal of Molecular Biology, 1987, vol. 196, pp. 261-281 (22 Pages).
Garrido-Laguna I., et al., "Pancreatic Cancer: From State-of-the-art Treatments to Promising Novel Therapies," Nature Reviews Clinical Oncology, Jun. 2015, vol. 12, No. 6, pp. 1-16 (319-334).
Gatlin C.L., et al., "Automated Identification of Amino Acid Sequence Variations in Proteins by HPLC/Microspray Tandem Mass Spectrometry," Analytical Chemistry, Feb. 15, 2000, vol. 72, No. 4, pp. 757-763.
Gemperle C., et al., Regulation of the Formyl Peptide Receptor 1 (FPR1) Gene in Primary Human Macrophages, PLoS One, Nov. 21, 2012, vol. 7, No. 11 (e50195), 6 Pages.
"Genecards Record for ZNF781," Gene—Zinc Finger Protein 781, Pseudogene, Updated on Apr. 3, 2024, pp. 1-23, Retrived from URL: https://www.genecards.org/cgi-bin/carddisp.pl?gene=ZNF781.
Gevaert O., et al., "Pancancer Analysis of DNA Methylation-driven Genes Using Methylmix," Genome Biology, Biomed Central Ltd, Jan. 29, 2015, vol. 16, No. 1, p. 17, p. 9 (13 Pages), DOI: 10.1186/S13059-014-0579-8, ISSN: 1465-6906, XP021218423.
Grafstrom R H., et al., "The Characteristics of DNA Methylation in an in Vitro DNA Synthesizing System From Mouse Fibroblasts," Nucleic Acid Research, Apr. 25, 1985, vol. 13, No. 8, pp. 2827-2842.
Grandis J.R., et al., et al., "TGF-alpha and EGFR in Head and Neck Cancer," Journal of Cellular Biochemistry, 1993, Supplement 17F, pp. 188-191, 6 Pages.
Greenman C., et al., "Patterns of Somatic Mutation in Human Cancer Genomes," Nature, Mar. 8, 2007, vol. 446, No. 7132, pp. 153-158.
Grigg et al., Sequencing 5-methylcytosine residues in genomic DNA. Bioessays. Jun. 1994;16(6):431-6.
Grigg, Sequencing 5-methylcytosine residues by the bisulphite method. DNA Seq. 1996;6(4):189-98.
Grunau C., et al., "Bisulfite Genomic Sequencing: Systematic Investigation of Critical Experimental Parameters," Nucleic Acids Research, Jul. 1, 2001, vol. 29, No. 13, e65, pp. 1-7.
Guilfoyle et al., Ligation-mediated PCR amplification of specific fragments from a class-II restriction endonuclease total digest, Nucleic Acids Research, 1997, 25:1854-1858.
Guittet L., et al., "Comparison of a Guaiac Based and an Immunochemical Faecal Occult Blood Test in Screening for Colorectal Cancer in a General Average Risk Population," Gut, 2007, vol. 56, pp. 210-214.
Hall J.G., et al., "Sensitive Detection of Dna Polymorphisms by the Serial Invasive Signal Amplification Reaction," Proceedings of the National Academy of Sciences, Jul. 18, 2000, vol. 97, No. 15, pp. 8272-8277.
Hallet J., et al., "Exploring the Rising Incidence of Neuroendocrine Tumors: A Populationbased Analysis of Epidemiology, Metastatic Presentation, and Outcomes," Cancer, Feb. 15, 2015, vol. 121, No. 4, pp. 589-597.
Hammer M.F., "Human Hybrids," Scientific American, May 2012, pp. 66-71.

(56) References Cited

OTHER PUBLICATIONS

Hanley R., et al., "DNA Integrity Assay: A Plasma-Based Screening Tool for the Detection of Prostate Cancer," Clinical Cancer Research, Aug. 1, 2006, vol. 12, No. 15 pp. 4569-4574.

Hardison D.M., et al., "Stool DNA: A Viable Option for Colorectal Cancer Screening," Gastroenterology, Dec. 2005, vol. 129, No. 6, pp. 2128-2129.

Harris T.D., et al., "Single-Molecule DNA Sequencing of a Viral Genome," Science, Apr. 4, 2008, vol. 320, No. 5872, pp. 106-109 (5 Pages).

Haug U., et al., "Mutant-enriched Pcr and Allele-specific Hybridization Reaction to Detect K-ras Mutations in Stool Dna: High Prevalence in a Large Sample of Older Adults," Clinical Chemistry, Apr. 2007, vol. 53, No. 4, pp. 787-790, XP002633383, ISSN: 0009-9147.

Haug U., et al., "New Stool Tests for Colorectal Cancer Screening: A Systematic Review Focusing on Performance Characteristics and Practicalness," International Journal of Cancer, Nov. 1, 2005, vol. 117, No. 2, pp. 169-176 (9 Pages).

Hayden et al., Multiplex-Ready PCR: A new method for multiplexed SSR and SNP genotyping, BMC Genomics, 2008, 9:80.12 pages.

Hayes D.F., et al., "Circulating Tumor Cells at Each Follow-up Time Point During Therapy of Metastatic Breast Cancer Patients Predict Progression-free and Overall Survival," Clinical Cancer Research, Jul. 15, 2006, vol. 12, No. 14, pp. 4218-4224.

Hecker et al., High and low annealing temperatures increase both specificity and yield in touchdown and stepdown PCR. Biotechniques. Mar. 1996;20(3):478-85.

Heid C.A., et al., "Real Time Quantitative PCR," Genome Research, Oct. 1996, vol. 6, No. 10, pp. 986-994 (10 Pages).

Heitman S.J., et al., "Colorectal Cancer Screening for Average-Risk North Americans: An Economic Evaluation," Plos Medicine, Nov. 2010, vol. 7, No. 11 (el000370), 13 Pages.

Heller G., et al., "Genome-Wide CpG Island Methylation Analyses in Non-Small Cell Lung Cancer Patients," Carcinogenesis, 2013, vol. 34, No. 3, pp. 513-521.

Heller G., et al., "Lung Cancer: From Single-gene Methylation to Methylome Profiling," Cancer and Metastasis Reviews, Kluwer Academic Publishers, DO, Jan. 23, 2010, vol. 29, No. 1, pp. 95-107, 14 Pages, ISSN: 1573-7233, XP019787667.

Henegariu O., et al., "Multiplex PCR: Critical Parameters and Step-by-Step Protocol," Biotechniques, Sep. 1997, vol. 23, pp. 504-511, XP000703350.

Hesselink A.T., et al., "Combined Promoter Methylation Analysis of CADM1 and MAL: An Objective Triage Tool for High-Risk Human Papillomavirus DNA-Positive Women," Clinical Cancer Research, Apr. 15, 2011, vol. 17, No. 8, pp. 2459-2465.

Higuchi et al., Kinetic PCR analysis: real-time monitoring of DNA amplification reactions, Biotechnology, 1993, 11:1026-1030.

Higuchi R., et al., "A General Method of in Vitro Preparation and Specific Mutagenesis of DNA Fragments: Study of Protein and Dna Interactions," Nucleic Acids Research, 1988, vol. 16, No. 15, pp. 7351-7367.

Higuchi R., et al., "Simultaneous Amplification and Detection of Specific DNA Sequences," Biotechnology, NY, Apr. 1992, vol. 10, No. 4, pp. 413-417, (7 Pages).

Hiraoka A., et al., "Cloning, Expression, and Characterization of a cDNA Encoding a Novel Human Growth Factor for Primitive Hematopoietic Progenitor Cells," Medical Sciences, Proceedings of the National Academy of Sciences of the United States of America, Jul. 8, 1997, vol. 94, No. 14, pp. 7577-7582.

Hiraoka A., "Leukemia Cell Lines Require Self-secreted Stem Cell Growth Factor (SCGF) for Their Proliferation," Leukemia Research, Oct. 2008, vol. 32, vol. 10, pp. 1623-1625.

Hirata I., et al., "Usefulness of Fecal Lactoferrin and Hemoglobin in Diagnosis of Colorectal Diseases," World Journal of Gastroenterology, Mar. 14, 2007, vol. 13, No. 10, pp. 1569-1574.

Hoepffner N., et al., "Comparative Evaluation of a New Bedside Faecal Occult Blood Test in a Prospective Multicentre Study," Alimentary Pharmacology & Therapeutics, Jan. 1, 2006, vol. 23, No. 1, pp. 145-154.

Horikoshi T., et al., "Quantitative Determination of the Ratio of Mutated to Normal ras Genes in the Blood of Leukemia Patients by Allele-Specific PCR," Leukemia Research, Sep. 1994, vol. 18, No. 9, pp. 693-702.

Hua D., et al., "Quantitative Methylation Analysis of Multiple Genes Using Methylation-Sensitive Restriction Enzyme-based Quantitative PCR for the Detection of Hepatocellular Carcinoma," Experimental and Molecular Pathology, Aug. 2011, vol. 91, No. 1, pp. 455-460.

Huang J., et al., "Transactivation of the Epidermal Growth Factor Receptor by Formylpeptide Receptor Exacerbates the Malignant Behavior of Human Glioblastoma Cells," Cancer Research, Jun. 15, 2007, vol. 67, No. 12, pp. 5906-5913 (9 Pages).

Huang W., et al., "Analysis of DNA Methylation in Plasma for Monitoring Hepatocarcinogenesis," Genetic Testing and Molecular Biomarkers, United States, Jun. 1, 2015, vol. 19, No. 6, pp. 295-302 (9 Pages).

International Search Report and Written Opinion for International Application No. PCT/GB2010/000180, mailed Mar. 11, 2011, 30 Pages.

International Search Report and Written Opinion for International Application No. PCT/US2009/033793, mailed Sep. 24, 2009, 7 Pages.

International Search Report and Written Opinion for International Application No. PCT/US2014/024582, mailed Sep. 24, 2014, 20 Pages.

International Search Report and Written Opinion for International Application No. PCT/US2014/024589, mailed Sep. 29, 2014, 23 Pages.

International Search Report and Written Opinion for International Application No. PCT/US2016/049653, mailed Feb. 3, 2017, 20 Pages.

International Search Report and Written Opinion for International Application No. PCT/US2016/058875, mailed Apr. 21, 2017, 17 Pages.

International Search Report and Written Opinion for International Application No. PCT/US2017/027439, mailed Sep. 13, 2017, 26 Pages.

International Search Report and Written Opinion for International Application No. PCT/US2017/049915, mailed Jan. 18, 2018, 22 Pages.

International Search Report and Written Opinion for International Application No. PCT/US2018/015535, mailed Jun. 25, 2018, 20 Pages.

International Search Report and Written Opinion for International Application No. PCT/US2018/019982, mailed Jul. 27, 2018, 18 Pages.

International Search Report and Written Opinion for International Application No. PCT/US2018/062809, mailed May 1, 2019, 36 Pages.

International Search Report and Written Opinion for International Application No. PCT/US2019/063401, mailed Feb. 20, 2020, 12 Pages.

International Search Report and Written Opinion for International Application No. PCT/US2020/048270, mailed Dec. 7, 2020, 15 Pages.

International Search Report and Written Opinion for International Application No. PCT/US2021/027770, mailed Aug. 5, 2021, 12 Pages.

International Search Report and Written Opinion for International Application No. PCT/US2021/030635, mailed Oct. 26, 2021, 32 Pages.

International Search Report and Written Opinion for International Application No. PCT/US2022/014408, mailed Jun. 21, 2022, 19 Pages.

International Search Report and Written Opinion for International Application No. PCT/US2022/079270, mailed Feb. 22, 2023, 24 Pages.

(56) References Cited

OTHER PUBLICATIONS

International Search Report and Written Opinion for International Application No. PCT/US2023/085117, mailed Apr. 29, 2024, 12 Pages.
International Search Report and Written Opinion for PCT/US2017/024468, mailed Sep. 1, 2017, 17 pages.
International Search Report and Written Opinion for PCT/US2020/026581. Mailed Aug. 31, 2020. 24 pages.
Iqbal U., et al., "Safety and Efficacy of a Minimally Invasive Cell Sampling Device ('Cytosponge') in the Diagnosis of Esophageal Pathology: A Systematic Review," European Journal of Gastroenterology & Hepatology, Nov. 2018, vol. 30, No. 11, pp. 1261-1269.
Ito S., et al., "Tet Proteins Can Convert 5-methylcytosine to 5-formylcytosine and 5-Carboxylcytosine," Science, Sep. 2, 2011, vol. 333, No. 6047, pp. 1300-1303 (9 Pages).
Ito Y., et al., "The Utility of Formalin-fixed and Paraffin-embedded Tissue Blocks for Quantitative Analysis of N-acetylgalactosamine 4-sulfate 6-O-sulfotransferase mRNA Expressed by Colorectal Cancer Cells," Acta Histochemica Et Cytochemica, JP, Jan. 1, 2007, vol. 40, No. 2, pp. 53-59, DOI:10.1267/ahc.07004, ISSN 0044-5991, XP055452280.
Itzkowitz S., et al., "A Simplified, Noninvasive Stool DNA Test for Colorectal Cancer Detection," American Journal of Gastroenterology, 2008, vol. 103, pp. 2862-2870.
Itzkowitz S.H., et al., "T1098: Improved Non-Invasive Stool DNA (SDNA) Test to Screen for Colorectal Cancer (CRC): Validation of High Sensitivity and Specificity," Gastroenterology, Apr. 2008, vol. 134, No. 4, Supplement A-483, 1 Page.
Iyer P., et al., "Concordance of DNA Methylation Pattern in Plasma and Tumor DNA of Egyptian Hepatocellular Carcinoma Patients," Experimental and Molecular Pathology, Feb. 2010, vol. 88, No. 1, pp. 107-111.
Iyer P.G., et al., "Accurate Nonendoscopic Detection of Barrett's Esophagus by Methylated DNA Markers: a Multisite Case Control Study," American Journal of Gastroenterology, Aug. 2020, vol. 115, pp. 1201-1209.
Iyer P.G., et al., "Accurate Non-Endoscopic Detection of Barrett's Esophagus in a Multicenter Prospective Validation Cohort: The SOS 2 Trial," AGA Abstracts, 2018, 878, pp. S-175-S-176.
Iyer P.G., et al., "Highly Discriminant Methylated DNA Markers for the Non-endoscopic Detection of Barrett's Esophagus," The American Journal of Gastroenterology, Aug. 2018, vol. 113, No. 8, pp. 1-11 (1156-1166).
Iyer P.G., et al., "Independent Validation of an Accurate Methylated DNA Marker Panel for the Non-Endoscopic Detection of Barrett's Esophagus: A Multisite Case Control Study," AGA Abstracts, 2020, 1084, p. S-211.
Jessup J.M., et al., "Diagnosing Colorectal Carcinoma: Clinical and Molecular Approaches," A Cancer Journal for Clinicians, 1997, vol. 47, No. 2, pp. 70-92.
Jiang P., et al., "Lengthening and Shortening of Plasma DNA in Hepatocellular Carcinoma Patients," Proceedings of the National Academy of Sciences of the United States of America, Mar. 17, 2015, vol. 112, No. 11, pp. E1317-E1325.
Jiang X., et al., "T1102: Detection of Colorectal Neoplasia By Stool DNATesting: High Discrimination with Multi-Marker Quantitation," Gastroenterology, Apr. 2008, vol. 134, No. 4, Supplement A-484, 1 Page.
Johansson M., et al., "One-Carbon Metabolism and Prostate Cancer Risk: Prospective Investigation of Seven Circulating B Vitamins and Metabolites," Cancer Epidemiology Biomarkers & Prevention, May 1, 2009, American Association for Cancer Research, vol. 18, No. 5, pp. 1535-1543, XP093120606.
Johnson K.C., et al., "DNA Methylation in Ductal Carcinoma in Situ Related With Future Development of Invasive Breast Cancer" Clinical Epigenetics, 2015, vol. 7, No. 1: 75, 12 Pages, Published Online on Jul. 25, 2015.
Jongeneel C.V., et al., "An Atlas of Human Gene Expression from Massively Parallel Signature Sequencing (MPSS)," Genome Research, Jul. 2005, vol. 15, No. 7, pp. 1007-1014.
Jung X., et al., "T1102: Detection of Colorectal Neoplasia By Stool DNA Testing: High Discrimination with Multi-Marker Quantitation," Gastroenterology, Elsevier, Philadelphia, PA, Apr. 1, 2008, vol. 134, No. 4, p. A-484 (1 Page), DOI: 10.1016/S0016-5085(08)62263-5, ISSN:0016-5085, XP023434060, [Retrieved on Apr. 1, 2008].
Jung Y., et al., "Gene Silencing of TSPYL5 Mediated by Aberrant Promoter Methylation in Gastric Cancers," Laboratory Investigation, Feb. 2008, vol. 88, pp. 153-160.
Kacian D L., et al., "A Replicating RNA Molecule Suitable for a Detailed Analysis of Extracellular Evolution and Replication," Proceedings of the National Academy of Sciences of the United States of America, Oct. 1972, vol. 69, No. 10, pp. 3038-3042.
Kahi C.J., et al., "Screening, Surveillance, and Primary Prevention for Colorectal Cancer: A Review of the Recent Literature," Gastroenterology, Aug. 2008, vol. 135, pp. 380-399.
Kaiser M.W., et al., "A Comparison of Eubacterial and Archaeal Structure-specific 5'-Exonucleases," Journal of Biological Chemistry, Jul. 23, 1999, vol. 274, No. 30, pp. 21387-21394.
Kaiser M.W., et al., "A Comparison of Eubacterial and Archaeal Structure-Specific 5'-Exonucleases," The Journal of Biological Chemistry, Jul. 23, 1999, vol. 274, No. 30, pp. 21387-21394.
Kalinina et al., Nanoliter scale PCR with TaqMan detection, Nucleic Acids Research, 1997, 25:1999-2004.
Kanaoka S., et al., Potential Usefulness of Detecting Cyclooxygenase 2 Messenger RNA in Feces for Colorectal Cancer Screening, Gastroenterology, Aug. 2004, vol. 127, pp. 422-427.
Kang G.H., et al., "DNA Methylation Profiles of Gastric Carcinoma Characterized by Quantitative DNA Methylation Analysis," Laboratory Investigation, Feb. 2008, vol. 88, No. 2, pp. 161-170.
Kang G.H., et al., "DNA Methylation Profiles of Gastric Carcinoma Characterized by Quantitative DNA Methylation Analysis," Laboratory Investigation, Feb. 2008, vol. 88, pp. 161-170.
Karl J., et al., "Improved Diagnosis of Colorectal Cancer Using a Combination of Fecal Occult Blood and Novel Fecal Protein Markers," Clinical Gastroenterology and Hepatology, Oct. 2008, vol. 6, No. 10, pp. 1122-1128.
Kastury K., et al., "Chromosome Locations of Human EMX and OTX Genes," Genomics, 1994, vol. 22, pp. 41-45 (7 Pages).
Kim B-H., et al., "Methylation Profiles of Multiple CpG Island Loci in Extrahepatic Cholangiocarcinoma Versus Those of Intrahepatic Cholangiocarcinomas," Archives of Pathology & Laboratory Medicine, Jun. 2007, vol. 131, pp. 923-930.
Kinzler K.W., et al., "Lessons from Hereditary Colorectal Cancer," Cell, Oct. 18, 1996, vol. 87, pp. 159-170.
Kisiel J B., et al., "Hepatocellular Carcinoma Detection by Plasma Methylated DNA: Discovery, Phase I Pilot, and Phase II Clinical Validation," Hepatology, Mar. 2019, vol. 69, No. 3, pp. 1180-1192.
Kisiel J.B., et al., "Methylated Eyes Absent 4 (EYA4) Gene Promoter in Non-neoplastic Mucosa of Ulcerative Colitis Patients With Colorectal Cancer: Evidence for a Field Effect," Inflammatory Bowel Diseases, Sep. 2013, vol. 19, No. 10, pp. 2079-2083.
Kisiel J.B., et al., "New DNA Methylation Markers for Pancreatic Cancer: Discovery, Tissue Validation, and Pilot Testing in Pancreatic Juice," Clinical Cancer Research, Oct. 1, 2015, vol. 21, No. 19, pp. 4473-4481.
Kisiel J.B., et al., "Novel Methylated DNA Markers Predict Site of Gastrointestinal Cancer," AGA Abstracts, May 2013, #469, p. S-84 (1 Page).
Kisiel J.B., et al., "Novel Stool DNA Markers for Inflammatory Bowel Disease Asociated Colorectal Cancer High Grade Dysplasia: High Specificity Across Three Independent International Populations," Abstract 185, Gatroenterology, 2016, vol. 150, No. 4, p. S-48.
Kisiel J.B., et al., "Stool DNA Testing for the Detection of Pancreatic Cancer: Identification and Assessment of Methylation Marker Candidates," Gastroenterology, Apr. 21, 2011, vol. 140, No. 5, p. s-185 (01 Page), DOI: 10.1016/S0016-5085(11)60746-4, XP055435985, (The Whole Document).
Kisiel J.B., et al., "Su1340 Detection of Colorectal Cancer and Polyps in Patients with Inflammatory Bowel Disease by Novel Methylated Stool DNA Markers," Gastroenerology, May 1, 2014, vol. 146, No. 5, pp. S-440-S-441 (2 Pages).

(56) References Cited

OTHER PUBLICATIONS

Kling D., "Ultrafast DNA Sequencing," Nature Biotechnology, Dec. 2003, vol. 21, No. 12, pp. 1425-1427.
Kneip C., et al., "SHOX2 DNA Methylation is a Biomarker for the Diagnosis of Lung Cancer in Plasma," Journal of Thoracic Oncology, Oct. 2011, vol. 6, No. 10, pp. 1632-1638.
Knute D., et al., "MicroRNAs as Novel Targets for NSAID Chemoprevention of Color Carcinogenesis," Gastroenterology, May 10, 2011, vol. 140, No. 5, p. S-41, XP055201244.
Koinuma K., et al., "Screening for Genomic Fragments That Are Methylated Specifically in Colorectal Carcinoma With a Methylated MLH1 Promoter," Carcinogenesis, Jul. 20, 2005, vol. 26, No. 12, pp. 2078-2085.
Korbie D., et al., "Multiplex Bisulfite PCR Resequencing of Clinical FFPE DNA," Clinical Epigenetics, 2015, vol. 7 (28), pp. 1-12 (12 Pages).
Kraunz K.S., et al., "Interaction Between the Bone Morphogenetic proteins and Ras/MAP-kinase Signalling Pathways in Lung Cancer," British Journal of Cancer, 2005, vol. 93, No. 8, pp. 949-952.
Kristensen L.S., et al., "PCR-based Methods for Detecting Single-locus DNA Methylation Biomarkers in Cancer Diagnostics, Prognostics, and Response to Treatment," Clinical Chemistry, Aug. 2009, vol. 55, No. 8, pp. 1471-1483.
Kutzner N., et al., "Non-Invasive Detection of Colorectal Tumours by the Combined Application of Molecular Diagnosis and the Faecal Occult Blood Test," Cancer Letters, 2005, vol. 229, pp. 33-41.
Laird P.W., et al., "The Power and the Promise of DNA Methylation Markers," Nature Reviews, Cancer, Apr. 2003, vol. 3, No. 4, pp. 253-266.
Lange C.P.E., et al., "Genome-scale Discovery of Dna-methylation Biomarkers for Blood-based Detection of Colorectal Cancer," PLOS ONE, Nov. 28, 2012, vol. 7, No. 11:e50266, pp. 1-10, XP055756627, DOI: 10.1371/journal.pone.0050266.
Lee H.S., et al., "Prognostic Implications of and Relationship Between CpG Island Hypermethylation and Repetitive DNA Hypomethylation in Hepatocellular Carcinoma," Clinical Cancer Research, Feb. 1, 2009, vol. 15, No. 3, pp. 812-820 (10 Pages).
Lenhard K., et al., "Analysis of Promoter Methylation in Stool: A Novel method for the Detection of Colorectal Cabcer," Clinical Gastroenterology and Hepatology, Feb. 2005, vol. 3, pp. 142-149.
Lenhard K., et al., "Analysis of Promoter Methylation in Stool: a Novel Method for the Detection of Colorectal Cancer," Clinical Gastroenterology and Hepatology, 2005, vol. 3, No. 2, pp. P142-P149, [Retrieved on Jan. 9, 2024] Retrieved from URL: https://www.cghjournal.org/article/S1542-3565(04)00624-X/fulltext.
Leontiou C.A., et al., "Bisulfite Conversion of DNA: Performance Comparison of Different Kits and Methylation Quantitation of Epigenetic Biomarkers That Have the Potential to Be Used in Non-Invasive Prenatal Testing," PLoS One, Aug. 6, 2015, vol. 10, No. 80, pp. 1-22, e0135058.
Leung W.K., et al., "Detection of Hypermethylated DNA or Cyclooxygenase-2 Messenger RNA in Fecal Samples of Patients with Colorectal Cancer or Polyps," American Journal of Gastroenterology, 2007, vol. 102, pp. 1070-1076 (8 Pages).
Levi Z., et al., "A Quantitative Immunochemical Faecal Occult Blood Test is More Efficient for Detecting Significant Colorectal Neoplasia Than a Sensitive Guaiac Test," Alimentary Pharmacology & Therapeutics, May 1, 2006, vol. 23, No. 9, pp. 1359-1364.
Levin T.R., et al., "Genetic Biomarker Prevalence Is Similar in Fecal Immunochemical Test Positive and Negative Colorectal Cancer Tissue," Digestive Diseases and Sciences, Mar. 2017, vol. 62, No. 3, pp. 678-688.
Levin T.R., et al., "Prevalence of DNA Biomarkers in Fecal Immunochemical Test Positive and Negative Colorectal Cancers," Abstract SA1050, Gastroenterology, Apr. 2015, vol. 148, No. 4, Supplement. 1, pp. S-207-S-208.
Li et al., MethPrimer: designing primers for methylation PCRs. Bioinformatics. Nov. 2002;18(II):1427-31.
Li X., et al., "Selection and Application of Tissue microRNAs for Nonendoscopic Diagnosis of Barrett's Esophagus," Gastroenterology, Sep. 2018, vol. 155, No. 3, pp. 771-783.e3.
Lidgard et al.. Clinical performance of an automated stool DNA assay for detection of colorectal neoplasia. Clin Gastroenterol Hepatol. Oct. 2013;II(10):1313-8.
Linkedin: "LinkedIn Page of Joost Louwagie," 3 Pages, [Retrieved on Jan. 10, 2024] Retrieved from URL: https://www.linkedin.com/in/joost-louwagie/?originalSubdomain=ch.
Liu Y., et al., "Bisulfite-free Direct Detection of 5-Methylcytosine and 5-Hydroxymethylcytosine at Base Resolution," Nature Biotechnology, 2019, vol. 37, pp. 424-429 (11 pages), doi:10.1038/s41587-019-0041-2, XP055737047.
Liu Y., et al., "Flap Endonuclease 1: A Central Component of DNA Metabolism," Annual Review of Biochemistry, 2004, vol. 73, pp. 589-615 (29 Pages).
Lofton-Day et al. Clinical Chemistry, vol. 54, No. 2, pp. 414-423, 2008.
Loh K., et al., "Bone Morphogenic Protein 3 Inactivation is an Early and Frequent Event in Colorectal Cancer Development," Genes Chromosomes and Cancer, Jun. 2008, vol. 47, No. 6, pp. 449-460, (Published Online on Feb. 29, 2008).
Louwagie J., et al., "Feasibility of a DNA Methylation Assay for Noninvasive CRC Screening," Clinical Cancer Research, B16, Oct. 2007, vol. 13, Issue No. 19 Supplement, 4 Pages.
Lowe T., et al., "A Computer Program for Selection of Oligonucleotide Primers for Polymerase Chain Reactions," Nucleic Acids Research, 1990, vol. 18, No. 7, pp. 1757-1761.
Lyamichev et al., Polymorphism identification and quantitative detection of genomic DNA by invasive cleavage of oligonucleotide probes, Nat. Biotech., 1999, 17:292-296.
Machiels B.M., et al., "New Protocol for DNA Extraction of Stool," Biotechniques, Feb. 2000, vol. 28, No. 2, pp. 286-290 (6 Pages).
Mahon S.M., "Prevention and Screening of Gastrointestinal Cancers," Seminars in Oncology Nursing, Feb. 2009, vol. 25, No. 1, pp. 15-31.
Maitra A., et al., "Pancreatic Cancer," Annual Review of Pathology: Mechanisms of Disease, 2008, vol. 3, pp. 157-188, 30 Pages.
Majumder et al. Molecular detection of pancreatic neoplasia: Current status and future promise, World J. Gastroenterol Oct. 28, 2015; 21(40): 11387-11395.
Majumder S., et al., "Detection of Pancreatic High-Grade Dysplasia and Cancer using Novel Methylated DNA Markers: Discovery and Tissue Validation," Gastroenterology, 2016, vol. 150, No. 4, 596, pp. S120-S121.
Majumder S., et al., "High Detection Rates of Pancreatic Cancer Across Stages by Plasma Assay of Novel Methylated DNA Markers and CA 19-9," Clinical Cancer Research, May 1, 2021, vol. 27, No. 9, pp. 2523-2532 (22 Pages).
Majumder S., et al., "Novel DNA Methylation Markers Assayed from Cyst Fluid Accurately Detect Advanced Neoplasia in Pancreatic Cysts: A Multicenter Study," Gastroenterology, AGA Abstracts, 2017, vol. 152, No. 5, S148.
Mandal P., et al., "Signaling in Lipopolysaccharide-Induced Stabilization of Formyl Peptide Receptor 1 mRNA in Mouse Peritoneal Macrophages," Journal of Immunology, Feb. 15, 2007, vol. 178, No. 4, pp. 2542-2548 (8 Pages).
Mandal P., et al., "Lipopolysaccharide Induces Formyl Peptide Receptor 1 Gene Expression in Macrophages and Neutrophils via Transcriptional and Posttranscriptional Mechanisms," Journal of Immunology, Nov. 1, 2005, vol. 175, No. 9, pp. 6085-6091 (8 Pages).
Mandel J.S., et al., "The Effect of Fecal Occult-blood Screening on the Incidence of Colorectal Cancer," The New England Journal of Medicine, Nov. 30, 2000, vol. 343, No. 22, pp. 1603-1607.
Marabella P.C., et al., "Serum Ribonuclease in Patients with Lung Carcinoma," Journal of Surgical Oncology, 1976, vol. 8, No. 6, pp. 501-505.
Margulies M., et al., "Genome Sequencing in Microfabricated High-density Picolitre Reactors." Nature, Sep. 15, 2005, vol. 437, pp. 376-380 (6 Pages).
Martin V., et al., Genomic Sequencing Indicates a Correlation Between DNA Hypomethylation in the 5' Region of the PS2 Gene

(56) References Cited

OTHER PUBLICATIONS and Its Expression in Human Breast Cancer Cell Lines, Gene, May 19, 1995, vol. 157, No. 1-2, pp. 261-264.
Matsumura Y., et al., "Significance of CD44 Gene Products for Cancer Diagnosis and Disease Evaluation," The lancet, Oct. 31, 1992, vol. 340, pp. 1053-1058.
Matsumura Y., et al., "Non-Invasive Detection of Malignancy by Identification of Unusual CD44 Gene Activity in Exfoliated Cancer Cells," BMJ, Mar. 5, 1994, vol. 308, pp. 619-624.
Matsushita et al., DNA-friendly Cu(ii)/TEMPO-catalyzed 5-hydroxymethylcytosinespecific oxidation. Chem Commun (Camb). May 23, 2017;53(42):5756-5759.
Medina-Aguilar R., et al., "Methylation Landscape of Human Breast Cancer Cells in Response to Dietary Compound Resveratrol," PLoS One, Jun. 29, 2016, vol. 11, No. 6(e0157866), 20 Pages.
Meissner A., et I., "Reduced Representation Bisulfite Sequencing for Comparative High-resolution DNA Methylation Analysis," Nucleic Acids Research, 2005, vol. 33, No. 18, pp. 5868-5877, DOI:10.1093/nar/gki901, XP002661907.
Melnikov A.A., et al., "MSRE-PCR for Analysis of Gene-Specific DNA Methylation," Nucleic Acids Research, Jun. 8, 2005, vol. 33, No. 10, Article No. e93, 7 Pages.
Melotte V., et al., "N-MYC Downstream Regulated Gene 4 (Ndrg4) Promoter Methylation is a Sensitive and Specific Biomarker for Colorectal Cancer," Cellular Oncology, 2008, vol. 30, No. 2, p. 181 (2 Pages).
Melvin D.M., et al., "Laboratory Procedures for the Diagnosis of Intestinal Parasites," Third Edition, Published by U.S. Department of Health and Human Services, Centers for Disease Control, Atlanta, Georgia, 1982, 284 Pages.
Mercer D.W., "Use of Multiple Markers to Enhance Clinical Utility," Immunology Series, 1990, vol. 53, pp. 39-54.
Mitchell S.M., et al., "A Panel of Genes Methylated with High Frequency in Colorectal Cancer," BMC Cancer, Jan. 31, 2014, vol. 14, No. 54, 15 Pages.
Mitchell S.M., et al., "Evaluation of Methylation Biomarkers for Detection of Circulating Tumor DNA and Application to Colorectal Cancer," Genes, Basel, Dec. 15, 2016, vol. 7, No. 12 (125), 11 Pages, XP055725652.
Modiano N., et al., "Risk Factors for the Detection of Barrett's Esophagus in Patients With Erosive Esophagitis," Gastrointestinal Endoscopy, May 2009, vol. 69, No. 6, pp. 1014-1020.
Moinova H.R., et al., "Identifying DNA Methylation Biomarkers for Non-endoscopic Detection of Barrett's Esophagus," Science Translational Medicine, Jan. 17, 2018, vol. 10, pp. 1-11, (424) eaao5848.
Monte M., et al., "Cloning, Chromosome Mapping and Functional Characterization of a Human Homologue of Murine Gtse-1 (B99) Gene," Gene, Aug. 22, 2000, vol. 254, No. 1-2, pp. 229-236.
Monte M., et al., "hGTSE-1 Expression Stimulates Cytoplasmic Localization of p53," Journal of Biological Chemistry, Mar. 19, 2004, vol. 279, No. 12, pp. 11744-11752.
Monteiro L., et al., "Complex Polysaccharides as PCR Inhibitors in Feces: Helicobacter Pylori Model," The Journal of Clinical Microbiology, Apr. 1997, vol. 35, No. 4, pp. 995-998, (5 Pages).
Moon J.W., et al., "Identification of Novel Hypermethylated Genes and Demethylating Effect of Vincristine in Colorectal Cancer," Journal of Experimental & Clinical Cancer Research, 2014, vol. 33, No. 4, pp. 1-10.
Moreno J.G., et al., "Circulating Tumor Cells Predict Survival in Patients With Metastatic Prostate Cancer," Urology, Apr. 2005, vol. 65, No. 4, pp. 713-718.
Morris S., et al., "Whole Blood FPR1 mRNA Expression Predicts Both Non-small Cell and Small Cell Lung Cancer," International Journal of Cancer, Jun. 1, 2018, vol. 142, No. 11, pp. 2355-2362.
Mulder S.A., et al., "Tumor Pyruvate Kinase Isoenzyme Type M2 and Immunochemical Fecal Occult Blood Test: Performance in Screening for Colorectal Cancer," European Journal of Gastroenterology & Hepatology, Oct. 2007, vol. 19, No. 10, pp. 878-882 (6 Pages).

Muller H.M., et al., "Methylation Changes in Faecal Dna: a Marker for Colorectal Cancer Screening?," Lancet, Apr. 17, 2004, vol. 363, No. 9417, pp. 1283-1285.
Munson K., et al., "Recovery of Bisulfite-converted Genomic Sequences in the Methylation-sensitive QPCR," Nucleic Acids Research, 2007, vol. 35, No. 9, pp. 2893-2903.
Muppa P., et al., "Verrucous Carcinoma of the Esophagus Shares a Methylation Profile With Usual Esophageal Squamous Carcinoma," Annual Meeting Abstracts, Feb. 2017, p. 189A.
Nakamoto M., et al., "Diverse Roles for the Eph Family of Receptor Tyrosine Kinases in Carcinogenesis," Microscopy Research and Technique, 2002, vol. 59, pp. 58-67.
Nanjo S., et al., "Identification of Gastric Cancer Risk Markers That Are Informative in Individuals with Past Infection," Gastric Cancer, Springer, Verlag, Jan. 12, 2012, vol. 15, No. 4, pp. 382-388, DOI:10.1007/S10120-011-0126-1, ISSN 1436-3305, XP035128377.
Naruse S., et al., "Fecal Pancreatic Elastase: a Reproducible Marker for Severe Exocrine Pancreatic Insufficiency," Journal of Gastroenterology, Sep. 2006, vol. 41, No. 9, pp. 901-908, JP LNKD-DOI:10.1007/S00535-006-1884-0, XP002633384, ISSN: 0944-1174.
NCBI Genbank: "*Homo sapiens* Formyl Peptide Receptor 1 (FPR1), Transcript Variant 1, mRNA," NCBI Reference Sequence No. NM_001193306.1, Apr. 9, 2019, 5 Pages, [Retrieved on Sep. 29, 2022] Retrieved from NCBI Website.
NCBI Genbank: "*Homo sapiens* S100 Calcium Binding Protein A12 (S100A12), mRNA," NCBI Reference Sequence No. NM_005621.2, Sep. 11, 2022, pp. 1-4, [Retrieved on Sep. 29, 2022].
Nechvatal J.M., et al., "Fecal Collection, Ambient Preservation, and DNA Extraction for PCR Amplification of Bacterial and Human Markers from Human Feces," Journal of Microbiological Methods, 2008, vol. 72, No. 2, pp. 124-132.
Nelson H.H., et al., "k-ras Mutation and Occupation Asbestos Exposure in Lung Adenocarcinoma: Asbestos-related Cancer without Asbestosis," Cancer Research, Sep. 15, 1999, vol. 59, pp. 4570-4573, 5 Pages.
Neuwelt E.A., et al., "Possible Sites of Origin of Human Plasma Ribonucleases as Evidenced by Isolation and Partial Characterization of Ribonucleases from Several Human Tissues," Cancer Research, Jan. 1978, vol. 38, No. 1, pp. 88-93.
NG C.K.Y., et al., "Circulating Cell-Free DNA in Hepatocellular Carcinoma: Current Insights and Outlook," Frontiers in Medicine (Lausanne), Mar. 26, 2018, vol. 5, Article No. 78, pp. 1-10.
Nilsson E., et al., "Altered DNA Methylation and Differential Expression of Genes Influencing Metabolism and Inflammation in Adipose Tissue From Subjects With Type 2 Diabetes," Diabetes, Sep. 2014, vol. 63, pp. 2962-2976.
Nishikawa T., et al., "A Simple Method of Detecting K-ras Point Mutations in Stool Samples for Colorectal Cancer Screening Using One-Step Polymerase Chain Reaction/Restriction Fragment Length Polymorphism Analysis," Clinica Chimica Acta, 2002, vol. 318, pp. 107-112.
Non-Final Office Action for U.S. Appl. No. 17/936,335, mailed Jan. 11, 2003, 07 Pages.
Non-Final Office Action for U.S. Appl. No. 18/179,945, mailed Jul. 6, 2023, 7 Pages.
Notice of Intent to Issue Ex Parte Reexamination Certificate for U.S. Pat. No. 11,634,781 mailed Oct. 18, 2023, 5 Pages.
Notice of Opposition and Statement for European Application No. 3434791, dated Mar. 5, 2021, 16 Pages.
Noutsias M., et al., "Preamplification Techniques for Real-time Rt-pcr Analyses of Endomyocardial Biopsies," BMC Molecular Biology, Jan. 14, 2008, vol. 9, Article No. 3, 20 Pages.
Nyce J., et al., "Variable Effects of Dna-synthesis Inhibitors Upon DNA Methylation in Mammalian Cells," Nucleic Acids Research, May 27, 1986, vol. 14, No. 10, pp. 4353-4367.
O'Driscoll L., et al., "Feasibility and Relevance of Global Expression Profiling of Gene Transcripts in Serum from Breast Cancer Patients Using Whole Genome Microarrays and Quantitative RT-PCR," Cancer Genomics & Proteomics, Mar-Apr. 2008, vol. 5, No. 2, pp. 94-104.
Odze R.D., et al., "Genetic Alterations in Chronic Ulcerative Colitis-Associated Adenoma-Like DALMs Are Similar to Non-

(56) References Cited

OTHER PUBLICATIONS

Colitic Sporadic Adenomas," The American Journal of Surgical Pathology, 2000, vol. 24, No. 9, pp. 1209-1216.
Office Action for Korean Patent Application No. 10-2018-7032924, 20187032924, mailed Aug. 18, 2021, 16 Pages.
Oh T., et al., "Genome-wide Identification and Validation of a Novel Methylation Biomarker, SDC2, for Blood-based Detection of Colorectal Cancer," The Journal of Molecular Diagnostics, Jul. 2013, vol. 15, No. 4, pp. 498-507.
Ohlsson L., et al., "Biomarker Selection for Detection of Occult Tumour Cells in Lymph Nodes of Colorectal Cancer Patients Using Real-time Quantitative RT-PCR," British Journal of Cancer, Jul. 17, 2006, vol. 95, No. 2, pp. 218-225.
Oishi et al., Hypermethylation of Sox17 gene is usevul as a moleculat diagnostic application in early gastric cancer. Tumor Biol. 2012;33:383-393.
Okamoto A., et al., "5-Hydroxymethylcytosine-Selective Oxidation With Peroxotungstate," Chemical Communications, Oct. 28, 2011, vol. 47, No. 40, pp. 11231-11233.
Olek A., et al., "A Modified and Improved Method for Bisulphite Based Cytosine Methylation Analysis," Nucleic Acids Research, Dec. 15, 1996, vol. 24, No. 24, pp. 5064-5066.
Olek A., et al., "The Pre-implantation Ontogeny of the H19 Methylation Imprint," Nature Genetics, Nov. 1997, vol. 17, No. 3, pp. 275-276.
Olivier M., "The Invader Assay for SNP Genotyping," Mutation Research, Jun. 3, 2005, vol. 573, No. (1-2), pp. 103-110.
Olkhov-Mitsel E., et al., "Novel Multiplex MethyLight Protocol for Detection of DNA Methylation in Patient Tissues and Bodily Fluids," Scientific Reports, Mar. 21, 2014, vol. 4, No. 4432, 8 Pages.
Ooki A., et al., "Potential Utility of HOP Homeobox Gene Promoter Methylation as a Marker of Tumor Aggressiveness in Gastric Cancer," Oncogene, Jun. 3, 2010, vol. 29, No. 22, pp. 3263-3275, (Published Online on Mar. 15, 2010).
Oort F.A., et al., "S1117: Faecal Occult Blood Tests: Immunological Superior to Guaiac Based?," Gastroenterology, Apr. 2008, vol. 134, No. 4, Supplement A-181, 1 Page.
Order Granting Request for Ex Parte Reexamination for U.S. Pat. No. 11,634,781, mailed Jun. 29, 2023, 18 Pages.
Orpana A.K., "Fluorescence Resonance Energy Transfer (FRET) Using ssDNA Binding Fluorescent Dye," Biomolecular Engineering, Apr. 2004, vol. 21, No. 2, pp. 45-50.
Osman M., et al., "Expression of Matrix Metalloproteinases and Tissue Inhibitors of Metalloproteinases Define the Migratory Characteristics of Human Monocyte-derived Dendritic Cells," Immunology, Jan. 2002, vol. 105, No. 1, pp. 73-82.
Ostrow J.D., "Tests for Fecal Occult Blood," Chapter 98 in Clinical Methods: The History, Physical, and Laboratory Examinations. Third Edition, Editors. Walker et al., Boston: Butterworths, 1990, pp. 489-491 (3 Pages).
Ota T., et al., "Complete Sequencing and Characterization of 21,243 Full-length Human cDNAs," Nature Genetics, Jan. 2004, vol. 36, No. 1, pp. 40-45.
Pant K.D., et al., "Noninvasive Colorectal Cancer Screening," Digestive Diseases and Sciences, Jun. 2002, vol. 47, No. 6, pp. 1236-1240.
Pantel K., et al., "Detection, Clinical Relevance and Specific Biological Properties of Disseminating Tumour Cells," Nature Reviews Cancer, May 2008, vol. 8, No. 5, pp. 329-340.
Parekh M., et al., "As Tests Evolve and Costs of Cancer Care Rise: Reappraising Stool-based Screening for Colorectal Neoplasia," Alimentary Pharmacology & Therapeutics, 2008, vol. 27, pp. 697-712.
Park J-H., et al., "Identification of DNA Methylation Changes Associated With Human Gastric Cancer," BMC Medical Genomics, 2011, vol. 4, No. 82, pp. 1-15.
Partial European Search Report for European Application No. 19150809.2, mailed Aug. 21, 2019, 13 Pages.
Partial Supplementary European Search Report for European Application No. 14776150.6, mailed Oct. 7, 2016, 09 Pages.
Partial Supplementary European Search Report for European Application No. 15772326.3, mailed Oct. 6, 2017, 16 Pages.
Partial Supplementary European Search Report for European Application No. 15774156.2, mailed Nov. 7, 2017, 15 Pages.
Partial Supplementary European Search Report for European Application No. 16842880.3, mailed Mar. 11, 2019, 10 Pages.
Partial Supplementary European Search Report for European Application No. 17783141.9, mailed Nov. 14, 2019, 12 Pages.
Partial Supplementary European Search Report for European Application No. 17847642, mailed Oct. 16, 2020, 9 Pages.
Patent Owner's Sur-Reply in IPR2024-00459 for U.S. Pat. No. 11,634,781, filed Jun. 10, 2024, 13 Pages.
Patent Owners Preliminary Response, in IPR2024-00459 for U.S. Pat. No. 11,634,781, filed Apr. 30, 2024, 71 Pages.
Pelizzaro F., et al., "Liquid Biopsy in Hepatocellular Carcinoma: Where Are We Now?," Cancers (Basel), May 10, 2021, vol. 13, No. 9, 2274, pp. 1-42.
Perrin C., et al., "Expression of LSLCL, A New C-type Lectin, is Closely Restricted, in Bone Marrow, to Immature Neutrophils," Proceedings of the Academy of Sciences, Series III, Dec. 2001, vol. 324, No. 12, pp. 1125-1132, 10 Pages.
Petition for Inter Parties Review for U.S. Pat. No. 11,970,746, filed Aug. 20, 2024, 90 Pages.
Petition for Inter Parties Review of U.S. Pat. No. 11,634,781, dated Jan. 11, 2024, pp. 1-70 (87 Pages).
Petitioner's Reply to Patent Owner's Preliminary Reply, in IPR2024-00459 for U.S. Pat. No. 11,634,781, filed May 30, 2024, 13 Pages.
Ponomaryova A.A., et al., "Potentialities of Aberrantly Methylated Circulating DNA for Diagnostics and Post-Treatment Follow-Up of Lung Cancer Patients," Lung Cancer, 2013, vol. 81, No. 3, pp. 397-403, DOI: 10.1016/j.lungcan.2013.05.016, ISSN: 0169-5002, XP055581461, (Jan. 1, 2013).
Powell S.M., et al., "APC Mutations Occur Early During Colorectal Tumorigenesis," Letters to Nature, Sep. 17, 1992, vol. 359, pp. 235-237.
Promega: "Maxwell(R) RSC ccfDNA Plasma Kit," Technical Manual, Instructions for Use of Product AS1480, Promega Corporation, Feb. 2016, 8 Pages.
Provisional Patent Application Transmittal for for U.S. Appl. No. 61/149,581, dated Feb. 3, 2009, pp. 1-3.
Qiu X., et al., "Hypermethylation of ACP1, BMP4, and TSPYL5 in Hepatocellular Carcinoma and Their Potential Clinical Significance," Digestive Diseases and Sciences, 2016, vol. 61, No. 1, pp. 149-157, (Sep. 19, 2015).
Rakosy Z., et al., "Integrative Genomics Identifies Gene Signature Associated with Melanoma Ulceration," PLOS One, Jan. 30, 2013, vol. 8, Issue. 1 (e54958), pp. 1-14.
Ramsahoye B H., et al., "Non-CpG Methylation is Prevalent in Embryonic Stem Cells and May Be Mediated by DNA Methyltransferase 3a," Proceedings of the National Academy of Sciences of the United States of America, May 9, 2000, vol. 97, No. 10, pp. 5237-5242.
Recorded Assignment of U.S. Pat. No. 11,634,781 dated Apr. 25, 2017, pp. 1-5.
Reddi K.K., et al., "Elevated Serum Ribonuclease in Patients with Pancreatic Cancer," Proceedings of the National Academy of Sciences of the United States of America, Jul. 1976, vol. 73, No. 7, pp. 2308-2310.
Rein T., et al., "Identifying 5-Methylcytosine and Related Modifications in DNA Genomes," Nucleic Acids Research, May 15, 1998, vol. 26, No. 10, pp. 2255-2264.
Reinartz J., et al., "Massively Parallel Signature Sequencing (MPSS) as a Tool for In-Depth Quantitative Gene Expression Profiling in All Organisms," Briefings in Functional Genomics and Proteomics, Feb. 2002, vol. 1, No. 1, pp. 95-104.
Ren S., et al., "Discovery and Development of Differentially Methylated Regions in Human Papillomavirus-related Oropharyngeal Squamous Cell Carcinoma," International Journal of Cancer, Nov. 15, 2018, vol. 143, No. 10, pp. 2425-2436 (32 Pages).
Rennert G., et al., "Detecting K-Ras Mutations in Stool from Fecal Occult Blood Test Cards in Multiphasic Screening for Colorectal Cancer," Cancer Letters, 2007, vol. 253, pp. 258-264.
Request for Ex Parte Reexamination of U.S. Pat. No. 11,634,781, dated May 22, 2023, 286 Pages.

(56) References Cited

OTHER PUBLICATIONS

Response filed on Jul. 31, 2015, to Final Office Action mailed Jul. 6, 2015, for U.S. Appl. No. 14/145,082, 123 Pages.
Response filed on Oct. 6, 2023, to Non Final Office Action mailed Jul. 6, 2023, for U.S. Appl. No. 18/179,945, 11 Pages.
Rex D.K., et al., "American College of Gastroenterology Guidelines for Colorectal Cancer Screening 2008," The American Journal of Gastroenterology, Mar. 2009, vol. 104, pp. 739-750.
Robertson et al., The presence of 5-hydroxymethylcytosine at the gene promoter and not in the gene body negatively regulates gene expression. Biochem Biophys Res Commun. Jul. 22, 2011;411(1):40-3.
Ronaghi M., et al., "A Sequencing Method Based on Real-Time Pyrophosphate," Science, Jul. 17, 1998, vol. 281, No. 5375, p. 363, 365.
Ronaghi M., et al., "Real-Time DNA Sequencing using Detection of Pyrophosphate Release," Analytical Biochemistry, Nov. 1, 1996, vol. 242, No. 1, pp. 84-89.
Ross-Innes C.S., et al., "Evaluation of a Minimally Invasive Cell Sampling Device Coupled With Assessment of Trefoil Factor 3 Expression for Diagnosing Barrett's Esophagus: a Multi-center Case-control Study," PLOS Medicine, Jan. 29, 2015, vol. 12, No. 1 (el001780), pp. 1-19.
Rothberg et al., An integrated semiconductor device enabling non-optical genome sequencing. Nature. Jul. 20, 2011;475(7356):348-52.
Roux C., et al., "Polythiophene Derivatives: Smart Materials," Biotechniques, 1994, vol. 19, pp. 6-10 (5 Pages), 16(5), 812-814.
Roux, Using mismatched primer-template pairs in touchdown PCR, Biotechniques, 1994, 16(5):812-814.
Ruano G et al., "Biphasic Amplification of Very Dilute DNA Samples via 'booster' PCR," Nucleic Acids Research, Information Retrieval Ltd, Jul. 11, 1989, vol. 17, No. 13, p. 5407, ISSN: 0305-1048, XP000371657.
Salomon et al.. Methylation of mouse DNA in vivo: di- and tripyrimidine sequences containing 5-methylcytosine. Biochim Biophys Acta. Apr. 15, 1970;204(2):340-51.
Santini J., et al., "Characterization, Quantification, and Potential Clinical Value of the Epidermal Growth Factor Receptor in Head and Neck Squamous Cell Carcinomas," Head & Neck, Mar./Apr. 1991, vol. 13, No. 2, pp. 132-139.
Sato F., et al., "Aberrant Methylation of the HPP1 Gene in Ulcerative Colitis-associated Colorectal Carcinoma," Cancer Research, Dec. 1, 2002, vol. 62, pp. 6820-6822.
Sato F., et al., "Hypermethylation of The p14(ARF) Gene in Ulcerative Colitis-associated Colorectal Carcinogenesis1," Cancer Research, Feb. 15, 2002, vol. 62, No. 4, pp. 1148-1151.
Sawas T., et al., "Eradication of Dysplasia Only Without Eradicating Intestinal Metaplasia is Associated With Higher Risk of Advance Neoplasia Recurrence: Meta-analysis," Abstract 8, Gastroenterology, 2018, vol. 15, No. 6, Supplement. 1, p. S-3 (2 Pages).
Schmidt B., et al., "SHOX2 DNA Methylation is a Biomarker for the Diagnosis of Lung Cancer Based on Bronchial Aspirates," BMC Cancer, Nov. 3, 2010, vol. 10, Article No. 600, 9 Pages.
Schouten et al., Relative quantification of 40 nucleic acid sequences by multiplex ligation-dependent probe amplification, Nucleic Acids Research, 2002, 30(12): e57. 13 pages.
Schroy P.C. III., et al., "Patient Perceptions of Stool-Based DNA Testing for Colorectal Cancer Screening," American Journal of Preventive Medicine, 2005, vol. 28, No. 2, pp. 208-214.
Schuebel K.E., et al., "Comparing the DNA Hypermethylome With Gene Mutations in Human Colorectal Cancer," PLOS Genetics, Sep. 2007, vol. 3, No. 9, pp. 1709-1723.
Schuuring E., et al., "Characterization of the EMS1 Gene and its Product, Human Cortactin," Cell Adhesion and Communication, 1998, vol. 6, No. 2-3, pp. 185-209 (26 Pages).
Schuuring E., et al., "Identification and Cloning of Two Overexpressed Genes, U21831/PRAD1 and EMS1, Within the Amplified Chromosome 11q13 Region in Human Carcinomas," Oncogene, Feb. 1992, vol. 7, No. 2, pp. 355-361 (10 Pages).
Science Daily: "Stool DNA Testing for Colon Cancer," Exact Sciences and Mount Sinai School of Medicine, Dec. 13, 2006, 3 Pages, [Retrieved on Jan. 9, 2024] Retrieved from URL: https://www.sciencedaily.eom/releases/2006/12/061213104115.htm#.
Selvin P.R., "Fluorescence Resonance Energy Transfer," Methods in Enzymology, 1995, vol. 246, pp. 300-334, 36 Pages.
Shao G., et al., "Formyl Peptide Receptor Ligands Promote Wound Closure in Lung Epithelial Cells," American Journal of Respiratory Cell and Molecular Biology, Mar. 2011, vol. 44, No. 3, pp. 264-269.
Sharaf R.V., et al., "Comparative Effectiveness and Cost-effectiveness of Screening Colonoscopy vs. Sigmoidoscopy and Alternative Strategies," The American Journal of Gastroenterology, Jan. 2013, vol. 108, pp. 120-132.
Shastri Y.M., et al., "Comparison of an Established Simple Office-based Immunological FOBT With Fecal Tumor Pyruvate Kinase Type M2 (M2-PK) for Colorectal Cancer Screening: Prospective Multicenter Study," American Journal of Gastroenterology, Jun. 2008, vol. 103, No. 6, pp. 1496-1504 (10 Pages).
Shen B., et al., "Multiple But Dissectible Functions of FEN-1 Nucleases in Nucleic Acid Processing, Genome Stability and Diseases," BioEssays, Jul. 2005, vol. 27, No. 7, pp. 717-729.
Shen J., et al., "Integrative Epigenomic and Genomic Filtering for Methylation Markers in Hepatocellular Carcinomas," BMC Medical Genomics, Jun. 10, 2015, vol. 8, No. 28, pp. 1-12.
Shen L., et al., "Integrated Genetic and Epigenetic Analysis Identifies Three Different Subclasses of Colon Cancer," Proceedings of the National Academy of Sciences of the United States of America, Nov. 20, 2007, vol. 104, No. 47, pp. 18654-18659.
Shendure J., et al., "Accurate Multiplex Polony Sequencing of an Evolved Bacterial Genome," Science, Sep. 9, 2005, vol. 309, No. 5741, pp. 1728-1732 (9 Pages).
Shendure J., et al., "Next-Generation DNA Sequencing," Nature Biotechnology, Oct. 2008, vol. 26, No. 10, pp. 1135-1145.
Shi L., et al., "Up-Regulation of miR-146a Increases the Sensitivity of Non-Small Cell Lung Cancer to DDP by Downregulating Cyclin J," BMC Cancer, Feb. 15, 2017, vol. 17, No. 1, Article No. 138, 14 Pages.
Shimada S., et al., "Pancreatic Elastase IIIA and Its Variants Are Expressed in Pancreatic Carcinoma Cells," International Journal of Molecular Medicine, Spandidos Publications, GR, Nov. 1, 2002, vol. 10, pp. 599-603, ISSN: 1107-3756, XP008135412.
Shire A., et al., "BMP3 is Hypermethylated and May Function as a Tumor Suppressor in Cholangiocarcinoma," Cancer Research, May 1, 2008, vol. 68, Supplementary 9, Abstract 4282, 2 Pages.
Sidransky D., et al., "Identification of Ras Oncogene Mutations in the Stool of Patients With Curable Colorectal Tumors," Science, Apr. 3, 1992, vol. 256, pp. 102-105, (5 Pages).
Siegel R., et al., "Cancer Statistics, 2013," CA: A Cancer Journal for Clinicians, Jan. 2013, vol. 63, No. 1, pp. 11-30.
Simon J.B., "Occult Blood Screening for Colorectal Carcinoma: A Critical Review," Gastroenterology, Mar. 1985, vol. 88, No. 3, pp. 820-837.
Siravegna G., et al., "How Liquid Biopsies can Change Clinical Practice in Oncology," Annals of Oncology, Oct. 1, 2019, vol. 30, No. 10, pp. 1580-1590.
Sjoblom T., et al., "The Consensus Coding Sequences of Human Breast and Colorectal Cancers," Science, Oct. 13, 2006, vol. 314, No. 5797, pp. 268-274.
Sloane M A., et al., "Epigenetic Inactivation of the Candidate Tumor Suppressor USP44 is a Frequent and Early Event in Colorectal Neoplasia," Epigenetics, Aug. 2014, vol. 9, No. 8, pp. 1092-1100.
Sommer R., "Minimal Homology Requirements for PCR Primers," Nucleic Acids Research, 1989, vol. 17, No. 16, p. 6749.
Soussi T., et al., "p53 Mutation Heterogeneity in Cancer," Biochemical and Biophysical Research Communications, Jun. 10, 2005, vol. 331, No. 3, pp. 834-842.
Spitzwieser M., et al., "Promoter Methylation Patterns of ABCB1, ABCC1 and ABCG2 in Human Cancer Cell Lines, Multidrug-resistant Cell Models and Tumor, Tumor-adjacent and Tumor-distant Tissues From Breast Cancer Patients," Oncotarget, Sep. 28, 2016, vol. 7, No. 45, pp. 73347-73369.(Nov. 8, 2016).

(56) References Cited

OTHER PUBLICATIONS

Sriraksa R., et al., "Aberrant DNA Methylation at Genes Associated With a Stem Cell-like Phenotype in Cholangiocarcinoma Tumors," Cancer Prevention Research, (Phila), Dec. 2013, vol. 6, No. 12, pp. 1348-1355.
Stephens P., et al., "A Screen of the Complete Protein Kinase Gene Family Identifies Diverse Patterns of Somatic Mutations in Human Breast Cancer," Nature Genetics, Jun. 2005, vol. 37, No. 6, pp. 590-592(5 Pages).
Straub J., et al., "Base5, A Versatile, Highly Integrated High-throughput Methylation Profiling for Methylation Specific PCR Based Marker Identification Applied to Colorectal Cancer," Clinical Cancer Research, Oct. 2007, vol. 13, Issue 19, Supplement A61, 4 Pages.
Strausberg R.L., et al., "Generation and Initial Analysis of More Than 15,000 Full-Length Human and Mouse cDNA Sequences," Proceedings of the National Academy of Sciences, USA, Dec. 24, 2002, vol. 99, No. 26, pp. 16899-16903.
Stryer, Fluorescence energy transfer as a spectroscopic ruler, Annu Rev Biochem. 1978;47:819-46.
Sun X., et al., "Long Non-coding RNA Hotair Regulates Cyclin J Via Inhibition of MicroRNA-205 Expression in Bladder Cancer," Cell Death & Disease, Oct. 15, 2015, vol. 6, pp. 1-9, el907.
Sun X-J., et al., "An Integrated Analysis of Genome-wide DNA Methylation and Gene Expression Data in Hepatocellular Carcinoma," FEBS Open Bio, May 30, 2018, vol. 8, No. 7, pp. 1093-1103.
Supplementary Partial European Search Report for European Application No. 14776150.6, dated Sep. 29, 2016, 7 Pages.
Swift-Scanlan T., et al., "Two-Color Quantitative Multiplex Methylation-Specific PCR," Biotechniques, Feb. 2006, vol. 40, No. 2, pp. 210-218.
Tagore K.S., et al., "Review Article: The Evolution to Stool DNA Testing for Colorectal Cancer," Alimentary Pharmacology & Therapeutics, 2004, vol. 19, pp. 1225-1233.
Takahashi T., et al., "Estimation of the Fraction of Cancer Cells in a Tumor DNA Sample Using DNA Methylation," PLOS One, Dec. 2, 2013, vol. 8, No. 12: e82302, pp. 1-10.
Takano N., et al., "CCNJ Detected by Triple Combination Array Analysis as a Tumor-related Gene of Hepatocellular Carcinoma," International Journal of Oncology, May 2015, vol. 46, No. 5, pp. 1963-1970.
Taylor W.R., et al., "Discovery of Novel DNA Methylation Markers for the Detection of Colorectal Neoplasia: Selection by Methylome-Wide Analysis," Abstract 109, Gastroenterology, May 1, 2014, vol. 146, No. 5, p. S-30.
Third Office Action for Chinese Application No. 201480015389.5, mailed Mar. 30, 2018, 9 Pages.
Toth K., et al., "Detection of Methylated SEPT9 in Plasma is a Reliable Screening Method for Both Left- and Right-sided Colon Cancers," PLoS One, Sep. 2012, vol. 7, No. 9, pp. 1-7, e46000.
Triglia et al., A procedure for in vitro amplification of DNA segments that lie outside the boundaries of known sequences, Nucleic Acids Res., 1988, 16:8186.
Tsou J.A., et al., "Identification of a Panel of Sensitive and Specific DNA Methylation Markers for Lung Adenocarcinoma," Molecular Cancer, Oct. 29, 2007, vol. 6, No. 70, pp. 1-13.
Tsumagari K., et al., "Dna Methylation and Differentiation: Hox Genes in Muscle Cells ," Epigenetics & Chromatin, Aug. 2, 2013, vol. 6, No. 1 (25), 17 Pages.
Turcatti G., et al., "A New Class of Cleavable Fluorescent Nucleotides: Synthesis and Optimization as Reversible Terminators for DNA Sequencing by Synthesis," Nucleic Acids Research, Mar. 2008, vol. 36, No. 4, Article No. e25, 13 pages.
Tureci O., et al., "Humoral Immune Responses of Lung Cancer Patients Against Tumor Antigen NY-ESO-1," Cancer Letters, May 8, 2006, vol. 236, No. 1, pp. 64-71.
Turgeon D.K., et al., "Fecal DNA-Based Detection of Colorectal Neoplasia," Current colorectal cancer reports, Oct. 2007, vol. 3, No. 4, pp. 171-177.
Turner H.E., et al., "Role of Matrix Metalloproteinase 9 in Pituitary Tumor Behavior," Journal of Clinical Endocrinology & Metabolism, Aug. 2000, vol. 85, No. 8, pp. 2931-2935.
Umu S.U., et al., "A Comprehensive Profile of Circulating RNAs in Human Serum," RNA Biology, Feb. 1, 2018, vol. 15, No. 2, pp. 242-250 (10 Pages).
Vancompernolle S.E., et al., "Expression and Function of Formyl Peptide Receptors on Human Fibroblast Cells," Journal of Immunology, Aug. 15, 2003, vol. 171, No. 4, pp. 2050-2056 (8 Pages).
Venturutti L., et al., "MiR-16 Mediates Trastuzumab and Lapatinib Response in ErbB-2-Positive Breast and Gastric Cancer via Its Novel Targets CCNJ and FUBP1," Oncogene, Dec. 1, 2016, vol. 35, No. 48, pp. 6189-6202 (30 Pages).
Vernon S.W., et al., "Participation in Colorectal Cancer Screening: A Review," Journal of the National Cancer Institute, Oct. 1, 1997, vol. 89, No. 19, pp. 1406-1422.
Vilkin A., et al., "Performance Characteristics and Evaluation of an Automated-Developed and Quantitative, Immunochemical Fecal Occult Blood Screening Test," The American Journal of Gastroenterology, Nov. 2005, vol. 100, No. 11, pp. 2519-2525.
Villa E., et al., "Identification of Subjects at Riskfor Colorectal Carcinoma through a Test Based on K-Ras Determination in the Stool," Gastroenterology, May 1996, vol. 110, pp. 1346-1353.
Villar-Garea A., et al., "DNA Demethylating Agents and Chromatin-Remodelling Drugs: Which, How and Why?," Current Drug Metabolism, Feb. 2003, vol. 4, No. 1, pp. 11-31.
Vincent A., et al., "Pancreatic Cancer," Lancet, Aug. 13, 2011, vol. 378, No. 9791, pp. 607-620 (28 Pages).
Vogelstein B., et al., "Cancer Genome Landscapes," Science, Mar. 29, 2013, vol. 339, No. 6127, pp. 1546-1558, (32 Pages).
Vogelstein et al. Digital PCR. Proc Natl Acad Sci USA. 1999;96; 9236-41.
Wang H-D., et al., "DNA Methylation Study of Fetus Genome Through a Genome-Wide Analysis," BMC Medical Genomics, Apr. 15, 2014, vol. 7, No. 18, 8 Pages.
Wang R.N., et al., "Bone Morphogenetic Protein (BMP) Signaling in Development and Human Diseases," Genes & Diseases, Sep. 2014, vol. 1, No. 1, pp. 87-105.
Wang W., et al., "Crosstalk to Stromal Fibroblasts Induces Resistance of Lung Cancer to Epidermal Growth Factor Receptor Tyrosine Kinase Inhibitors," Clinical Cancer Research, Nov. 1, 2009, vol. 15, No. 21, pp. 6630-6638.
Wang X., et al., "Aberrant DNA Methylation: Implications in Racial Health Disparity," PLoS ONE, Apr. 25, 2016, vol. 11, No. 4:e0153125, 16 Pages.
Wang Y., et al., "Usefulness of p53 Gene Mutations in the Supernatant of Bile for Diagnosis of Biliary Tract Carcinoma: Comparison with K-ras Mutation," Journal of Gastroenterology, 2002, vol. 37, pp. 831-839.
Wang Z-R., et al., "Validation of DAB2IP Methylation and Its Relative Significance in Predicting Outcome in Renal Cell Carcinoma," Oncotarget, May 24, 2016, vol. 7, No. 21, pp. 31508-31519.
Wasserkort R., et al., "Aberrant Septin 9 DNA Methylation in Colorectal Cancer is Restricted to a Single CpG Island," BMC Cancer, Aug. 30, 2013, vol. 13, No. 398, pp. 1-11.
Watanabe T., "RUNX3 Copy Number Predicts the Development of UC-Associated Colorectal Cancer," International Journal of Oncology, 2011, vol. 38, pp. 201-207.
Weisenberger D.J., et al., "Comprehensive DNA Methylation Analysis on the Illumina Infinium Assay Platform," Illumina, Jan. 1, 2010, 4 pages, [Retrieved on Dec. 4, 2020] Retrieved from URL: https://emea.illumina.com/content/dam/illumina-marketing/documents/products/appnotes/appnote_dna_methylation_a nalysis_infinium.pdf.
White V., et al., "Colorectal Cancer: Prevention and Early Diagnosis," Medicine, 2007, vol. 35, No. 6, pp. 297-301.
Whitney D., et al., "Enhanced Retrieval of DNA from Human Fecal Samples Results in Improved Performance of Colorectal Cancer Screening Test," Journal of Molecular Diagnostics, Nov. 2004, vol. 6, No. 4, pp. 386-395.
Williams R., et al., "Amplification of Complex Gene Libraries by Emulsion PCR," Nature Methods, Jul. 2006, vol. 3, No. 7, pp. 545-550.

(56) References Cited

OTHER PUBLICATIONS

Wilm M., et al., "Femtomole Sequencing of Proteins From Polyacrylamide Gels by Nano-Electrospray Mass Spectrometry," Nature, Feb. 1, 1996, vol. 379, No. 6564, pp. 466-469.
WO Y-Y.P., et al., "Sequencing, Cloning, and Expression of Human Red Cell-Type Acid Phosphatase, A Cytoplasmic Phosphotyrosyl Protein Phosphatase," Journal of Biological Chemistry, May 25, 1992, vol. 267, No. 15, pp. 10856-10865.
Wood L.D., et al., "Pathology and Molecular Genetics of Pancreatic Neoplasms," The Cancer Journal, 2012, vol. 18, No. 6, pp. 492-501, (21 Pages).
Wood L.D., et al., "The Genomic Landscapes of Human Breast and Colorectal Cancers," Science, Nov. 16, 2007, vol. 318, No. 5853, pp. 1108-1113(6 Pages).
Woodcock D.M., et al., "The Majority of Methylated Deoxycytidine in Human DNA are Not in the CpG Dinucleotide," Biochemical and Biophysical Research Communications, Jun. 15, 1987, vol. 145, No. 2, pp. 888-894.
Wrangle J., et al., "Functional Identification of Cancer-Specific Methylation of CDO1, HOXA9, and TAC1 for the Diagnosis of Lung Cancer," Clinical Cancer Research, Apr. 1, 2014, vol. 20, No. 7, pp. 1856-1864 (16 Pages).
Wu et al., The ligation amplification reaction (LAR)-amplification of specific DNA sequences using sequential rounds of template-dependent ligation. Genomics. May 1989;4(4):560-9.
Wu X., et al., "Analysis of Methylation Profiling Data of Hyperplasia and Primary and Metastatic Endometrial Cancers," European Journal of Obstetrics & Gynecology and Reproductive Biology, Oct. 2017, vol. 217, pp. 161-166.
Wu X., et al., "Detection of Colorectal Cancer Using a Simplified SEPT9 Gene Methylation Assay Is a Reliable Method for Opportunistic Screening," Journal of Molecular Diagnostics, Jul. 2016, vol. 18, No. 4, pp. 535-545.
Xiao W., et al., "Quantitative Detection of Methylated NDRG4 gene as a Candidate Biomarker for Diagnosis of Colorectal Cancer," Oncology Letters, 2015, vol. 9, pp. 1383-1387.
Yamada H., et al., "Fluorometric Identification of 5-methylcytosine Modification in Dna: Combination of Photosensitized Oxidation and Invasive Cleavage," Bioconjugate Chemistry, Jan. 2008, vol. 19, No. 1, pp. 20-23.
Yano M., et al., "Aberrant Promoter Methylation of Human DAB2 Interactive Protein (hDAB2IP) Gene in Lung Cancers," International Journal of Cancer, 2005, vol. 113, pp. 59-66.
Yi J.M., et al., "Genomic and Epigenomic Integration Identifies a Prognostic Signature in Colon Cancer," Clinical Cancer Research, Mar. 15, 2011, vol. 17, No. 6, pp. 1535-1545 (16 Pages).
Yi J.M., et al., "Novel Methylation Biomarker Panel for the Early Detection of Pancreatic Cancer," Clinical Cancer Research, Dec. 1, 2013, vol. 19, No. 23, pp. 6544-6555.
Yoo C.B., et al., "Epigenetic Therapy of Cancer: Past, Present and Future," Nature Reviews Drug Discovery, Jan. 2006, vol. 5, No. 1, pp. 37-50.
Young G.P., et al., "New Stool Screening Tests for Colorectal Cancer," Digestion, 2007, vol. 76, pp. 26-33 (8 Pages).
Yu H., et al., "Significance of Combined Detection of LunX mRNA and Tumor Markers in Diagnosis of Lung Carcinoma," Chinese Journal of Cancer Research, Feb. 2014, vol. 26, No. 1, pp. 89-94.
Zeschnigk M., et al., "Imprinted Segments in the Human Genome: Different DNA Methylation Patterns in the Prader-willi/angelman Syndrome Region as Determined by the Genomic Sequencing Method," Human Molecular Genetics, Mar. 1997, vol. 6, No. 3, pp. 387-395.
Zha T-Z., et al., "Overexpression of HOXA1 Correlates with Poor Prognosis in Patients With Hepatocellular Carcinoma," Tumor Biology, Dec. 2012, vol. 33, No. 6, pp. 2125-2134, Electronic Published Aug. 4, 2012.
Zhang X., et al., "Low Expression of DAB2IP Contributes to Malignant Development and Poor Prognosis in Hepatocellular Carcinoma," Journal of Gastroenterology and Hepatology, Jun. 2012, vol. 27, No. 6, pp. 1117-1125.
Zhang Z., et al., "Promoter Hypermethylation-mediated Inactivation of LRRC4 in Gliomas," BMC Molecular Biology, Biomed Central LTD, GB, Nov. 3, 2008, vol. 9, No. 99, 9 Pages.
Zhou D., et al., "Massively Parallel Signature Sequencing," Methods in Molecular Biology, 2006, vol. 331, pp. 285-311.
Zong L., et al., "Establishment of a DNA Methylation Marker to Evaluate Cancer Cell Fraction in Gastric Cancer," Gastric Cancer, 2016, vol. 19, pp. 361-369.
Zou H., et al., "Sensitive Quantification of Methylated Markers With a Novel Methylation Specific Technology," Clinical Chemistry, 2010, vol. 56, No. 6, Abstract D-144, p.A199 (1 page).
Zou H., et al., "Quantification of Methylated Markers With a Multiplex Methylation-specific Technology," Clinical Chemistry, Feb. 2012, vol. 58, No. 2, pp. 375-383.
Zou H., et al., "T1105: A Sensitive Method to Scan Gene Mutations in Stool: Relevance to Detection of Gastrointestinal Neoplasia," Gastroenterology, Apr. 2008, vol. 134, No. 4, Supplement A-484, 1 Page.
Zou H., et al., "T2037: Quantitative Stool DNA Testing for Detection of Both Colorectal Cancer and Advanced Adenoma," Gastroenterology, May 2009, vol. 136, No. 5, Supplement A-625, 2 Pages.
Kisiel J.B., et al., "Analysis of DNA Methylation at Specific Loci in Stool Samples Detects Colorectal Cancer and High-Grade Dysplasia in Patients With Inflammatory Bowel Disease", Clinical Gastroenterology and Hepatology, W.B. Saunders, vol. 17, No. 5, May 15, 2018, pp. 914-921.e5, XP085637775, ISSN: 1542-3565, DOI: 10.1016/J.CGH.2018.05.004, table 1, abstract, the whole document.
Brikun I., et al., "A Panel of DNA Methylation Markers for the Detection of Prostate Cancer from FV and DRE Urine DNA", Clinical Epigenetics, Biomed Central LTD, London, UK, vol. 10, No. 1, Jul. 3, 2018, 15 Pages, XP021258123, ISSN: 1868-7075, DOI: 10.1186/S13148-018-0524-X, Abstract, Tables 2, 3.
Mafficini A., et al., "Genetics and Epigenetics of Gastroenteropancreatic Neuroendocrine Neoplasms", Endocrine Reviews, vol. 40, No. 2, Jan. 17, 2019, pp. 506-536, XP093264023, US, ISSN: 0163-769X, DOI:10.1210/er.2018-00160, p. 517, col. 2, Paragraph 3-p. 519, col. 2, Paragraph 2.
Natale F., et al., "Deciphering DNA Methylation Signatures of Pancreatic Cancer and Pancreatitis", Clinical Epigenetics, vol. 11, No. 132, 2019, 12 Pages.
Nawaz I., et al., "Development of a Multiplex Methylation Specific PCR Suitable for (Early) Detection of Non-Small Cell Lung Cancer", Epigenetics, vol. 9, No. 8, Jun. 17, 2014, pp. 1138-1148, XP055664211, DOI: 10.4161/epi.29499, Abstract, Figure 1, Table 2.
Supplementary Partial European Search Report for European Application No. 21800508.0, dated Apr. 4, 2025, 14 Pages.
Wang X.X., et al., "Large-Scale DNA Methylation Expression Analysis Across 12 Solid Cancers Reveals Hypermethylation in the Calcium-Signaling Pathway", Oncotarget, vol. 8, No. 7, Feb. 1, 2017, pp. 11868-11876, 20 Pages, XP093264028, United States ISSN: 1949-2553, DOI: 10.18632/oncotarget.14417, Abstract, Tables S1, S8, p. 11869, col. 2, Paragraph 2.

\* cited by examiner

SEQUENCE LISTING

<160> NUMBER OF SEQ ID NOS: 50

<210> SEQ ID NO 1
<211> LENGTH: 27
<212> TYPE: DNA
<213> ORGANISM: Artificial Sequence
<220> FEATURE:
<223> OTHER INFORMATION: synthetic

<400> SEQUENCE: 1
tggcggcgga ggtagtttta aagatac                                    27

<210> SEQ ID NO 2
<211> LENGTH: 25
<212> TYPE: DNA
<213> ORGANISM: Artificial Sequence
<220> FEATURE:
<223> OTHER INFORMATION: synthetic

<400> SEQUENCE: 2
tcgatcccga ccgaaaacta acgtc                                      25

<210> SEQ ID NO 3
<211> LENGTH: 23
<212> TYPE: DNA
<213> ORGANISM: Artificial Sequence
<220> FEATURE:
<223> OTHER INFORMATION: synthetic

<400> SEQUENCE: 3
gacgtttgtc gtcgggttcg ttc                                        23

<210> SEQ ID NO 4
<211> LENGTH: 24
<212> TYPE: DNA
<213> ORGANISM: Artificial Sequence
<220> FEATURE:
<223> OTHER INFORMATION: synthetic

<400> SEQUENCE: 4
aaaaaccctc cgctaccact tcgc                                       24

<210> SEQ ID NO 5
<211> LENGTH: 25
<212> TYPE: DNA
<213> ORGANISM: Artificial Sequence
<220> FEATURE:
<223> OTHER INFORMATION: synthetic

<400> SEQUENCE: 5
ttgagatgtt gggtgaaggc gattc                                      25

<210> SEQ ID NO 6
<211> LENGTH: 26
<212> TYPE: DNA
<213> ORGANISM: Artificial Sequence
<220> FEATURE:
<223> OTHER INFORMATION: synthetic

<400> SEQUENCE: 6
cgctaacgcg aaaaaataat tcgacg                                     26

<210> SEQ ID NO 7
<211> LENGTH: 28
<212> TYPE: DNA
<213> ORGANISM: Artificial Sequence
<220> FEATURE:
<223> OTHER INFORMATION: synthetic

<400> SEQUENCE: 7
cggttttatt tattatgatt cgtagcgg                28

<210> SEQ ID NO 8
<211> LENGTH: 24
<212> TYPE: DNA
<213> ORGANISM: Artificial Sequence
<220> FEATURE:
<223> OTHER INFORMATION: synthetic

<400> SEQUENCE: 8
cgactaccct aaacaacgca tcgc                    24

<210> SEQ ID NO 9
<211> LENGTH: 17
<212> TYPE: DNA
<213> ORGANISM: Artificial Sequence
<220> FEATURE:
<223> OTHER INFORMATION: synthetic

<400> SEQUENCE: 9
gcgcgtagcg gcgtttc                            17

<210> SEQ ID NO 10
<211> LENGTH: 19
<212> TYPE: DNA
<213> ORGANISM: Artificial Sequence
<220> FEATURE:
<223> OTHER INFORMATION: synthetic

<400> SEQUENCE: 10
cccatatcgc ccgacgtaa                          19

<210> SEQ ID NO 11
<211> LENGTH: 34
<212> TYPE: DNA
<213> ORGANISM: Artificial Sequence
<220> FEATURE:
<223> OTHER INFORMATION: synthetic

<400> SEQUENCE: 11
ttatattttt cgttttagt aatttcgcgt tagc           34

<210> SEQ ID NO 12
<211> LENGTH: 23
<212> TYPE: DNA
<213> ORGANISM: Artificial Sequence
<220> FEATURE:
<223> OTHER INFORMATION: synthetic

<400> SEQUENCE: 12 gaaacccgc cgaaacattt cga                      23

<210> SEQ ID NO 13
<211> LENGTH: 23
<212> TYPE: DNA
<213> ORGANISM: Artificial Sequence
<220> FEATURE:
<223> OTHER INFORMATION: synthetic

<400> SEQUENCE: 13
gtttaatttt cggtttcgtc gtc                     23

<210> SEQ ID NO 14
<211> LENGTH: 18
<212> TYPE: DNA
<213> ORGANISM: Artificial Sequence
<220> FEATURE:
<223> OTHER INFORMATION: synthetic

<400> SEQUENCE: 14
cgctacgaaa cactccga                                                 18

<210> SEQ ID NO 15
<211> LENGTH: 21
<212> TYPE: DNA
<213> ORGANISM: Artificial Sequence
<220> FEATURE:
<223> OTHER INFORMATION: synthetic

<400> SEQUENCE: 15
cggttttcgt tcgttttttc g                                             21

<210> SEQ ID NO 16
<211> LENGTH: 18
<212> TYPE: DNA
<213> ORGANISM: Artificial Sequence
<220> FEATURE:
<223> OTHER INFORMATION: synthetic

<400> SEQUENCE: 16
ccgccttcta cgcgacta                                                 18

<210> SEQ ID NO 17
<211> LENGTH: 30
<212> TYPE: DNA
<213> ORGANISM: Artificial Sequence
<220> FEATURE:
<223> OTHER INFORMATION: synthetic

<400> SEQUENCE: 17
ggggcgttgt ttaacgtatc gaatagttac                                    30

<210> SEQ ID NO 18
<211> LENGTH: 30
<212> TYPE: DNA
<213> ORGANISM: Artificial Sequence
<220> FEATURE:
<223> OTHER INFORMATION: synthetic

<400> SEQUENCE: 18
gctacaaacc ctctacccac ctaaatcgac                                    30

<210> SEQ ID NO 19
<211> LENGTH: 25
<212> TYPE: DNA
<213> ORGANISM: Artificial Sequence
<220> FEATURE:
<223> OTHER INFORMATION: synthetic

<400> SEQUENCE: 19
ttttagtaag ggtcgtattg gacgt                                         25

<210> SEQ ID NO 20
<211> LENGTH: 27
<212> TYPE: DNA
<213> ORGANISM: Artificial Sequence
<220> FEATURE:
<223> OTHER INFORMATION: synthetic

<400> SEQUENCE: 20
caaaaactcg ctaacacgaa actcccg                                    27

<210> SEQ ID NO 21
<211> LENGTH: 16
<212> TYPE: DNA
<213> ORGANISM: Artificial Sequence
<220> FEATURE:
<223> OTHER INFORMATION: synthetic

<400> SEQUENCE: 21
gttcgtcgtt cgggtc                                                16

<210> SEQ ID NO 22
<211> LENGTH: 19
<212> TYPE: DNA
<213> ORGANISM: Artificial Sequence
<220> FEATURE:
<223> OTHER INFORMATION: synthetic

<400> SEQUENCE: 22
tccttcgcta ccgaaaacg                                             19

<210> SEQ ID NO 23
<211> LENGTH: 19
<212> TYPE: DNA
<213> ORGANISM: Artificial Sequence
<220> FEATURE:
<223> OTHER INFORMATION: synthetic

<400> SEQUENCE: 23
gtttcgttac ggattcgtc                                             19

<210> SEQ ID NO 24
<211> LENGTH: 19
<212> TYPE: DNA
<213> ORGANISM: Artificial Sequence
<220> FEATURE:
<223> OTHER INFORMATION: synthetic

<400> SEQUENCE: 24
tactcgtaaa aaacgccg                                              19

<210> SEQ ID NO 25
<211> LENGTH: 19
<212> TYPE: DNA
<213> ORGANISM: Artificial Sequence
<220> FEATURE:
<223> OTHER INFORMATION: synthetic

<400> SEQUENCE: 25
ggttcggttg tcgtagcgc                                             19

<210> SEQ ID NO 26
<211> LENGTH: 20
<212> TYPE: DNA
<213> ORGANISM: Artificial Sequence
<220> FEATURE:
<223> OTHER INFORMATION: synthetic

<400> SEQUENCE: 26
ccgaccgtaa tcctcgacga                                            20

<210> SEQ ID NO 27

<211> LENGTH: 24
<212> TYPE: DNA
<213> ORGANISM: Artificial Sequence
<220> FEATURE:
<223> OTHER INFORMATION: synthetic

<400> SEQUENCE: 27
gttaatttcg cgaggtaggc gacg                                              24

<210> SEQ ID NO 28
<211> LENGTH: 33
<212> TYPE: DNA
<213> ORGANISM: Artificial Sequence
<220> FEATURE:
<223> OTHER INFORMATION: synthetic

<400> SEQUENCE: 28
cgtaatacaa tactcttata tattaacgcc gct                                    33

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
tgtggaatcg gggtttgtgt tcgc                                              24

<210> SEQ ID NO 30
<211> LENGTH: 25
<212> TYPE: DNA
<213> ORGANISM: Artificial Sequence
<220> FEATURE:
<223> OTHER INFORMATION: synthetic

<400> SEQUENCE: 30
cccacccaac acaaaaaatc cgacg                                             25

<210> SEQ ID NO 31
<211> LENGTH: 24
<212> TYPE: DNA
<213> ORGANISM: Artificial Sequence
<220> FEATURE:
<223> OTHER INFORMATION: synthetic

<400> SEQUENCE: 31
ggagtttatt ttgggaagag tcgc                                              24

<210> SEQ ID NO 32
<211> LENGTH: 20
<212> TYPE: DNA
<213> ORGANISM: Artificial Sequence
<220> FEATURE:
<223> OTHER INFORMATION: synthetic

<400> SEQUENCE: 32
ccccgcaatc gaaacaaacg                                                   20

<210> SEQ ID NO 33
<211> LENGTH: 29
<212> TYPE: DNA
<213> ORGANISM: Artificial Sequence
<220> FEATURE:
<223> OTHER INFORMATION: synthetic

<400> SEQUENCE: 33
gggtagagaa tatatagtga agagtacgg                                29

<210> SEQ ID NO 34
<211> LENGTH: 27
<212> TYPE: DNA
<213> ORGANISM: Artificial Sequence
<220> FEATURE:
<223> OTHER INFORMATION: synthetic

<400> SEQUENCE: 34
actaaatcac ctcctactac taacgct                                  27

<210> SEQ ID NO 35
<211> LENGTH: 19
<212> TYPE: DNA
<213> ORGANISM: Artificial Sequence
<220> FEATURE:
<223> OTHER INFORMATION: synthetic

<400> SEQUENCE: 35
gcgacgtagt cgtcgttgt                                           19

<210> SEQ ID NO 36
<211> LENGTH: 19
<212> TYPE: DNA
<213> ORGANISM: Artificial Sequence
<220> FEATURE:
<223> OTHER INFORMATION: synthetic

<400> SEQUENCE: 36
ccaacgcgaa aaaacgcg                                            19

<210> SEQ ID NO 37
<211> LENGTH: 25
<212> TYPE: DNA
<213> ORGANISM: Artificial Sequence
<220> FEATURE:
<223> OTHER INFORMATION: synthetic

<400> SEQUENCE: 37
gtttcgttcg aaaggtaggg gttcg                                    25

<210> SEQ ID NO 38
<211> LENGTH: 25
<212> TYPE: DNA
<213> ORGANISM: Artificial Sequence
<220> FEATURE:
<223> OTHER INFORMATION: synthetic

<400> SEQUENCE: 38
cgaatctccc gaaaaataaa acgtt                                    25

<210> SEQ ID NO 39
<211> LENGTH: 19
<212> TYPE: DNA
<213> ORGANISM: Artificial Sequence
<220> FEATURE:
<223> OTHER INFORMATION: synthetic

<400> SEQUENCE: 39
tcggagtcga gtttagcgc                                           19

<210> SEQ ID NO 40
<211> LENGTH: 24
<212> TYPE: DNA

```
<213> ORGANISM: Artificial Sequence
<220> FEATURE:
<223> OTHER INFORMATION: synthetic

<400> SEQUENCE: 40
cgaaatcgaa aaacaaaaa ccgc                                      24

<210> SEQ ID NO 41
<211> LENGTH: 19
<212> TYPE: DNA
<213> ORGANISM: Artificial Sequence
<220> FEATURE:
<223> OTHER INFORMATION: synthetic

<400> SEQUENCE: 41
gtcgtcgttc gagagggta                                           19

<210> SEQ ID NO 42
<211> LENGTH: 22
<212> TYPE: DNA
<213> ORGANISM: Artificial Sequence
<220> FEATURE:
<223> OTHER INFORMATION: synthetic

<400> SEQUENCE: 42
cgaacaaaaa cgaacgaacg aa                                       22

<210> SEQ ID NO 43
<211> LENGTH: 20
<212> TYPE: DNA
<213> ORGANISM: Artificial Sequence
<220> FEATURE:
<223> OTHER INFORMATION: synthetic

<400> SEQUENCE: 43
cgccgaggcg gtttttttgcg                                         20

<210> SEQ ID NO 44
<211> LENGTH: 21
<212> TYPE: DNA
<213> ORGANISM: Artificial Sequence
<220> FEATURE:
<223> OTHER INFORMATION: synthetic

<400> SEQUENCE: 44
ccacggacgg ttcgtttatc g                                        21

<210> SEQ ID NO 45
<211> LENGTH: 20
<212> TYPE: DNA
<213> ORGANISM: Artificial Sequence
<220> FEATURE:
<223> OTHER INFORMATION: synthetic

<400> SEQUENCE: 45
cgccgaggcg gcgttcgcga                                          20

<210> SEQ ID NO 46
<211> LENGTH: 21
<212> TYPE: DNA
<213> ORGANISM: Artificial Sequence
<220> FEATURE:
<223> OTHER INFORMATION: synthetic

<400> SEQUENCE: 46
ccacggacga tcggtttcgt t                                        21
```

```
<210> SEQ ID NO 47
<211> LENGTH: 25
<212> TYPE: DNA
<213> ORGANISM: Artificial Sequence
<220> FEATURE:
<223> OTHER INFORMATION: synthetic

<400> SEQUENCE: 47
tgcgtaggtg atagggaggg gttac                                              25

<210> SEQ ID NO 48
<211> LENGTH: 25
<212> TYPE: DNA
<213> ORGANISM: Artificial Sequence
<220> FEATURE:
<223> OTHER INFORMATION: synthetic

<400> SEQUENCE: 48
acaaaacaca tcctattaac gcgaa                                              25

<210> SEQ ID NO 49
<211> LENGTH: 29
<212> TYPE: DNA
<213> ORGANISM: Artificial Sequence
<220> FEATURE:
<223> OTHER INFORMATION: synthetic

<400> SEQUENCE: 49
tttttatatt tcgggaattt agaaacgtc                                          29

<210> SEQ ID NO 50
<211> LENGTH: 29
<212> TYPE: DNA
<213> ORGANISM: Artificial Sequence
<220> FEATURE:
<223> OTHER INFORMATION: synthetic

<400> SEQUENCE: 50
taaaccgaaa ttaaaaaaaa aattacgcg                                          29
```

DETECTING ESOPHAGEAL DISORDERS

CROSS-REFERENCE TO RELATED APPLICATIONS

The present application is a continuation of U.S. patent application Ser. No. 16/570,782, filed Sep. 13, 2019, allowed as U.S. Pat. No. 11,104,960, which is a continuation of U.S. patent application Ser. No. 15/550,703, filed Aug. 11, 2017, allowed as U.S. Pat. No. 10,435,755, which is a 371 National Entry of International Patent Application No. PCT/US2016/023782, filed Mar. 23, 2016, which claims priority to U.S. Provisional Patent Application No. 62/139,243, filed Mar. 27, 2015, each of which is incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 10,000 Byte ASCII (Text) file named "34364-304_ST25.txt" created on Aug. 24, 2021.

FIELD OF INVENTION

Provided herein is technology for esophageal disorder screening and particularly, but not exclusively, to methods, compositions, and related uses for detecting the presence of esophageal disorders (e.g., Barrett's esophagus, Barrett's esophageal dysplasia, etc.). In addition, the technology provides methods, compositions and related uses for distinguishing between Barrett's esophagus and Barrett's esophageal dysplasia, and between Barrett's esophageal low-grade dysplasia, Barrett's esophageal high-grade dysplasia, and esophageal adenocarcinoma within samples obtained through endoscopic brushing or nonendoscopic whole esophageal brushing or swabbing using a tethered device (e.g. such as a capsule sponge, balloon, or other device).

BACKGROUND

In Barrett's esophagus, healthy esophageal epithelium is replaced with metaplastic columnar cells—the result, it is believed, of damage from prolonged exposure of the esophagus to the refluxate of gastroesophageal reflux disease (GERD). The inherent risk of progression from Barrett esophagus to adenocarcinoma of the esophagus has been established. Histologically, this progression involves clear sequential stages from metaplasia alone to low grade dysplasia, then to high grade dysplasia, and finally to adenocarcinoma.

The diagnosis of Barrett's esophagus without dysplasia does not lead to specific therapy. However, when dysplasia is present, there is sound evidence that endoscopic ablation treatment can prevent subsequent transformation to cancer. Such dysplasia is often endoscopically indistinguishable from Barrett's without dysplasia, and periodic random biopsies with histological assessment is the current approach to surveillance in patients with proven Barrett's.

Little evidence supports the assumption that antisecretory agents or antireflux surgery prevents the occurrence of adenocarcinoma or leads to regression of Barrett esophagus (see, e.g., Haag S, et al., Gastrointest Endosc. August 1999; 50(2):229-40).

In the early to mid-1980s, histamine 2 (H2)-receptor antagonists were the most commonly prescribed agents for treatment of GERD. However, a number of studies were conducted with either cimetidine or ranitidine, and none documented regression of Barrett esophagus.

In the late 1980s, proton pump inhibitors (PPIs) were introduced and proved to be much more efficacious at reducing gastric acid secretion. Even so, the supposition that better acid suppression could induce Barrett's esophagus regression was met with optimism, and studies on this to date have been inconclusive. Only 2 of 7 investigators demonstrated some regression. Most were unable to detect any regression, despite documentation of complete normalization of esophageal pH by pH testing.

Currently, the indications for medical therapy in Barrett esophagus—control of symptoms and healing of esophageal mucosa—are the same as those for GERD.

Barrett's Esophagus is a precursor lesion for most esophageal adenocarcinomas which is a malignancy with rapidly rising incidence and persistently poor outcomes. As above, early detection of esophageal adenocarcinoma has been shown to be associated with earlier stage and increased survival. And, detection of dysplasia with subsequent endoscopic ablation can prevent esophageal adenocarcinoma.

Improved methods for detecting Barrett's esophagus and related disorders (e.g., Barrett's esophageal dysplasia) are clearly needed.

SUMMARY

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression. In a biologically attractive mechanism, acquired methylation events in promoter regions of tumor suppressor genes are thought to silence expression, thus contributing to oncogenesis. DNA methylation may be a more chemically and biologically stable diagnostic tool than RNA or protein expression (Laird (2010) Nat Rev Genet 11: 191-203). Furthermore, in other cancers like sporadic colon cancer, methylation markers offer excellent specificity and are more broadly informative and sensitive than are individual DNA mutations (Zou et al (2007) Cancer Epidemiol Biomarkers Prev 16: 2686-96).

Analysis of CpG islands has yielded important findings when applied to animal models and human cell lines. For example, Zhang and colleagues found that amplicons from different parts of the same CpG island may have different levels of methylation (Zhang et al. (2009) PLoS Genet 5: e1000438). Further, methylation levels were distributed bi-modally between highly methylated and unmethylated sequences, further supporting the binary switch-like pattern of DNA methyltransferase activity (Zhang et al. (2009) PLoS Genet 5: e1000438). Analysis of murine tissues in vivo and cell lines in vitro demonstrated that only about 0.3% of high CpG density promoters (HCP, defined as having >7% CpG sequence within a 300 base pair region) were methylated, whereas areas of low CpG density (LCP, defined as having <5% CpG sequence within a 300 base pair region) tended to be frequently methylated in a dynamic tissue-specific pattern (Meissner et al. (2008) Nature 454: 766-70). HCPs include promoters for ubiquitous housekeeping genes and highly regulated developmental genes. Among the HCP sites methylated at >50% were several established markers such as Wnt 2, NDRG2, SFRP2, and BMP3 (Meissner et al. (2008) Nature 454: 766-70).

Accordingly, provided herein is technology for esophageal disorder screening (e.g., surveilling) and particularly, but not exclusively, to methods, compositions, and related uses for detecting the presence of esophageal disorders (e.g., Barrett's esophagus, Barrett's esophageal dysplasia, etc.). In addition, the technology provides methods, compositions and related uses for distinguishing between Barrett's esophagus and Barrett's esophageal dysplasia, and between Barrett's esophageal low-grade dysplasia, Barrett's esophageal high-grade dysplasia, and esophageal adenocarcinoma within samples obtained through endoscopic brushing or nonendoscopic whole esophageal brushing or swabbing using a tethered device (e.g. such as a capsule sponge, balloon, or other device).

Indeed, experiments conducted during the course of developing this technology compared the methylation state of DNA markers from esophageal tissue of subjects having Barrett's esophagus to the methylation state of the same DNA markers from control subjects (e.g., normal tissue for the respective tissue type), and to the methylation state of the same DNA markers from subjects having Barrett's esophagus dysplasia (see, Examples 1 and 5).

Markers and/or panels of markers were identified (e.g., a chromosomal region having an annotation provided in Tables 1, 7 and/or 8) capable of classifying Barrett's esophagus (BE) versus control (e.g., normal tissue for the respective tissue type) within esophageal tissue (see, Examples 1, 2 and 5).

Markers and/or panels of markers were identified (e.g., a chromosomal region having an annotation provided in Tables 2, 3, 5, and/or 6) capable of classifying BE versus Barrett's esophagus related dysplasia (BED) within esophageal tissue (see, Examples 1, 3 and 4).

Markers and/or panels of markers were identified (e.g., a chromosomal region having an annotation provided in Table 5) capable of predicting Barrett's esophagus related low-grade dysplasia (BE-LGD), Barrett's esophagus related dysplasia high-grade dysplasia (BE-HGD), and esophageal adenocarcinoma (EAC) within samples obtained through whole esophageal swabbing or brushing (see, Examples 1 and 4).

Markers and/or panels of markers were identified (e.g., a chromosomal region having an annotation provided in Table 5) capable of classifying BE versus BED within samples obtained through whole esophageal swabbing or brushing (see Examples 1 and 4).

As described herein, the technology provides a number of methylated DNA markers and subsets thereof (e.g., sets of 2, 3, 4, 5, 6, 7, 10, 15, 25, 50, 100, 150, 180, 190, 194 markers) with high discrimination for esophageal disorders (e.g., BE, BED, BE-LGD, BE-HGD, EAC). Experiments applied a selection filter to candidate markers to identify markers that provide a high signal to noise ratio and a low background level to provide high specificity, e.g., when assaying media (e.g., esophageal tissue) for purposes of screening or diagnosis (e.g., cancer screening or diagnosis).

In some embodiments, the technology is related to assessing the presence of and methylation state of one or more of the markers identified herein in a biological sample. These markers comprise one or more differentially methylated regions (DMR) as discussed herein, e.g., as provided in Tables 1, 2, 3, 5, 6, 7 and 8. Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) Mol. Cell. Biol. 14: 7421-7427) and another example involves methylation-sensitive arbitrarily primed PCR (Gonzalgo et al. (1997) Cancer Res. 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes prior to PCR amplification (Singer-Sam et al. (1990) Nucl. Acids Res. 18: 687). In addition, other techniques have been reported that utilize bisulfite treatment of DNA as a starting point for methylation analysis. These include methylation-specific PCR (MSP) (Herman et al. (1992) Proc. Natl. Acad. Sci. USA 93: 9821-9826) and restriction enzyme digestion of PCR products amplified from bisulfite-converted DNA (Sadri and Hornsby (1996) Nucl. Acids Res. 24: 5058-5059; and Xiong and Laird (1997) Nucl. Acids Res. 25: 2532-2534). PCR techniques have been developed for detection of gene mutations (Kuppuswamy et al. (1991) Proc. Natl. Acad. Sci. USA 88: 1143-1147) and quantification of allelic-specific expression (Szabo and Mann (1995) Genes Dev. 9: 3097-3108; and Singer-Sam et al. (1992) PCR Methods Appl. 1: 160-163). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. No. 8,361, 720; and U.S. Pat. Appl. Pub. Nos. 2012/0122088 and 2012/0122106).

For example, in some embodiments methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. In some embodiments, a microprocessor is part of a system for determining a methylation state (e.g., of one or more DMR, e.g., DMR 1-78 as provided in Table 1; DMR 3, 5, 30, 33, 43, 58, 77 and 79-128 as provided in Table 2; DMR 77, 27, 193, 90, 92, 101 and 129-134 as provided in Table 3; DMR 77, 90 and 135 as provided in Table 5; DMR 136-187 as provided in Table 6; DMR 21 and 188-192 as provided in Table 7; DMR 2-4, 6, 7, 14, 30, 77, 80, 82-86, 88, 90-102, 108, 122, 135, 136, 141, 142, 144, 146, 148-149, 152, 154, 156, 164, 166, 171, 173, 175, 178, 179, 181, 185, 187, and 193-229 as provided in Table 8); comparing methylation states (e.g., of one or more DMR, e.g., DMR 1-78 as provided in Table 1; DMR 3, 5, 30, 33, 43, 58, 77 and 79-128 as provided in Table 2; DMR 77, 27, 193, 90, 92, 101 and 129-134 as provided in Table 3; DMR 77, 90 and 135 as provided in Table 5; DMR 136-187 as provided in Table 6; DMR 21 and 188-192 as provided in Table 7; DMR 2-4, 6, 7, 14, 30, 77, 80, 82-86, 88, 90-102, 108, 122, 135, 136, 141, 142, 144, 146, 148-149, 152, 154, 156, 164, 166, 171, 173, 175, 178, 179, 181, 185, 187, and 193-229 as provided in Table 8); generating standard curves; determining a Ct value; calculating a fraction, frequency, or percentage of methylation (e.g., of one or more DMR, e.g., DMR 1-78 as provided in Table 1; DMR 3, 5, 30, 33, 43, 58, 77 and 79-128 as provided in Table 2; DMR 77, 27, 193, 90, 92, 101 and 129-134 as provided in Table 3; DMR 77, 90 and 135 as provided in Table 5; DMR 136-187 as provided in Table 6; DMR 21 and 188-192 as provided in Table 7; DMR 2-4, 6, 7, 14, 30, 77, 80, 82-86, 88, 90-102, 108, 122, 135, 136, 141, 142, 144, 146, 148-149, 152, 154, 156, 164, 166, 171, 173, 175, 178, 179, 181, 185, 187, and 193-229 as provided in Table 8); identifying a CpG island; determining a specificity and/or sensitivity of an assay or marker; calculating an ROC curve and an associated AUC; sequence analysis; all as described herein or is known in the art.

In some embodiments, a microprocessor or computer uses methylation state data in an algorithm to predict a site of a cancer.

In some embodiments, a software or hardware component receives the results of multiple assays and determines a single value result to report to a user that indicates a cancer risk based on the results of the multiple assays (e.g., determining the methylation state of multiple DMR, e.g., as provided in Tables 1, 2, 3, 5, 6, 7, 8). Related embodiments calculate a risk factor based on a mathematical combination (e.g., a weighted combination, a linear combination) of the results from multiple assays, e.g., determining the methylation states of multiple markers (such as multiple DMR, e.g., as provided in Tables 1, 2, 3, 5, 6, 7, 8). In some embodiments, the methylation state of a DMR defines a dimension and may have values in a multidimensional space and the coordinate defined by the methylation states of multiple DMR is a result, e.g., to report to a user, e.g., related to an esophageal disorder risk (e.g., risk of BE, BED, BE-LGD, BE-HGD, EAC).

Some embodiments comprise a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, California and Motorola Corporation of Schaumburg, Illinois Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

Accordingly, provided herein is technology related to a method of screening for BE in a sample obtained from a subject, the method comprising assaying a methylation state of a marker in a sample obtained from a subject; and identifying the subject as having BE when the methylation state of the marker is different than a methylation state of the marker assayed in a subject that does not have BE, wherein the marker comprises one or more bases in a differentially methylated region (DMR) selected from a group consisting of DMR 1-78 as provided in Table 1 and/or DMR 21 and 188-193 as provided in Table 7 and/or; DMR 2-4, 6, 7, 14, 30, 77, 80, 82-86, 88, 90-102, 108, 122, 135, 136, 141, 142, 144, 146, 148-149, 152, 154, 156, 164, 166, 171, 173, 175, 178, 179, 181, 185, 187, and 193-229 as provided in Table 8.

Provided herein is technology related to a method of distinguishing between BE and BED in a sample obtained from a subject, the method comprising assaying a methylation state of a marker in a sample obtained from a subject; and identifying the subject as having BE when the methylation state of the marker is similar to the methylation state of the marker assayed in a subject that has BE or identifying the subject as having BED when the methylation state of the marker is similar to the methylation state of the marker assayed in a subject that has BED, wherein the marker comprises one or more bases in a differentially methylated region (DMR) selected from a group consisting of DMR 3, 5, 30, 33, 43, 77 and 79-128 as provided in Table 2, DMR 77, 27, 193, 90, 92, 101, 129-134 as provided in Table 3, DMR 77, 90 and 135 as provided in Table 5, and/or DMR 136-187 as provided in Table 6.

Provided herein is technology related to a method of distinguishing between BE-LGD, BE-HGD, and BE-EAC in a sample obtained from a subject, the method comprising assaying a methylation state of a marker in a sample obtained from a subject; and identifying the subject as having BE-LGD when the methylation state of the marker is similar to the methylation state of the marker assayed in a subject that has BE-LGD, identifying the subject as having BE-HGD when the methylation state of the marker is similar to the methylation state of the marker assayed in a subject that has BE-HGD, or identifying the subject as having EAC when the methylation state of the marker is similar to the methylation state of the marker assayed in a subject that has EAC, wherein the marker comprises one or more bases in a differentially methylated region (DMR) selected from a group consisting of DMR 77, 90 and 135 as provided in Table 5.

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

Furthermore, in some embodiments the marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. In some embodiments, the sample is esophageal tissue obtained through whole esophageal swabbing or brushing (see, Example 1 and Table 5) (see, Example 5 and Table 8). In some embodiments, the sample is esophageal tissue obtained through use a sponge capsule device (see, Example 5 and Table 8). For example, in some embodiments the sample is a stool sample, a tissue sample (e.g., esophageal tissue, stomach tissue, pancreatic tissue, bile duct/liver tissue, and colorectal tissue), a blood sample (e.g., plasma, serum, whole blood), an excretion, or a urine sample.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a DMR, e.g., in some embodiments are provided a set of oligonucleotides comprising the sequences provided by SEQ ID NO: 1-50. In some embodiments are provided an oligonucleotide comprising a sequence complementary to a chromosomal region having a base in a DMR, e.g., an oligonucleotide sensitive to methylation state of a DMR.

The technology provides various panels of markers, e.g., in some embodiments the marker comprises a chromosomal region having an annotation that is provided in Tables 1, 2, 3, 5, 6, 7 and/or 8, and that comprises the marker (see, Tables 1, 2, 3, 5, 6, 7, 8). In addition, embodiments provide a method of analyzing a DMR from Tables 1, 2, 3, 5, 6, 7 and/or 8 that one or more of DMR Nos. 1-229.

Kit embodiments are provided, e.g., a kit comprising a bisulfite reagent; and a control nucleic acid comprising a sequence from a DMR selected from a group consisting of DMR 1-194 (from Tables 1, 2, 3, 5, 6, 7, and/or 8) and having a methylation state associated with a subject who does not have an esophageal disorder (e.g., a subject that does not have BE, BED, BE-LGD, BE-HGD, and EAC). In some embodiments, kits comprise a bisulfite reagent and an oligonucleotide as described herein. In some embodiments, kits comprise a bisulfite reagent; and a control nucleic acid comprising a sequence from a DMR selected from a group consisting of DMR 1-194 (from Tables 1, 2, 3, 5, 6, 7, 8) and having a methylation state associated with a subject who has an esophageal disorder (e.g., a subject who has BE) (e.g., a subject who has BED, BE-LGD, BE-HGD, EAC). Some kit embodiments comprise a sample collector for obtaining a sample from a subject (e.g., a stool sample); reagents for isolating a nucleic acid from the sample; a bisulfite reagent; and an oligonucleotide as described herein.

The technology is related to embodiments of compositions (e.g., reaction mixtures). In some embodiments are provided a composition comprising a nucleic acid comprising a DMR and a bisulfite reagent. Some embodiments provide a composition comprising a nucleic acid comprising a DMR and an oligonucleotide as described herein. Some embodiments provide a composition comprising a nucleic acid comprising a DMR and a methylation-sensitive restriction enzyme. Some embodiments provide a composition comprising a nucleic acid comprising a DMR and a polymerase.

Additional related method embodiments are provided for screening for an esophageal disorder (e.g., BE, BED, BE-LGD, BE-HGD, EAC) in a sample obtained from a subject, e.g., a method comprising determining a methylation state of a marker in the sample comprising a base in a DMR that is one or more of DMR 1-229 (from Table 1, 2, 3, 5, 6, 7, 8); comparing the methylation state of the marker from the subject sample to a methylation state of the marker from a normal control sample from a subject who does not have an esophageal disorder; and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a DMR with a bisulfite reagent to produce a bisulfite-reacted nucleic acid; sequencing the bisulfite-reacted nucleic acid to provide a nucleotide sequence of the bisulfite-reacted nucleic acid; comparing the nucleotide sequence of the bisulfite-reacted nucleic acid with a nucleotide sequence of a nucleic acid comprising the DMR from a subject who does not have a cancer to identify differences in the two sequences; and identifying the subject as having a neoplasm when a difference is present.

Systems for screening for an esophageal disorder (e.g., BE, BED, BE-LGD, BE-HGD, EAC) in a sample obtained from a subject are provided by the technology. Exemplary embodiments of systems include, e.g., a system for screening for an esophageal disorder in a sample obtained from a subject, the system comprising an analysis component configured to determine the methylation state of a sample, a software component configured to compare the methylation state of the sample with a control sample or a reference sample methylation state recorded in a database, and an alert component configured to alert a user of an esophageal disorder-associated methylation state (e.g., a methylation state for no esophageal disorder; a methylation state for BE; a methylation state for BED; a methylation state for BE-LGD; a methylation state for BE-HGD; a methylation state for EAC). An alert is determined in some embodiments by a software component that receives the results from multiple assays (e.g., determining the methylation states of multiple markers, e.g., DMR, e.g., as provided in Table 1, 2, 3, 5, 6, 7, and/or 8) and calculating a value or result to report based on the multiple results. Some embodiments provide a database of weighted parameters associated with each DMR provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of an esophageal disorder risk in a subject (e.g., risk indicative for BE; risk indicative for BED; risk indicative for BE-LGD; risk indicative for BE-HGD; risk indicative for EAC).

In some embodiments of systems, a sample comprises a nucleic acid comprising a DMR. In some embodiments the system further comprises a component for isolating a nucleic acid, a component for collecting a sample such as a component for collecting a stool sample. In some embodiments, the system comprises nucleic acid sequences comprising a DMR. In some embodiments the database comprises nucleic acid sequences from subjects who do not have an esophageal disorder. Also provided are nucleic acids, e.g., a set of nucleic acids, each nucleic acid having a sequence comprising a DMR. In some embodiments the set of nucleic acids wherein each nucleic acid has a sequence from a subject who does not have an esophageal disorder. Related system embodiments comprise a set of nucleic acids as described and a database of nucleic acid sequences associated with the set of nucleic acids. Some embodiments further comprise a bisulfite reagent. And, some embodiments further comprise a nucleic acid sequencer.

In certain embodiments, methods for detecting Barrett's esophagus in a sample obtained from a subject are provided, comprising a) obtaining a sample comprising DNA from a subject; b) treating the obtained DNA with a reagent which selectively modifies unmethylated cytosine residues in the obtained DNA to produce modified residues but which does not modify methylated cytosine residues; c) determining the methylation level of one or more DNA methylation markers in the DNA having undergone the treating of step b), wherein one or more DNA methylation markers comprises a base in a differentially methylated region (DMR) as provided by DMR Nos. 1-78, 80, 82-86, 88, 90-102, 108, 122, 135, 136, 141, 142, 144, 146, 148-149, 152, 154, 156, 164, 166, 171, 173, 175, 178, 179, 181, 185, and 187-229 d) comparing the determined methylation level of the one or more DNA methylation markers with methylation level references for the one or more DNA methylation markers for subjects: i) who do not have Barrett's esophagus to identify differences in the two sequences, and ii) who do not have Barrett's esophageal dysplasia to identify differences in the two sequences; and e) identifying the subject as having Barrett's esophagus when differences in i) and ii) are present.

In certain embodiments, methods for detecting Barrett's esophageal dysplasia in a sample obtained from a subject are provided, comprising a) obtaining a sample comprising DNA from a subject; b) treating the obtained DNA with a reagent which selectively modifies unmethylated cytosine residues in the obtained DNA to produce modified residues but which does not modify methylated cytosine residues; c) determining the methylation level of one or more DNA methylation markers in the DNA having undergone the treating of step b), wherein one or more DNA methylation markers comprises a base in a differentially methylated region (DMR) as provided by DMR Nos. 3, 5, 30, 33, 43, 58, 77, 79-187, d) comparing the determined methylation level of the one or more DNA methylation markers with methylation level references for the one or more DNA methylation markers for subjects: i) who have Barrett's esophagus to identify differences in the two sequences, and ii) who do not have Barrett's esophageal dysplasia to identify differences in the two sequences; and e) identifying the subject as having Barrett's esophageal dysplasia when differences in i) and ii) are present.

In certain embodiments, methods for detecting Barrett's esophageal low-grade dysplasia in a sample obtained from a subject are provided, comprising a) obtaining a sample comprising DNA from a subject; b) treating the obtained DNA with a reagent which selectively modifies unmethylated cytosine residues in the obtained DNA to produce modified residues but which does not modify methylated cytosine residues; c) determining the methylation level of one or more DNA methylation markers in the DNA having undergone the treating of step b), wherein one or more DNA methylation markers comprises a base in a differentially methylated region (DMR) as provided by DMR Nos. 77, 90 and 135, d) comparing the determined methylation level of the one or more DNA methylation markers with methylation level references for the one or more DNA methylation markers for subjects: i) who do not have Barrett's esophageal low-grade dysplasia to identify differences in the two sequences, ii) who do not have Barrett's esophageal dysplasia to identify differences in the two sequences, iii) who have Barrett's esophageal high-grade dysplasia to identify differences in the two sequences, and iv) who have esophageal adenocarcinoma to identify differences in the two sequences; and e) identifying the subject as having Barrett's esophageal low-grade dysplasia when differences in i), ii), iii, and iv) are present.

In certain embodiments, methods for detecting Barrett's esophageal high-grade dysplasia in a sample obtained from a subject are provided, comprising a) obtaining a sample comprising DNA from a subject; b) treating the obtained DNA with a reagent which selectively modifies unmethylated cytosine residues in the obtained DNA to produce modified residues but which does not modify methylated cytosine residues; c) determining the methylation level of one or more DNA methylation markers in the DNA having undergone the treating of step b), wherein one or more DNA methylation markers comprises a base in a differentially methylated region (DMR) as provided by DMR Nos. 77, 90 and 135, d) comparing the determined methylation level of the one or more DNA methylation markers with methylation level references for the one or more DNA methylation markers for subjects: i) who do not have Barrett's esophageal high-grade dysplasia to identify differences in the two sequences, ii) who do not have Barrett's esophageal dysplasia to identify differences in the two sequences, iii) who have Barrett's esophageal low-grade dysplasia to identify differences in the two sequences, and iv) who have esophageal adenocarcinoma to identify differences in the two sequences; and e) identifying the subject as having Barrett's esophageal high-grade dysplasia when differences in i), ii), iii, and iv) are present.

In certain embodiments, methods for detecting esophageal adenocarcinoma in a sample obtained from a subject are provided, comprising a) obtaining a sample comprising DNA from a subject; b) treating the obtained DNA with a reagent which selectively modifies unmethylated cytosine residues in the obtained DNA to produce modified residues but which does not modify methylated cytosine residues c) determining the methylation level of one or more DNA methylation markers in the DNA having undergone the treating of step b), wherein one or more DNA methylation markers comprises a base in a differentially methylated region (DMR) as provided by DMR Nos. 77, 90 and 135, d) comparing the determined methylation level of the one or more DNA methylation markers with methylation level references for the one or more DNA methylation markers for subjects: i) who do not have esophageal adenocarcinoma to identify differences in the two sequences, ii) who do not have Barrett's esophageal dysplasia to identify differences in the two sequences, iii) who have Barrett's esophageal low-grade dysplasia to identify differences in the two sequences, and iv) who have Barrett's esophageal high-grade dysplasia to identify differences in the two sequences; and e) identifying the subject as having esophageal adenocarcinoma when differences in i), ii), iii, and iv) are present.

In some embodiments, a determination of elevated methylation in one or more of the DNA methylation markers comprises a determination of altered methylation within a region selected from the group consisting of a CpG island and a CpG island shore.

In some embodiments, a determination of elevated methylation within the CpG island or CpG shore comprises elevated methylation within a coding region or a regulatory region of the DNA methylation marker.

In some embodiments, the determining the methylation level of one or more DNA methylation markers in the DNA having undergone the treating of step b) comprises determining the methylation score and/or the methylation frequency of the one or more DNA methylation markers. In some embodiments, the treating of step b) is accomplished through bisulfite modification of the obtained DNA.

In some embodiments, the determining the methylation level of one or more DNA methylation markers in the DNA having undergone the treating of step b) is achieved by a technique selected from the group consisting of methylation-specific PCR, quantitative methylation-specific PCR, methylation-sensitive DNA restriction enzyme analysis, quantitative bisulfite pyrosequencing, and bisulfite genomic sequencing PCR.

In some embodiments, the sample comprises esophageal tissue. In some embodiments, the esophageal tissue is obtained through endoscopic brushing or nonendoscopic whole esophageal brushing or swabbing using a tethered device (e.g. such as a capsule sponge, balloon, or other device).

Additional embodiments will be apparent to persons skilled in the relevant art based on the teachings contained herein.

DETAILED DESCRIPTION

Figure 1:
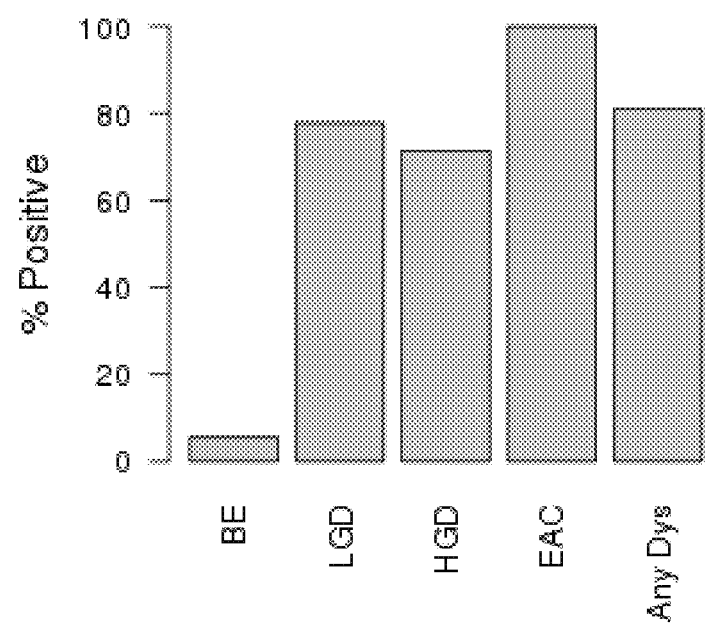
FIG. 1: Positivity rates of a 3-marker panel (DIO3, MAX20.218, NDRG4) (Table 5) in tissue DNA from BE subgroups without dysplasia and with different severities of dysplasia (Examples I, II, III and IV).

Barrett's esophagus (BE) is the strongest risk factor for and only known precursor for esophageal adenocarcinoma (EAC), a lethal malignancy with poor survival (<20% at 5 years) when detected after the onset of symptoms (see, Nelsen E M, et al., The Surgical clinics of North America 2012; 92:1135-54). The incidence of esophageal adenocarcinoma has increased by almost 600% in the last three decades in the population (see, Hur C, et al., Cancer 2013; 119:1149-58). BE progresses to EAC through a step-wise pathway from no dysplasia, to low grade dysplasia (LGD) to high grade dysplasia (HGD) to carcinoma. This metaplasia to dysplasia to carcinoma sequence has prompted several national gastroenterology societies to recommend screening for BE in high risk subjects with multiple risk factors followed by endoscopic surveillance (depending on the grade of dysplasia) to detect the development of dysplasia or carcinoma at an early stage (see, Spechler S J, et al., Gastroenterology 2011; 140:e18-52; Wang K K, et al., Am J Gastroenterol 2008; 103:788-97; Fitzgerald R C, et al., Gut 2014; 63:7-42). Endoscopic treatments of LGD, HGD and early carcinoma have been developed and shown to be effective in reducing the incidence of carcinoma and improving survival in BE subjects (see, e.g., Prasad G A, et al., Gastroenterology 2007; 132:1226-33; Prasad G A, et al., Gastroenterology 2009; Shaheen N J, et al., N Engl J Med 2009; 360:2277-88; Phoa K N, et al., JAMA 2014; 311: 1209-17).

Screening for BE is currently performed using conventional sedated endoscopy (sEGD) which reveals the replacement of the normal squamous lining of the esophagus by metaplastic columnar epithelium in subjects with BE. However sedated endoscopy is expensive with both direct and indirect costs and not suitable for widespread application. It is also associated with potential complications (see, Sami S S, et al., Clinical gastroenterology and hepatology: the official clinical practice journal of the American Gastroenterological Association 2015; 13:623-34). Other techniques such as unsedated transnasal endoscopy (uTNE) have comparable accuracy to sEGD with lower cost, but continue to be poorly regarded as a widely applicable tool by providers (see, Sami S S, et al., The American journal of gastroenterology 2015; 110:148-58; Peery A F, et al., Gastrointestinal endoscopy 2012; 75:945-953 e2; Atkinson M, et al., Gastroenterology & hepatology 2007; 4:426-7). Despite adequate access to the uTNE device the utilization of uTNE by referring physicians remains limited (see, Atkinson M, et al., The American journal of gastroenterology 2008; 103: 92-7). The absence of accurate risk stratification tools to determine BE risk and target screening efforts are additional limitations to a widely applicable BE screening (see, Sami S S, et al., Clinical gastroenterology and hepatology: the official clinical practice journal of the American Gastroenterological Association 2015; 13:623-34).

Endoscopic detection of dysplasia is currently performed using four quadrant random biopsies every 1-2 cm of the BE segment in addition to careful inspection of the BE segment with high resolution white light imaging and advanced imaging techniques. While this has been recommended by GI societies (see, e.g., Spechler S J, et al., Gastroenterology 2011; 140:e18-52; Wang K K, et al., Am J Gastroenterol 2008; 103:788-97; Fitzgerald R C, et al., Gut 2014; 63:7-42, the compliance with these recommendations amongst practicing gastroenterologists remains poor (see, Abrams J A, et al., Clin Gastroenterol Hepatol 2009). Indeed compliance decreases with increasing BE segment length leading to increasing rates of missed dysplasia. Other challenges with dysplasia detection in BE include the spotty distribution of dysplasia in BE (see, Cameron A J, et al., Am J Gastroenterol 1997; 92:586-91) which leads to sampling error, poor inter-observer agreement amongst pathologists while grading dysplasia and the relatively poor sensitivity of current surveillance strategies in detecting prevalent dysplasia or carcinoma (see, Sharma P, et al., Gastroenterology 2004; 127: 310-30). The utility of advanced imaging techniques in the community remains unclear with only a third of practicing gastroenterologists reporting use routinely in BE surveillance (see, Singh M, et al., Gastrointestinal endoscopy 2013; 78:689-95). Recently a sponge on a string device has been studied in BE screening (see, Kadri S R, et al., Bmj 2010; 341:c4372). This device consists of a polyurethane foam sponge compressed in a gelatin capsule, attached to a string. The capsule is swallowed by the patient. The gelatin shell of the capsule dissolves in the gastric fluid releasing the foam device as a sphere which is then pulled out with the attached string, providing brushing/cytology samples of the proximal stomach and esophagus. Biomarker studies can then be performed on these samples to detect BE. Two large multicenter studies have been performed in the United Kingdom with such a device using trefoil factor 3 (a protein specific to BE epithelium) detected on immunohistochemistry as a BE marker, demonstrating the feasibility, safety and accuracy of this approach (see, Kadri S R, et al., Bmj 2010; 341:c4372; Ross-Innes C S, et al., PLoS medicine 2015; 12:e1001780). The sensitivity and specificity of this marker in the detection of BE has been reported to be 73% and 94% for BE segments of >1 cm in circumferential length. Additionally this capsule sponge device has been used safely in a study conducted at Mayo Clinic Rochester in subjects with eosinophilic esophagitis (see, Katzka D A, et al., Clinical gastroenterology and hepatology: the official clinical practice journal of the American Gastroenterological Association 2015; 13:77-83 e2). Methylated DNA markers specific to BE epithelium (with and without dysplasia) have been described (see, Kaz A M, et al., Cancer letters 2014; 342: 193-9; Ahlquist D A, et al., Clinical gastroenterology and hepatology: the official clinical practice journal of the American Gastroenterological Association 2012; 10:272-7 e1).

Provided herein is technology for esophageal disorder screening and particularly, but not exclusively, to methods, compositions, and related uses for detecting the presence of esophageal disorders (e.g., Barrett's esophagus, Barrett's esophageal dysplasia, etc.). In addition, the technology provides methods, compositions and related uses for distinguishing between Barrett's esophagus and Barrett's esophageal dysplasia, and between Barrett's esophageal low-grade dysplasia, Barrett's esophageal high-grade dysplasia, and esophageal adenocarcinoma within samples obtained through whole esophageal swabbing or brushing or use of a sponge capsule device.

As the technology is described herein, the section headings used are for organizational purposes only and are not to be construed as limiting the subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, a "nucleic acid" or "nucleic acid molecule" generally refers to any ribonucleic acid or deoxyribonucleic acid, which may be unmodified or modified DNA or RNA. "Nucleic acids" include, without limitation, single- and double-stranded nucleic acids. As used herein, the term "nucleic acid" also includes DNA as described above that contains one or more modified bases. Thus, DNA with a backbone modified for stability or for other reasons is a "nucleic acid". The term "nucleic acid" as it is used herein embraces such chemically, enzymatically, or metabolically modified forms of nucleic acids, as well as the chemical forms of DNA characteristic of viruses and cells, including for example, simple and complex cells.

The terms "oligonucleotide" or "polynucleotide" or "nucleotide" or "nucleic acid" refer to a molecule having two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. Typical deoxyribonucleotides for DNA are thymine, adenine, cytosine, and guanine. Typical ribonucleotides for RNA are uracil, adenine, cytosine, and guanine.

As used herein, the terms "locus" or "region" of a nucleic acid refer to a subregion of a nucleic acid, e.g., a gene on a chromosome, a single nucleotide, a CpG island, etc.

The terms "complementary" and "complementarity" refer to nucleotides (e.g., 1 nucleotide) or polynucleotides (e.g., a sequence of nucleotides) related by the base-pairing rules. For example, the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands effects the efficiency and strength of hybridization between nucleic acid strands. This is of particular importance in amplification reactions and in detection methods that depend upon binding between nucleic acids.

The term "gene" refers to a nucleic acid (e.g., DNA or RNA) sequence that comprises coding sequences necessary for the production of an RNA, or of a polypeptide or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends, e.g., for a distance of about 1 kb on either end, such that the gene corresponds to the length of the full-length mRNA (e.g., comprising coding, regulatory, structural and other sequences). The sequences that are located 5' of the coding region and that are present on the mRNA are referred to as 5' non-translated or untranslated sequences. The sequences that are located 3' or downstream of the coding region and that are present on the mRNA are referred to as 3' non-translated or 3' untranslated sequences. The term "gene" encompasses both cDNA and genomic forms of a gene. In some organisms (e.g., eukaryotes), a genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' ends of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage, and poly adenylation.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by the hand of a person in the laboratory is naturally-occurring. A wild-type gene is often that gene or allele that is most frequently observed in a population and is thus arbitrarily designated the "normal" or "wild-type" form of the gene. In contrast, the term "modified" or "mutant" when made in reference to a gene or to a gene product refers, respectively, to a gene or to a gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

"Amplification" is a special case of nucleic acid replication involving template specificity. It is to be contrasted with non-specific template replication (e.g., replication that is template-dependent but not dependent on a specific template). Template specificity is here distinguished from fidelity of replication (e.g., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Amplification of nucleic acids generally refers to the production of multiple copies of a polynucleotide, or a portion of the polynucleotide, typically starting from a small amount of the polynucleotide (e.g., a single polynucleotide molecule, 10 to 100 copies of a polynucleotide molecule, which may or may not be exactly the same), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810) are forms of amplification. Additional types of amplification include, but are not limited to, allele-specific PCR (see, e.g., U.S. Pat. No. 5,639,611), assembly PCR (see, e.g., U.S. Pat. No. 5,965,408), helicase-dependent amplification (see, e.g., U.S. Pat. No. 7,662,594), Hot-start PCR (see, e.g., U.S. Pat. Nos. 5,773,258 and 5,338,671), intersequence-specific PCR, inverse PCR (see, e.g., Triglia, et al. (1988) Nucleic Acids Res., 16:8186), ligation-mediated PCR (see, e.g., Guilfoyle, R. et al., Nucleic Acids Research, 25:1854-1858 (1997); U.S. Pat. No. 5,508,169), methylation-specific PCR (see, e.g., Herman, et al., (1996) PNAS 93(13) 9821-9826), miniprimer PCR, multiplex ligation-dependent probe amplification (see, e.g., Schouten, et al., (2002) Nucleic Acids Research 30(12): e57), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80), nested PCR, overlap-extension PCR (see, e.g., Higuchi, et al., (1988) Nucleic Acids Research 16(15) 7351-7367), real time PCR (see, e.g., Higuchi, et al., (1992) Biotechnology 10:413-417; Higuchi, et al., (1993) Biotechnology 11:1026-1030), reverse transcription PCR (see, e.g., Bustin, S. A. (2000) J. Molecular Endocrinology 25:169-193), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons."

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-beta replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al, Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics 4:560). Finally, thermostable template-dependent DNA polymerases (e.g., Taq and Pfu DNA polymerases), by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142); enzyme mismatch cleavage methods (e.g., Variagenics, U.S. Pat. Nos. 6,110,684, 5,958,692, 5,851,770); polymerase chain reaction; branched hybridization methods (e.g., Chiron, U.S. Pat. Nos. 5,849,481, 5,710,264, 5,124,246, and 5,624,802); rolling circle replication (e.g., U.S. Pat. Nos. 6,210,884, 6,183,960 and 6,235,502); NASBA (e.g., U.S. Pat. No. 5,409,818); molecular beacon technology (e.g., U.S. Pat. No. 6,150,097); E-sensor technology (Motorola, U.S. Pat. Nos. 6,248,229, 6,221,583, 6,013,170, and 6,063,573); cycling probe technology (e.g., U.S. Pat. Nos. 5,403,711, 5,011,769, and 5,660,988); Dade Behring signal amplification methods (e.g., U.S. Pat. Nos. 6,121,001, 6,110,677, 5,914,230, 5,882,867, and 5,792,614); ligase chain reaction (e.g., Barnay Proc. Natl. Acad. Sci USA 88, 189-93 (1991)); and sandwich hybridization methods (e.g., U.S. Pat. No. 5,288,609).

The term "amplifiable nucleic acid" refers to a nucleic acid that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g, Antequera et al. (1990) Cell 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) J. Mol. Biol. 196: 261-281. For example, the observed CpG frequency over expected frequency can be calculated according to the formula R=(A×B)/(C×D), where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see, e.g., Ramsahoye (2000) Proc. Natl. Acad. Sci. USA 97: 5237-5242; Salmon and Kaye (1970) Biochim. Biophys. Acta. 204: 340-351; Grafstrom (1985) Nucleic Acids Res. 13: 2827-2842; Nyce (1986) Nucleic Acids Res. 14: 4353-4367; Woodcock (1987) Biochem. Biophys. Res. Commun. 145: 888-894).

As used herein, a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such a change in the nucleic acid molecule's nucleotide sequence can result in a nucleic acid molecule in which each methylated nucleotide is modified to a different nucleotide. Such a change in the nucleic acid nucleotide sequence can result in a nucleic acid molecule in which each unmethylated nucleotide is modified to a different nucleotide. Such a change in the nucleic acid nucleotide sequence can result in a nucleic acid molecule in which each of a selected nucleotide which is unmethylated (e.g., each unmethylated cytosine) is modified to a different nucleotide. Use of such a reagent to change the nucleic acid nucleotide sequence can result in a nucleic acid molecule in which each nucleotide that is a methylated nucleotide (e.g., each methylated cytosine) is modified to a different nucleotide. As used herein, use of a reagent that modifies a selected nucleotide refers to a reagent that modifies one nucleotide of the four typically occurring nucleotides in a nucleic acid molecule (C, G, T, and A for DNA and C, G, U, and A for RNA), such that the reagent modifies the one nucleotide without modifying the other three nucleotides. In one exemplary embodiment, such a reagent modifies an unmethylated selected nucleotide to produce a different nucleotide. In another exemplary embodiment, such a reagent can deaminate unmethylated cytosine nucleotides. An exemplary reagent is bisulfite.

As used herein, the term "bisulfite reagent" refers to a reagent comprising in some embodiments bisulfite, disulfite, hydrogen sulfite, or combinations thereof to distinguish between methylated and unmethylated cytidines, e.g., in CpG dinucleotide sequences.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) Cancer Research 57: 594-599.

The term "MethyLight™" refers to the art-recognized fluorescence-based real-time PCR technique described by Eads et al. (1999) Cancer Res. 59: 2302-2306.

The term "HeavyMethyl™" refers to an assay wherein methylation specific blocking probes (also referred to herein as blockers) covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones (1997) Nucleic Acids Res. 25: 2529-2531.

The term "MSP" (Methylation-specific PCR) refers to the art-recognized methylation assay described by Herman et al. (1996) Proc. Natl. Acad. Sci. USA 93: 9821-9826, and by U.S. Pat. No. 5,786,146.

The term "COBRA" (Combined Bisulfite Restriction Analysis) refers to the art-recognized methylation assay described by Xiong & Laird (1997) Nucleic Acids Res. 25: 2532-2534.

The term "MCA" (Methylated CpG Island Amplification) refers to the methylation assay described by Toyota et al. (1999) Cancer Res. 59: 2307-12, and in WO 00/26401A1.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

The terms "methylation-specific restriction enzyme" or "methylation-sensitive restriction enzyme" refers to an enzyme that selectively digests a nucleic acid dependent on the methylation state of its recognition site. In the case of a restriction enzyme that specifically cuts if the recognition site is not methylated or is hemimethylated, the cut will not take place or will take place with a significantly reduced efficiency if the recognition site is methylated. In the case of a restriction enzyme that specifically cuts if the recognition site is methylated, the cut will not take place or will take place with a significantly reduced efficiency if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

As used herein, a "different nucleotide" refers to a nucleotide that is chemically different from a selected nucleotide, typically such that the different nucleotide has Watson-Crick base-pairing properties that differ from the selected nucleotide, whereby the typically occurring nucleotide that is complementary to the selected nucleotide is not the same as the typically occurring nucleotide that is complementary to the different nucleotide. For example, when C is the selected nucleotide, U or T can be the different nucleotide, which is exemplified by the complementarity of C to G and the complementarity of U or T to A. As used herein, a nucleotide that is complementary to the selected nucleotide or that is complementary to the different nucleotide refers to a nucleotide that base-pairs, under high stringency conditions, with the selected nucleotide or different nucleotide with higher affinity than the complementary nucleotide's base-paring with three of the four typically occurring nucleotides. An example of complementarity is Watson-Crick base pairing in DNA (e.g., A-T and C-G) and RNA (e.g., A-U and C-G). Thus, for example, G base-pairs, under high stringency conditions, with higher affinity to C than G base-pairs to G, A, or T and, therefore, when C is the selected nucleotide, G is a nucleotide complementary to the selected nucleotide.

As used herein, the "sensitivity" of a given marker refers to the percentage of samples that report a DNA methylation value above a threshold value that distinguishes between neoplastic and non-neoplastic samples. In some embodiments, a positive is defined as a histology-confirmed neoplasia that reports a DNA methylation value above a threshold value (e.g., the range associated with disease), and a false negative is defined as a histology-confirmed neoplasia that reports a DNA methylation value below the threshold value (e.g., the range associated with no disease). The value of sensitivity, therefore, reflects the probability that a DNA methylation measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker refers to the percentage of non-neoplastic samples that report a DNA methylation value below a threshold value that distinguishes between neoplastic and non-neoplastic samples. In some embodiments, a negative is defined as a histology-confirmed non-neoplastic sample that reports a DNA methylation value below the threshold value (e.g., the range associated with no disease) and a false positive is defined as a histology-confirmed non-neoplastic sample that reports a DNA methylation value above the threshold value (e.g., the range associated with disease). The value of specificity, therefore, reflects the probability that a DNA methylation measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

The term "AUC" as used herein is an abbreviation for the "area under a curve". In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better; the optimum is 1; a random test would have a ROC curve lying on the diagonal with an area of 0.5; for reference: J. P. Egan. (1975) Signal Detection Theory and ROC Analysis, Academic Press, New York).

As used herein, the term "neoplasm" refers to "an abnormal mass of tissue, the growth of which exceeds and is uncoordinated with that of the normal tissues" See, e.g., Willis R A, "The Spread of Tumors in the Human Body", London, Butterworth & Co, 1952.

As used herein, the term "adenoma" refers to a benign tumor of glandular origin. Although these growths are benign, over time they may progress to become malignant.

The term "pre-cancerous" or "pre-neoplastic" and equivalents thereof refer to any cellular proliferative disorder that is undergoing malignant transformation.

A "site" or "region" of a neoplasm, adenoma, cancer, etc. is the tissue, organ, cell type, anatomical area, body part, etc. in a subject's body where the neoplasm, adenoma, cancer, etc. is located.

As used herein, the term "esophageal disorder" refers to types of disorder associated with the esophagus and/or esophageal tissue. Examples of esophageal disorders include, but are not limited to, Barrett's esophagus (BE), Barrett's esophageal dysplasia (BED), Barrett's esophageal low-grade dysplasia (BE-LGD), Barrett's esophageal high-grade dysplasia (BE-HGD), and esophageal adenocarcinoma (EAC).

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject contracting a neoplasm or the likelihood that such a subject will respond favorably to a compound (e.g., a pharmaceutical, e.g., a drug) or other treatment.

The term "marker", as used herein, refers to a substance (e.g., a nucleic acid or a region of a nucleic acid) that is able to diagnose a disorder (e.g., a non-cancerous disorder) (e.g., a cancerous disorder) by distinguishing disorder-associated cells (e.g., non-cancerous cells associated with the disorder) (e.g., cancerous cells associated with the disorder) from normal cells, e.g., based its methylation state.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded).

An isolated nucleic acid may, after isolation from its natural or typical environment, by be combined with other nucleic acids or molecules. For example, an isolated nucleic acid may be present in a host cell in which into which it has been placed, e.g., for heterologous expression.

The term "purified" refers to molecules, either nucleic acid or amino acid sequences that are removed from their natural environment, isolated, or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the terms "purified" or "to purify" also refer to the removal of contaminants from a sample. The removal of contaminating proteins results in an increase in the percent of polypeptide or nucleic acid of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution containing salts (e.g., NaCl), detergents (e.g., SDS), and other components (e.g., Denhardt's solution, dry milk, salmon sperm DNA, etc.).

The term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention. In some embodiments, the sample includes esophageal tissue. In some embodiments, the sample includes esophageal tissue obtained through endoscopic brushing or nonendoscopic whole esophageal brushing or swabbing using a tethered device (e.g. such as a capsule sponge, balloon, or other device).

As used herein, a "remote sample" as used in some contexts relates to a sample indirectly collected from a site that is not the cell, tissue, or organ source of the sample. For instance, when sample material originating from the pancreas is assessed in a stool sample (e.g., not from a sample taken directly from a pancreas), the sample is a remote sample.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

Embodiments of the Technology

Barrett's Esophagus is a precursor lesion for most esophageal adenocarcinomas which is a malignancy with rapidly rising incidence and persistently poor outcomes. Early detection of esophageal adenocarcinoma has been shown to be associated with earlier stage and increased survival. Early detection of Barrett's Esophagus may enable placement of patients into surveillance programs which may allow detection of neoplastic progression at an earlier stage amenable to endoscopic or surgical therapy with improved outcomes. Screening for Barrett's Esophagus and esophageal adenocarcinoma has been hampered by the lack of a widely applicable tool, as well as the lack of a biomarker which can be combined with a screening tool. Acceptability and feasibility of screening by endoscopic and novel non-endoscopic methods has been demonstrated in the population. Non-endoscopic screening methods, such as by swallowed cytology brush or stool DNA testing, offer potential cost-effective alternatives to endoscopy for identification of Barrett's Esophagus in the general population. More recently, it has also shown that several aberrantly methylated genes could serve as highly discriminant markers for Barrett's Esophagus. Indeed, a study performed on archived frozen esophageal biopsies in patients with and without Barrett's revealed that a panel of tumor-associated genes was potentially useful to discriminate between Barrett's Esophagus and squamous mucosa. (see, e.g., Yang Wu, et al, DDW Abstract 2011).

Dysplasia is known to be distributed in a patchy manner in Barrett's esophagus, leading to "sampling error" on routine endoscopic surveillance as performed by four quadrant biopsies. It is known that conventional endoscopic surveillance with biopsies samples less than 10% of the BE segment. Compliance of endoscopists with conventional surveillance is known to be poor. While newer endoscopic techniques have been shown to improve the yield of dysplasia detection in studies performed in tertiary care centers, their applicability in the community remains uncertain. Methods which sample a larger mucosal surface area, such as swabbing or brushing, are likely to increase the yield of dysplasia and neoplasia, particularly if combined with molecular markers of dysplasia/neoplasia. This may ultimately allow non-biopsy (via swabbing or brushing) or non-endoscopic surveillance of BE subjects with potential substantial cost savings.

Accordingly, provided herein is technology for esophageal disorder screening and particularly, but not exclusively, to methods, compositions, and related uses for detecting the presence of esophageal disorders (e.g., Barrett's esophagus, Barrett's esophageal dysplasia, etc.). In addition, the technology provides methods, compositions and related uses for distinguishing between Barrett's esophagus and Barrett's esophageal dysplasia, and between Barrett's esophageal low-grade dysplasia, Barrett's esophageal high-grade dysplasia, and esophageal adenocarcinoma within samples obtained through endoscopic brushing or nonendoscopic whole esophageal brushing or swabbing using a tethered device (e.g. such as a capsule sponge, balloon, or other device).

Indeed, experiments conducted during the course of developing this technology compared the methylation state of DNA markers from esophageal tissue of subjects having Barrett's esophagus to the methylation state of the same DNA markers from control subjects (e.g., normal tissue for the respective tissue type), and to the methylation state of the same DNA markers from subjects having Barrett's esophagus dysplasia (see, Examples 1-4).

Markers and/or panels of markers were identified (e.g., a chromosomal region having an annotation provided in Tables 1, 7 and/or 8) capable of classifying Barrett's esophagus (BE) versus control (e.g., normal tissue for the respective tissue type) within esophageal tissue (see, Examples 1, 2 and 5).

Markers and/or panels of markers were identified (e.g., a chromosomal region having an annotation provided in Tables 2, 3, 5, and/or 6) capable of classifying BE versus Barrett's esophagus related dysplasia (BED) within esophageal tissue (see, Examples 1, 3 and 4).

Markers and/or panels of markers were identified (e.g., a chromosomal region having an annotation provided in Table 5) capable of predicting Barrett's esophagus related low-grade dysplasia (BE-LGD), Barrett's esophagus related dysplasia high-grade dysplasia (BE-HGD), and esophageal adenocarcinoma (EAC) within samples obtained through whole esophageal swabbing or brushing (see, Example 1 and 4).

Markers and/or panels of markers were identified (e.g., a chromosomal region having an annotation provided in Table 5) capable of classifying BE versus BED within samples obtained through whole esophageal swabbing or brushing (see, Example 1 and 4).

Although the disclosure herein refers to certain illustrated embodiments, it is to be understood that these embodiments are presented by way of example and not by way of limitation.

The methods comprise determining the methylation status of at least one methylation marker in a biological sample isolated from a subject, wherein a change in the methylation state of the marker is indicative of the presence, or class of an esophageal disorder (e.g., BE, BED, BE-LGD, BE-HGD, EAC). Particular embodiments relate to markers comprising a differentially methylated region (DMR, e.g., DMR 1-229, see Tables 1, 2, 3, 5, 6, 7, 8) that are used for diagnosis (e.g., screening) of esophageal disorders (e.g., BE, BED, BE-LGD, BE-HGD, EAC), including early detection during, for example, pre-cancerous stages of disease (e.g., BE versus BED).

The markers of the present technology are particularly efficient in detecting or distinguishing between esophageal disorders (e.g., BE, BED, BE-LGD, BE-HGD, EAC), thereby providing improved means for the early detection, classification, and treatment of said disorders.

In addition to embodiments wherein the methylation analysis of at least one marker, a region of a marker, or a base of a marker comprising a DMR (e.g., DMR 1-229 from Tables 1, 2, 3, 5, 6, 7, and/or 8) provided herein and listed in Tables 1, 2, 3, 5, 6, and/or 7 is analyzed, the technology also provides panels of markers comprising at least one marker, region of a marker, or base of a marker comprising a DMR with utility for the detection of esophageal disorders (e.g., BE, BED, BE-LGD, BE-HGD, EAC), in esophageal tissue.

Some embodiments of the technology are based upon the analysis of the CpG methylation status of at least one marker, region of a marker, or base of a marker comprising a DMR.

In some embodiments, the present technology provides for the use of the bisulfite technique in combination with one or more methylation assays to determine the methylation status of CpG dinucleotide sequences within at least one marker comprising a DMR (e.g., as provided in Tables 1, 2, 3, 5, 6, 7, 8 (e.g., DMR 1-229)). Genomic CpG dinucleotides can be methylated or unmethylated (alternatively known as up- and down-methylated respectively). However the methods of the present invention are suitable for the analysis of biological samples of a heterogeneous nature, e.g., a low concentration of tumor cells, or biological materials therefrom, within a background of a remote sample (e.g., blood, organ effluent, or stool). Accordingly, when analyzing the methylation status of a CpG position within such a sample one may use a quantitative assay for determining the level (e.g., percent, fraction, ratio, proportion, or degree) of methylation at a particular CpG position.

According to the present technology, determination of the methylation status of CpG dinucleotide sequences in markers comprising a DMR has utility both in the diagnosis and characterization of esophageal disorders (e.g., BE, BED, BE-LGD, BE-HGD, EAC).

Combinations of Markers

In some embodiments, the technology relates to assessing the methylation state of combinations of markers comprising two or more DMRs from Tables 1, 2, 3, 5, 6, 7, 8 (e.g., two or more DMRs from DMR Nos. 1-194). In some embodiments, assessing the methylation state of more than one marker increases the specificity and/or sensitivity of a screen or diagnostic for identifying an esophageal disorder (e.g., BE, BED, BE-LGD, BE-HGD, EAC) in a subject.

Various cancers are predicted by various combinations of markers, e.g., as identified by statistical techniques related to specificity and sensitivity of prediction. The technology provides methods for identifying predictive combinations and validated predictive combinations for some cancers.

In some embodiments, combinations of markers (e.g., comprising a DMR) predict the site of a neoplasm.

For example, markers and/or panels of markers were identified (e.g., a chromosomal region having an annotation provided in Tables 1, 7 and/or 8) capable of classifying Barrett's esophagus (BE) versus control (e.g., normal tissue for the respective tissue type) within esophageal tissue (see, Examples 1, 2 and 5).

Markers and/or panels of markers were identified (e.g., a chromosomal region having an annotation provided in Tables 2, 3, 5, and/or 6) capable of classifying BE versus Barrett's esophagus related dysplasia (BED) within esophageal tissue (see, Examples 1, 3 and 4).

Markers and/or panels of markers were identified (e.g., a chromosomal region having an annotation provided in Table 5) capable of predicting Barrett's esophagus related low-grade dysplasia (BE-LGD), Barrett's esophagus related dysplasia high-grade dysplasia (BE-HGD), and esophageal adenocarcinoma (EAC) within samples obtained through whole esophageal swabbing or brushing (see, Examples 1 and 4).

Markers and/or panels of markers were identified (e.g., a chromosomal region having an annotation provided in Table 5) capable of classifying BE versus BED within samples obtained through whole esophageal swabbing or brushing (see, Examples 1 and 4).

Methods for Assaying Methylation State

The most frequently used method for analyzing a nucleic acid for the presence of 5-methylcytosine is based upon the bisulfite method described by Frommer, et al. for the detection of 5-methylcytosines in DNA (Frommer et al. (1992) Proc. Natl. Acad. Sci. USA 89: 1827-31) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uricil is desulfonated under alkaline conditions to form uracil. Detection is possible because uracil forms base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98) or methylation-specific PCR (MSP) as is disclosed, e.g., in U.S. Pat. No. 5,786,146.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" Nucleic Acids Res. 24: 5064-6). It is thus possible to analyze individual cells for methylation status, illustrating the utility and sensitivity of the method. An overview of conventional methods for detecting 5-methylcytosine is provided by Rein, T., et al. (1998) Nucleic Acids Res. 26: 2255.

The bisulfite technique typically involves amplifying short, specific fragments of a known nucleic acid subsequent to a bisulfite treatment, then either assaying the product by sequencing (Olek & Walter (1997) Nat. Genet. 17: 275-6) or a primer extension reaction (Gonzalgo & Jones (1997) Nucleic Acids Res. 25: 2529-31; WO 95/00669; U.S. Pat. No. 6,251,594) to analyze individual cytosine positions. Some methods use enzymatic digestion (Xiong & Laird (1997) Nucleic Acids Res. 25: 2532-4). Detection by hybridization has also been described in the art (Olek et al., WO 99/28498). Additionally, use of the bisulfite technique for methylation detection with respect to individual genes has been described (Grigg & Clark (1994) Bioessays 16: 431-6; Zeschnigk et al. (1997) Hum Mol Genet. 6: 387-95; Feil et al. (1994) Nucleic Acids Res. 22: 695; Martin et al. (1995) Gene 157: 261-4; WO 9746705; WO 9515373).

Various methylation assay procedures are known in the art and can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

For example, genomic sequencing has been simplified for analysis of methylation patterns and 5-methylcytosine distributions by using bisulfite treatment (Frommer et al. (1992) Proc. Natl. Acad. Sci. USA 89: 1827-1831). Additionally, restriction enzyme digestion of PCR products amplified from bisulfite-converted DNA finds use in assessing methylation state, e.g., as described by Sadri & Hornsby (1997) Nucl. Acids Res. 24: 5058-5059 or as embodied in the method known as COBRA (Combined Bisulfite Restriction Analysis) (Xiong & Laird (1997) Nucleic Acids Res. 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, DMR, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Preferably, assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, DMR, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, DMR, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HeavyMethyl™ and MSP techniques) or with oligonucleotides covering potential methylation sites.

The QM™ process can be used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, DMR, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clinical samples at single-nucleotide resolution" Nat Methods 7: 133-6; Meissner et al. (2005) "Reduced representation bisulfite sequencing for comparative high-resolution DNA methylation analysis" Nucleic Acids Res. 33: 5868-77.

In some embodiments, a quantitative allele-specific real-time target and signal amplification (QuARTS) assay is used to evaluate methylation state. Three reactions sequentially occur in each QuARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes cleavase to release the flap sequence by cutting between the detection probe and the flap sequence. The flap sequence is complementary to a nonhairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" Clin Chem 56: A199; U.S. patent application Ser. Nos. 12/946,737, 12/946,745, 12/946,752, and 61/548,639.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715). It is preferred that the bisulfite treatment is conducted in the presence of denaturing solvents such as but not limited to n-alkylenglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715). The bisulfite conversion is preferably carried out at a reaction temperature between 30° C. and 70° C., whereby the temperature is increased to over 85° C. for short times during the reaction (see: PCT/EP2004/011715). The bisulfite treated DNA is preferably purified prior to the quantification. This may be conducted by any means known in the art, such as but not limited to ultrafiltration, e.g., by means of Microcon™ columns (manufactured by Millipore™). The purification is carried out according to a modified manufacturer's protocol (see, e.g., PCT/EP2004/011715).

In some embodiments, fragments of the treated DNA are amplified using sets of primer oligonucleotides according to the present invention (e.g., see Tables 4 and 9) and an amplification enzyme. The amplification of several DNA segments can be carried out simultaneously in one and the same reaction vessel. Typically, the amplification is carried out using a polymerase chain reaction (PCR). Amplicons are typically 100 to 2000 base pairs in length.

In another embodiment of the method, the methylation status of CpG positions within or near a marker comprising a DMR (e.g., DMR 1-229 as provided in Tables 1, 2, 3, 5, 6, 7, 8) may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG.

The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Methods for isolating DNA suitable for these assay technologies are known in the art. In particular, some embodiments comprise isolation of nucleic acids as described in U.S. patent application Ser. No. 13/470,251 ("Isolation of Nucleic Acids").

Methods

In some embodiments the technology, methods are provided that comprise the following steps:
1) contacting a nucleic acid (e.g., genomic DNA, e.g., isolated from a body fluids such as a stool sample, a blood sample, or a tissue sample (e.g., esophageal tissue)) obtained from a subject with at least one reagent or series of reagents that distinguishes between methylated and non-methylated CpG dinucleotides within at least one marker comprising a DMR (e.g., DMR 1-78 as provided in Table 1, DMR 21, 188-193 as provided in Table 7, DMR 2-4, 6, 7, 14, 30, 77, 80, 82-86, 88, 90-102, 108, 122, 135, 136, 141, 142, 144, 146, 148-149, 152, 154, 156, 164, 166, 171, 173, 175, 178, 179, 181, 185, 187, 193-229 as provided in Table 8) and
2) detecting a lack of Barrett's esophagus (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a body fluids such as a stool sample, a blood sample, or a tissue sample (e.g., esophageal tissue)) obtained from a subject with at least one reagent or series of reagents that distinguishes between methylated and non-methylated CpG dinucleotides within at least one marker comprising a DMR (e.g., DMR 1-78 as provided in Table 1, DMR 21, 188-193 as provided in Table 7, DMR 2-4, 6, 7, 14, 30, 77, 80, 82-86, 88, 90-102, 108, 122, 135, 136, 141, 142, 144, 146, 148-149, 152, 154, 156, 164, 166, 171, 173, 175, 178, 179, 181, 185, 187, 193-229 as provided in Table 8) and
2) detecting a presence of Barrett's esophagus (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a body fluids such as a stool sample, a blood sample, or a tissue sample (e.g., esophageal tissue)) obtained from a subject with at least one reagent or series of reagents that distinguishes between methylated and non-methylated CpG dinucleotides within at least one marker comprising a DMR (e.g., DMR No. 3, 5, 30, 33, 43, 58, 77 and 79-128 as provided in Table 2, DMR No. 77, 27, 193, 90, 92, 101 and 129-134 as provided in Table 3, DMR No. 77, 90 and 135 as provided in Table 5, DMR No. 136-187 as provided in Table 6) and
2) classifying Barrett's esophagus or Barrett's esophageal dysplasia (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from esophageal tissue (e.g., esophageal tissue obtained through whole esophageal swabbing or brushing)) obtained from a subject with at least one reagent or series of reagents that distinguishes between methylated and non-methylated CpG dinucleotides within at least one marker comprising a DMR (e.g., DMR No. 77, 90 and 135 as provided in Table 5) and
2) classifying Barrett's esophagus or Barrett's esophageal dysplasia (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from esophageal tissue (e.g., esophageal tissue obtained through whole esophageal swabbing or brushing)) obtained from a subject with at least one reagent or series of reagents that distinguishes between methylated and non-methylated CpG dinucleotides within at least one marker comprising a DMR (e.g., DMR No. 77, 90 and 135 as provided in Table 5) and
2) classifying Barrett's esophageal low-grade dysplasia, Barrett's esophageal high-grade dysplasia, or esophageal adenocarcinoma (e.g., afforded with a sensitivity of greater than or equal to 80% and a specificity of greater than or equal to 80%).

Preferably, the sensitivity is from about 70% to about 100%, or from about 80% to about 90%, or from about 80% to about 85%. Preferably, the specificity is from about 70% to about 100%, or from about 80% to about 90%, or from about 80% to about 85%.

Genomic DNA may be isolated by any means, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All clinical sample types comprising neoplastic matter or preneoplastic matter are suitable for use in the present method, e.g., cell lines, histological slides, biopsies, paraffin-embedded tissue, body fluids, stool, colonic effluent, urine, blood plasma, blood serum, whole blood, isolated blood cells, cells isolated from the blood, and combinations thereof.

In some embodiments wherein the sample includes esophageal tissue, the sample is obtained through endoscopic techniques.

In some embodiments wherein the sample includes esophageal tissue, the sample is obtained through endoscopic brushing or nonendoscopic whole esophageal brushing or swabbing using a tethered device (e.g. such as a capsule sponge, balloon, or other device).

The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Appl. Ser. No. 61/485,386 or by a related method.

The genomic DNA sample is then treated with at least one reagent, or series of reagents, that distinguishes between methylated and non-methylated CpG dinucleotides within at least one marker comprising a DMR (e.g., DMR 1-229, e.g., as provided by Tables 1, 2, 3, 5, 6, 7, 8).

In some embodiments, the reagent converts cytosine bases which are unmethylated at the 5'-position to uracil, thymine, or another base which is dissimilar to cytosine in terms of hybridization behavior. However in some embodiments, the reagent may be a methylation sensitive restriction enzyme.

In some embodiments, the genomic DNA sample is treated in such a manner that cytosine bases that are unmethylated at the 5' position are converted to uracil, thymine, or another base that is dissimilar to cytosine in terms of hybridization behavior. In some embodiments, this treatment is carried out with bisulfate (hydrogen sulfite, disulfite) followed by alkaline hydrolysis.

The treated nucleic acid is then analyzed to determine the methylation state of the target gene sequences (at least one gene, genomic sequence, or nucleotide from a marker comprising a DMR, e.g., at least one DMR chosen from DMR 1-229, e.g., as provided in Tables 1, 2, 3, 5, 6, 7, 8). The method of analysis may be selected from those known in the art, including those listed herein, e.g., QuARTS and MSP as described herein.

The technology relates to the analysis of any sample associated with an esophageal disorder (e.g., BE, BED, BE-LGD, BE-HGD, EAC). For example, in some embodiments the sample comprises a tissue and/or biological fluid obtained from a patient. In some embodiments, the sample comprises esophageal tissue. In some embodiments, the sample comprises esophageal tissue obtained through whole esophageal swabbing or brushing. In some embodiments, the sample comprises a secretion. In some embodiments, the sample comprises blood, serum, plasma, gastric secretions, pancreatic juice, a gastrointestinal biopsy sample, microdissected cells from an esophageal biopsy, esophageal cells sloughed into the gastrointestinal lumen, and/or esophageal cells recovered from stool. In some embodiments, the subject is human. These samples may originate from the upper gastrointestinal tract, the lower gastrointestinal tract, or comprise cells, tissues, and/or secretions from both the upper gastrointestinal tract and the lower gastrointestinal tract. The sample may include cells, secretions, or tissues from the liver, bile ducts, pancreas, stomach, colon, rectum, esophagus, small intestine, appendix, duodenum, polyps, gall bladder, anus, and/or peritoneum. In some embodiments, the sample comprises cellular fluid, ascites, urine, feces, pancreatic fluid, fluid obtained during endoscopy, blood, mucus, or saliva. In some embodiments, the sample is a stool sample.

Such samples can be obtained by any number of means known in the art, such as will be apparent to the skilled person. For instance, urine and fecal samples are easily attainable, while blood, ascites, serum, or pancreatic fluid samples can be obtained parenterally by using a needle and syringe, for instance. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens. In some embodiments, the sample is obtained through esophageal swabbing or brushing or use of a sponge capsule device.

In some embodiments, the technology relates to a method for treating a patient (e.g., a patient with BE, BED, BE-LGD, BE-HGD, and/or EAC), the method comprising determining the methylation state of one or more DMR as provided herein and administering a treatment to the patient based on the results of determining the methylation state. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments of the technology, a method for diagnosing an esophageal disorder (e.g., BE, BED, BE-LGD, BE-HGD, EAC) in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker (e.g., a DMR as disclosed herein), the methylation state of which is indicative of the presence, severity, or absence of the condition.

Along with diagnosis, clinical cancer prognosis (e.g., for BED, BE-LGD, BE-HGD, EAC) relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of making determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers (e.g., DMR) disclosed herein. Further, in some embodiments of the presently disclosed subject matter, multiple determinations of the biomarkers over time can be made to facilitate diagnosis and/or prognosis. A temporal change in the biomarker can be used to predict a clinical outcome, monitor the progression of esophageal disorder, and/or monitor the efficacy of appropriate therapies directed against the cancer. In such an embodiment for example, one might expect to see a change in the methylation state of one or more biomarkers (e.g., DMR) disclosed herein (and potentially one or more additional biomarker(s), if monitored) in a biological sample over time during the course of an effective therapy.

The presently disclosed subject matter further provides in some embodiments a method for determining whether to initiate or continue prophylaxis or treatment of an esophageal disorder (e.g., BE, BED, BE-LGD, BE-HGD, EAC) in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing the esophageal disorder, predict clinical outcome, determine whether to initiate or continue the prophylaxis or therapy of the cancer, and whether a current therapy is effectively treating the esophageal disorder. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with esophageal disorder risk, prognosis, determining treatment efficacy, and/or progression of the esophageal disorder in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of the esophageal disorder, or a given prognosis. Likewise, a decrease in the marker from the initial time to the second time can be indicative of a particular type or severity of an esophageal disorder, or a given prognosis. Furthermore, the degree of change of one or more markers can be related to the severity of the esophageal disorder and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker (e.g., a DMR). Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., having a normal methylation state of one or more DMR), the chance of a given outcome (e.g., suffering from an esophageal disorder) may be very low.

In some embodiments, a statistical analysis associates a prognostic indicator with a predisposition to an adverse outcome. For example, in some embodiments, a methylation state different from that in a normal control sample obtained from a patient who does not have an esophageal disorder can signal that a subject is more likely to suffer from an esophageal disorder than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value (see, e.g., Dowdy and Wearden, Statistics for Research, John Wiley & Sons, New York, 1983). Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein (e.g., a DMR) can be established, and the degree of change in the methylation state of the biomarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with metaplasia or from donors with an esophageal disorder (e.g., BE, BED, BE-LGD, BE-HGD, EAC). In certain embodiments of the method, a subject is identified as having an esophageal disorder upon identifying an aberrant methylation state of one or more DMR provided herein in a biological sample obtained from the subject. In other embodiments of the method, the detection of an aberrant methylation state of one or more of such biomarkers in a biological sample obtained from the subject results in the subject being identified as having an esophageal disorder (e.g., BE, BED, BE-LGD, BE-HGD, EAC).

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having an esophageal disorder (e.g., BE, BED, BE-LGD, BE-HGD, EAC) if, when compared to a control methylation state, there is a measurable difference in the methylation state of at least one biomarker in the sample. Conversely, when no change in methylation state is identified in the biological sample, the subject can be identified as not having an esophageal disorder, not being at risk for the esophageal disorder, or as having a low risk of the esophageal disorder. In this regard, subjects having the esophageal disorder or risk thereof can be differentiated from subjects having low to substantially no esophageal disorder or risk thereof. Those subjects having a risk of developing an esophageal disorder can be placed on a more intensive and/or regular screening schedule, including endoscopic surveillance. On the other hand, those subjects having low to substantially no risk may avoid being subjected to an endoscopy or esophageal brushing, until such time as a future screening, for example, a screening conducted in accordance with the present technology, indicates that a risk of esophageal disorder has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, an esophageal disorder indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the diagnosis and treatment of livestock, including, but not limited to, domesticated swine, ruminants, ungulates, horses (including race horses), and the like. The presently-disclosed subject matter further includes a system for diagnosing an esophageal disorder (e.g., BE, BED, BE-LGD, BE-HGD, EAC) in a subject. The system can be provided, for example, as a commercial kit that can be used to screen for a risk of esophageal disorder or diagnose an esophageal disorder in a subject from whom a biological sample has been collected. An exemplary system provided in accordance with the present technology includes assessing the methylation state of a DMR as provided in Tables 1, 2, 3, 5, 6, 7 and/or 8.

EXAMPLES

Example I

Molecular markers may aid in detection of Barrett's esophagus (BE) and surveillance of BE-related dysplasia (BED) by either endoscopic or non-endoscopic methods. Experiments were conducted to (1) identify and validate novel methylated DNA markers for BE dysplasia, (2) test the feasibility of candidate markers for detection of BE dysplasia from whole-esophageal brushings.

Using whole methylome bisulfite sequencing on DNA from BE tissues with no dysplasia, low grade dysplasia (BE-LGD), high grade dysplasia (BE-HGD) or adenocarcinoma (EAC) (18 specimens per group), candidate markers were identified to separate BE from normal tissue, and to separate BED from BE without dysplasia.

Tables 1 and 7 provide DMR information including chromosome number, gene annotation, and DMR start/stop position for such markers identified to separate BE from normal tissue (see, Example II for materials/methods utilized in generating Tables 1 and 7).

Tables 2 and 6 provide DMR information including chromosome number, gene annotation, and DMR start/stop position for such markers identified to separate BED from BE without dysplasia (see, Example III for materials/methods utilized in generating Tables 2 and 6). Top candidate markers were validated by methylation-specific PCR assay in independent tissues including BE without dysplasia, BE-LGD, and BE-HGD (30-36 specimens per group).

Consenting BE subjects scheduled for endoscopic BE surveillance or endoscopic assessment of BE related cancers underwent whole esophageal brushings using a high capacity cytology brush (Hobbs Medical, Stafford Springs, CT) with circumferential sampling from the cardia through the full esophageal length (BE+squamous mucosa) to simulate a swallowed sponge-on-string device. Following DNA extraction and bisulfite treatment, methylation on target genes was assayed by methylation-specific PCR or quantitative allele-specific real-time target and signal amplification. Marker levels were normalized to β-actin (marker for total human DNA). 12 aberrantly methylated genes were identified that best discriminated BED with from BE without dysplasia (e.g. areas under ROC curve 0.86-0.97) (see, Table 3). These 12 markers were DIO3, MAX20.218, CD1D, T-SPYL5, ZNF568, ST8SIA1, ELMO1, ELOVL2, BMP3, NDRG4, HUNK, and CDKN2A. Table 3 DMR provides information including chromosome number, gene annotation, and DMR start/stop position for such markers identified to separate BED from BE without dysplasia within esophageal samples obtained through whole esophageal brushings. Table 4 provides forward primer and reverse primer information for the DMRs provided in Table 3. 39 subjects were studied with a median age of 69 (28-94) years, 74% were males, and median BE length was 4 (1-14) cm; 18 had no dysplasia and 21 had dysplasia (9 LGD, 7 HGD, and 5 EAC (4 asymptomatic early stage). A 3 marker set (DIO3, MAX20.218, NDRG4) (see, Table 5) at 95% specificity detected 78% of LGD, 71% of HGD, 100% of EAC and 81% of all dysplasia (see, FIG. 1). Table 5 provides DMR information including chromosome number, gene annotation, and DMR start/stop position for such markers identified to distinguish between LGD, HGD and EAC.

TABLE 1

Information for DMRs distinguishing BE and normal tissue

| DMR No. | Chromosome No. | Gene Annotation | Transcript | DMR Start Position | DMR End Position |
|---|---|---|---|---|---|
| 1 | chr19 | ZN F256 | NM_005773 | 58459137 | 58459219 |
| 2 | chr19 | ZN F568 | NM_198539 | 37407197 | 37407284 |
| 3 | chr5 | IRX4 | NM_016358 | 1883238 | 1883312 |
| 4 | chr6 | RGS17 | NM_012419 | 153451813 | 153451881 |
| 5 | chr7 | GLI3 | NM_000168 | 42276862 | 42277220 |
| 6 | chr4 | EP HA5 | NM_182472; NM_004439 | 66536122 | 66536220 |
| 7 | chr10 | SFMBT2 | NM_001029880; NM_00101039 | 7451771 | 7451869 |
| 8 | chr3 | WNT5A | NM_003392 | 55522021 | 55522106 |
| 9 | chr4 | VEGFC | NM_005429 | 177713309 | 177713364 |
| 10 | chr5 | ZNF354C | NM_014594 | 178487249 | 178487299 |
| 11 | chr19 | ZNF85 | NM_003429; NR_034060 | 21106043 | 21106185 |
| 12 | chr8 | FAM150A | NM_207413 | 53477546 | 53477636 |
| 13 | chr1 | NTNG1 | NM_014917; NM_00111322; NM_00111228 | 107684356 | 107684482 |
| 14 | chr19 | A1BG | NM_130786 | 58859193 | 58859258 |
| 15 | chr13 | SPG20 | NM_001142294; NM_015087; NM_00114229; NM_001142295 | 36920933 | 36921108 |
| 16 | chr3 | EPHA6 | NM_001080448 | 96533015 | 96533096 |
| 17 | chr16 | FOXF1 | NM_001451 | 86542355 | 86542441 |
| 18 | chr2 | MYT1L | NM_015025 | 1821558 | 1821642 |
| 19 | chr9 | — | — | 99449250 | 99449346 |
| 20 | chr7 | — | — | 84815089 | 84815157 |
| 21 | chr19 | ZNF682 | NM_001077349; NM_033196 | 20149796 | 20149923 |
| 22 | chr8 | PREX2 | NM_025170; NM_024870 | 68864872 | 68864921 |
| 23 | chr1 | WNT3A | NM_033131 | 228195339 | 228195413 |
| 24 | chr7 | TFPI2 | NM_006528 | 93520157 | 93520217 |
| 25 | chr1 | EDARADD | NM_145861; NM_080738 | 236559238 | 236559336 |
| 26 | chr1 | WNT3A | NM_033131 | 228195101 | 228195175 |
| 27 | chr16 | NDRG4 | NM_020465; NM_001130487; NM_022910 | 58497251 | 58497332 |
| 28 | chr19 | — | — | 15090770 | 15090853 |
| 29 | chr8 | — | — | 49782979 | 49783039 |
| 30 | chr12 | DPY19L2 | NM_173812 | 64061896 | 64062007 |
| 31 | chr14 | — | — | 97685552 | 97685636 |
| 32 | chr2 | EFEMP1 | NM_004105; NM_00103934; NM_00103349 | 56150932 | 56150987 |
| 33 | chr17 | NGFR | NM_002507 | 47574211 | 47574294 |
| 34 | chr8 | PREX2 | NM_025170; NM_024870 | 68864927 | 68865051 |
| 35 | chr2 | PXDN | NM_012293 | 1748578 | 1748660 |
| 36 | chr8 | C8orf42 | NM_175075 | 494156 | 494193 |
| 37 | chr16 | DKFZP434H168 | NR_026889 | 56228448 | 56228463 |
| 38 | chr14 | FLRT2 | NM_013231 | 85998492 | 85998535 |
| 39 | chr20 | SOX18 | NM_018419 | 62680089 | 62680150 |
| 40 | chr1 | PIK3CD | NM_005026 | 9711854 | 9711974 |
| 41 | chr13 | NALCN | NM_052867 | 102069229 | 102069258 |
| 42 | chr15 | ATP10A | NM_024490 | 26108587 | 26108685 |
| 43 | chr10 | GRID1 | NM_017551 | 88125585 | 88125655 |
| 44 | chr18 | NOL4 | NM_003787; NM_001198548; NM_001198546; NM_00118547; NR_036752 | 31802599 | 31802655 |

TABLE 1-continued

Information for DMRs distinguishing BE and normal tissue

| DMR No. | Chromosome No. | Gene Annotation | Transcript | DMR Start Position | DMR End Position |
|---|---|---|---|---|---|
| 45 | chr5 | FSTL4 | NM_015082 | 132946635 | 132946746 |
| 46 | chr16 | DKFZP434H168 | NR_026889 | 56228468 | 56228505 |
| 47 | chr12 | TBC1D30 | NM_015279 | 65218475 | 65218525 |
| 48 | chr2 | GAL3ST2 | NM_022134 | 242742873 | 242743049 |
| 49 | chr12 | — | — | 47225496 | 47225592 |
| 50 | chr11 | FOLH1 | NM_001193472; NM_001193473; NM_004476; NM_001193471; NM_001014986 | 49229987 | 49230073 |
| 51 | chr14 | FLJ43390 | NR_015358 | 62584108 | 62584204 |
| 52 | chr21 | TIAM1 | NM_003253 | 32932297 | 32932372 |
| 53 | chr4 | SLIT2 | NM_004787 | 20254997 | 20255028 |
| 54 | chr6 | — | — | 28979210 | 28979409 |
| 55 | chr2 | — | — | 1554621 | 1554768 |
| 56 | chr12 | PTPRO | NM_002848; NM_030667 | 15475654 | 15475697 |
| 57 | chr4 | HAND2 | NM_021973 | 174451394 | 174451439 |
| 58 | chr4 | — | — | 180980619 | 180980711 |
| 59 | chr10 | PPAPDC1A | NM_001030059 | 122216135 | 122216312 |
| 60 | chr17 | FMNL1 | NM_005892 | 43298763 | 43298872 |
| 61 | chr4 | FAT4 | NM_024582 | 126237876 | 126237908 |
| 62 | chr1 | PRRX1 | NM_006902; NM_022716 | 170633637 | 170633683 |
| 63 | chr5 | SLC27A6 | NM_014031; NM_001017372 | 128301108 | 128301233 |
| 64 | chr18 | TCF4 | NM_001083962; NM_003199 | 53257019 | 53257106 |
| 65 | chr14 | FLRT2 | NM_013231 | 85997993 | 85998139 |
| 66 | chr20 | SLC32A1 | NM_080552 | 37353717 | 37353740 |
| 67 | chr8 | KCNB2 | NM_004770 | 73450042 | 73450129 |
| 68 | chr7 | DPY19L2P4 | NR_003551 | 89747980 | 89748001 |
| 69 | chr17 | — | — | 19483467 | 19483522 |
| 70 | chr10 | GRID1 | NM_017551 | 88125122 | 88125227 |
| 71 | chr6 | B3GAT2 | NM_080742 | 71666972 | 71667038 |
| 72 | chr7 | — | — | 42533077 | 42533175 |
| 73 | chr19 | ANKRD27 | NM_032139 | 33167174 | 33167250 |
| 74 | chr4 | GABRA2 | NM_001114175; NM_000807 | 46392399 | 46392486 |
| 75 | chr1 | — | — | 39044435 | 39044453 |
| 76 | chr3 | CHL1 | NM_006614 | 238318 | 238401 |
| 77 | chr14 | DIO3 | NM_001362 | 102026104 | 102026145 |
| 78 | chr9 | IGFBPL1 | NM_001007563 | 38424583 | 38424652 |

TABLE 2

Information for DMRs Distinguishing BE from BED

| DMR No. | Chromosome No. | Gene Annotation | Transcript | DMR Start Position | DMR Stop Position |
|---|---|---|---|---|---|
| 79 | chr10 | — | — | 71267810 | 71267844 |
| 80 | chr7 | WNT2 | NM_003391; NR_024047 | 116964596 | 116964659 |
| 81 | chr7 | ARPC1B | NM_005720 | 98990762 | 98990837 |
| 82 | chr19 | RGL3 | NM_001035223; NM_001161616 | 11529371 | 11529430 |
| 83 | chr15 | FEM1B | NM_015322 | 68569729 | 68569799 |
| 84 | chr15 | ARNT2 | NM_014862 | 80696170 | 80696177 |
| 85 | chr15 | LARP6 | NM_197958; NM_018357 | 71146759 | 71146820 |
| 86 | chr7 | ZC3HAV1L | NM_080660 | 138720915 | 138720957 |
| 87 | chr2 | CYBRD1 | NM_024843; NM_001127383 | 172379904 | 172379997 |
| 88 | chr15 | Max.chr15.41877531.41877548 | — | 41877531 | 41877548 |
| 89 | chr7 | GTF2IRD1 | NM_005685; NM_001199207; NM_0163278 | 73894929 | 73895008 |
| 90 | chr20 | Max.chr20.2188420.2188480 | — | 2188420 | 2188480 |
| 91 | chr18 | KLHL14 | NM_020805 | 30351268 | 30351486 |
| 92 | chr21 | HUNK | NM_014586 | 33246580 | 33246650 |
| 93 | chr19 | LOC100131691 | NR_027334 | 59073783 | 59073952 |

TABLE 2-continued

Information for DMRs Distinguishing BE from BED

| DMR No. | Chromosome No. | Gene Annotation | Transcript | DMR Start Position | DMR Stop Position |
|---|---|---|---|---|---|
| 94 | chr13 | Max.chr13.95620964.95621061 | — | 95620964 | 95621061 |
| 95 | chr5 | Max.chr5.926920.927009 | — | 926920 | 927009 |
| 96 | chr6 | C6orf114 | NM_033069 | 13488436 | 13488530 |
| 97 | chr8 | ARHGEF10 | NM_014629 | 1771362 | 1771477 |
| 98 | chr20 | VSTM2L | NM_080607 | 36531194 | 36531312 |
| 99 | chr3 | ACAD11 | NM_032169 | 132378234 | 132378296 |
| 100 | chr12 | WSB2 | NM_018639 | 118500206 | 118500305 |
| 101 | chr9 | CDKN2A | NM_000077; NM_001195132; NM_0581975; NM_058197 | 21974710 | 21974763 |
| 102 | chr6 | Max.chr6.27064706.27064783 | — | 27064706 | 27064783 |
| 103 | chr6 | SGK1 | NM_001143676 | 134638972 | 134639020 |
| 104 | chr6 | SLC35B3 | NM_015948; NM_001142540; NM_00114541 | 8436074 | 8436140 |
| 105 | chr1 | PDE4DIP | NM_022359; NM_001198832 | 145039649 | 145039883 |
| 106 | chr3 | SOX2OT | NR_004053 | 181413970 | 181414052 |
| 107 | chr2 | KLH L29 | NM_052920 | 23609989 | 23610069 |
| 108 | chr12 | WIF1 | NM_007191 | 65514995 | 65515089 |
| 109 | chr5 | EBF1 | NM_024007 | 158526068 | 158526167 |
| 110 | chr11 | RDX | NM_002906 | 110167594 | 110167690 |
| 111 | chr6 | LOC100526820 | NR_037593 | 163837485 | 163837640 |
| 5 | chr7 | GLI3 | NM_000168 | 42276862 | 42277220 |
| 112 | chr7 | EN2 | NM_001427 | 155249880 | 155249949 |
| 113 | chr10 | ZNF365 | NM_199450; NM_199451; NM_014951 | 64133794 | 64133834 |
| 114 | chr12 | — | — | 59990783 | 59990950 |
| 115 | chr2 | — | — | 238480870 | 238480950 |
| 116 | chr19 | RYR1 | NM_001042723; NM_000540 | 39055744 | 39055882 |
| 117 | chr3 | PTPRG | NM_002841 | 61549380 | 61549403 |
| 118 | chr20 | CYP24A1 | NM_001128915; NM_000782 | 52790139 | 52790206 |
| 119 | chr19 | GDF15 | NM_004864 | 18499563 | 18499621 |
| 120 | chr17 | ULK2 | NM_001142610; NM_014683 | 19771310 | 19771382 |
| 121 | chr18 | SETBP1 | NM_015559; NM_001130110 | 42261225 | 42261288 |
| 122 | chr7 | DLX5 | NM_005221 | 96653893 | 96653955 |
| 123 | chr12 | TRPV4 | NM_021625 | 110271304 | 110271388 |
| 77 | chr14 | 0103 | NM_001362 | 102026104 | 102026145 |
| 43 | chr10 | GRID1 | NM_017551 | 88125585 | 88125655 |
| 58 | chr4 | — | — | 180980619 | 180980711 |
| 124 | chr16 | GPT2 | NM_133443; NM_00114246 | 46963785 | 46963821 |
| 125 | chr10 | PIP4K2A | NM_005028 | 23003771 | 23003865 |
| 126 | chr4 | — | — | 184718393 | 184718464 |
| 127 | chr14 | — | — | 103726953 | 103727098 |
| 128 | chr2 | LOC91149 | NR_026995 | 173600924 | 173601006 |
| 33 | chr17 | NGFR | NM_002507 | 47574211 | 47574294 |
| 3 | chr5 | IRX4 | NM_016358 | 1883238 | 1883312 |
| 30 | chr12 | DPY19L2 | NM_173812 | 64061896 | 64062007 |

TABLE 3

Information for DMRs Distinguishing BE from BED

| DMR No. | Chromosome No. | Gene Annotation | Transcript | DMR Start Position | DMR End Position |
|---|---|---|---|---|---|
| 129 | Chr8 | TSPYL5 | | 98289858 | 98290220 |
| 130 | chr12 | ST8SIA1 | | 22487528 | 22487620 |
| 131 | Chr19 | ZNF568 | | 37407197 | 37407365 |
| 132 | chr6 | ELOVL2 | | 11044395 | 11044834 |
| 133 | Chr1 | cd1d | | 158150797 | 158151205 |
| 134 | Chr7 | ELMO1 | | 37487755 | 37488477 |
| 193 | Chr4 | BMP3 | | 81031173 | 81031262 |
| 27 | chr16 | NDRG4 | NM_020465; | 58497251 | 58497332 |

TABLE 3-continued

Information for DMRs Distinguishing BE from BED

| DMR No. | Chromosome No. | Gene Annotation | Transcript | DMR Start Position | DMR End Position |
|---|---|---|---|---|---|
| 101 | Chr9 | CDKN2A | NM_001130487; NM_022910 NM_000077; NM_001195132; NM_058195; NM_058197 | 21974710 | 21974763 |
| 90 | Chr20 | chr20.2188420.2188480 | | 2188420 | 2188480 |
| 77 | chr14 | DIO3 | NM_001362 | 1020261204 | 102026145 |
| 92 | Chr21 | HUNK | NM_014586 | 33246580 | 3326650 |

15

TABLE 4

Primers for DMRs Provided in Table 3.

| DMR No. | Marker | Forward Primer (5'-3') | Reverse Primer (5'-3') |
|---|---|---|---|
| 129 | TSPYL5 | TGG CGG CGG AGG TAG TTT TAA AGA TAC (SEQ ID NO: 1) | TCG ATC CCG ACC GAA AAC TAA CGT C (SEQ ID NO: 2) |
| 130 | ST8SIA1 | GAC GTT TGT CGT CGG GTT CGT TC (SEQ ID NO: 3) | AAA AAC CCT CCG CTA CCA CTT CGC (SEQ ID NO: 4) |
| 131 | ZNF568 | TTG AGA TGT TGG GTG AAG GCG ATT C (SEQ ID NO: 5) | CGC TAA CGC GAA AAA ATA ATT CGA CG (SEQ ID NO: 6) |
| 132 | ELOVL2 | CGGTTTTATTTATTATGAT TCGTAGCGG (SEQ ID NO: 7) | CGACTACCCTAAACAACGC ATCGC (SEQ ID NO: 8) |
| 133 | cd1d | GCG CGT AGC GGC GTT TC (SEQ ID NO: 9) | CCC ATA TCG CCC GAC GTA A (SEQ ID NO: 10) |
| 134 | ELMO1 | TTA TAT TTT TCG TTT TTA GTA ATT TCG CGT TAG C (SEQ ID NO: 11) | GAA AAC CCG CCG AAA CAT TTC GA (SEQ ID NO: 12) |
| 193 | BMP3 | GTTTAATTTTCGGTTTCGT CGTC (SEQ ID NO: 13) | CGCTACGAAACACTCCGA (SEQ ID NO: 14) |
| 27 | NDRG4 | CGGTTTTCGTTCGTTTTTT CG (SEQ ID NO: 15) | CCGCCTTCTACGCGACTA (SEQ ID NO: 16) |
| 101 | CDKN2A | GGGGCGTTGTTTAACGTA TCGAATAGTTAC (SEQ ID NO: 17) | GCTACAAACCCTCTACCCA CCTAAATCGAC (SEQ ID NO: 18) |
| 90 | chr20.2188420. 2188480 | TTTTAGTAAGGGTCGTATT GGACGT (SEQ ID NO: 19) | CAAAAACTCGCTAACACGA AACTCCCG (SEQ ID NO: 20) |
| 77 | D103 | GtTCGtCGttCGGGtC (SEQ ID NO: 21) | TCCTTCGCTaCCGAAAaCG (SEQ ID NO: 22) |
| 92 | HUNK | GttTCGttACGGATtCGtC (SEQ ID NO: 23) | TaCTCGTaaAAaaaCGCCG (SEQ ID NO: 24) |

TABLE 5

Information for DMRs Distinguishing Between LGD, HGD and EAC, and Distinguishing Between BE and BED

| DMR No. | Chromosome No. | Gene Annotation | Transcript | DMR Start Position | DMR End Position |
|---|---|---|---|---|---|
| 135 | Chr16 | NDRG4 | | 58497395 | 58497458 |
| 90 | Chr20 | chr20.2188420.2188480 | | 2188420 | 2188480 |
| 77 | chr14 | DIO3 | NM_001362 | 1020261204 | 102026145 |

TABLE 6

Information for DMRs Distinguishing BE from BED

| DMR No. | Chromosome No. | Gene Annotation | Transcript | DMR Start/End Positions |
|---|---|---|---|---|
| 136 | 14 | VSX2 | NM_182894 | 74724254-74724300 |
| 137 | 9 | ROR2 | NM_004560 | 94712523-94712575 |
| 138 | 9 | ROR2 | NM_004560 | 94712480-94712521 |
| 139 | 1 | ERO1LB | NM_019891 | 236444768-236444845 |
| 140 | 16 | RAB11FIP3 | NM_014700 | 476335-476351 |
| 141 | 15 | HOMER2 | NM_199332; NM_004839; NM_199330; NM_199331 | 83621577-83621602 |
| 142 | 21 | DSCR6 | NM_018962 | 38379205-38379295 |
| 143 | 15 | HOMER2 | NM_199332; NM_004839; NM_199330; NM_199331 | 83621302-83621420 |
| 144 | 4 | C4orf48 | NM_001168243; NM_001141936 | 2043778-2043860 |
| 145 | 6 | OGFRL1 | NM_024576 | 71998477-71998657 |
| 146 | 8 | TOX | NM_014729 | 60031838-60032005 |
| 147 | 2 | SERPINE2 | NM_001136530; NM_006216; NM_001136528 | 224904018-224904069 |
| 148 | 11 | DENND5A | NM_015213 | 9286532-9286607 |
| 149 | 13 | INFRSF19 | NM_018647; NM_148957 | 24153164-24153364 |
| 150 | 13 | INFRSF19 | NM_018647; NM_148957 | 24152949-24153119 |
| 151 | 14 | CIDEB | NM_014430 | 24780120-24780207 |
| 152 | 9 | FBXO10 | NM_012166 | 37576336-37576403 |
| 153 | 13 | ATP12A | NM_001676; NM_001185085 | 25254666-25254800 |
| 154 | 9 | CDKN2A | NM_000077; NM_001195132; NM_058195; NM_058197 | 21975053-21975199 |
| 155 | 10 | STK32C | NM_173575 | 134120900-134120935 |
| 156 | 19 | LRP3 | NM_002333 | 33685030-33685057 |
| 157 | 9 | NCRNA00092 | NR_024129 | 98783837-98783927 |
| 158 | 15 | ARNT2 | NM_014862 | 80697235-80697338 |
| 159 | 15 | ARNT2 | NM_014862 | 80696974-80697085 |
| 160 | 1 | HTR6 | NM_000871 | 19991341-19991374 |
| 161 | 6 | SYNE1 | NM_015293; NM_182961; NM_033071 | 152623220-152623293 |
| 162 | 1 | HTR6 | NM_000871 | 19991278-19991318 |
| 163 | 19 | LRP3 | NM_002333 | 33685156-33685205 |
| 164 | 2 | IGFBP2 | NM_000597 | 217497874-217497957 |
| 165 | 1 | MAX.chr1.244013647-244014036 | — | 244013647-244014036 |
| 166 | 9 | LPAR1 | NM_057159; NM_001401 | 113801112-113801189 |
| 167 | 6 | SYNE1 | NM_015293; NM_182961; NM_033071 | 152623302-152623313 |
| 168 | 5 | MCC | NM_001085377; NM_002387 | 112630385-112630541 |
| 169 | 2 | SLC16A14 | NM_152527 | 230933219-230933384 |
| 170 | 2 | MAX.chr2.11623000-11623066 | — | 11623000-11623066 |
| 171 | 3 | ST3GAL6 | NM_006100 | 98451352-98451466 |
| 172 | 10 | STK32C | NM_173575 | 134120798-134120896 |

TABLE 6-continued

Information for DMRs Distinguishing BE from BED

| DMR No. | Chromosome No. | Gene Annotation | Transcript | DMR Start/End Positions |
|---|---|---|---|---|
| 173 | 10 | NEURL | NM_004210 | 105254137-105254241 |
| 174 | 2 | INHBB | NM_002193 | 121103407-121103512 |
| 175 | 14 | PRIMA1 | NM_178013 | 94255128-94255181 |
| 176 | 3 | ST3GAL6 | NM_006100 | 98451485-98451504 |
| 177 | 16 | MPV17L | NM_173803; NM_001128423 | 15489844-15489897 |
| 178 | 4 | MAX.chr4.184718755-184718789 | — | 184718755-184718789 |
| 179 | 1 | TTLL7 | NM_024686 | 84464797-84464851 |
| 180 | 14 | PRIMA1 | NM_178013 | 94255078-94255084 |
| 181 | 20 | 01001 | NM_033081; NM_001193369; NM_022105; NM_080797; NM_001193370; NM_080796 | 61560714-61560835 |
| 182 | 4 | C4orf31 | NM_024574 | 121992630-121992757 |
| 183 | 16 | IRX3 | NM_024336 | 54320149-54320196 |
| 184 | 19 | LRP3 | NM_002333 | 33685073-33685127 |
| 185 | 11 | PRR5L | NM_001160167; NM_001160168; NM_024841 | 36398162-36398218 |
| 186 | 3 | ST3GAL6 | NM_006100 | 98451114-98451159 |
| 187 | 5 | MAX.chr5.60921709-60921808 | — | 60921709-60921808 |

TABLE 7

Information for DMRs Distinguishing BE from normal tissue

| DMR No. | Chromosome No. | Gene Annotation | DMR Coordinates | Forward MSP Primer (5'-3') | Reverse MSP Primer (5'-3') |
|---|---|---|---|---|---|
| 188 | 7 | adcy1 | 45613877-45614572 | GGT TCG GTT GTC GTA GCG C (SEQ ID NO: 25) | CCG ACC GTA ATC CTC GAC GA (SEQ ID NO: 26) |
| 189 | 7 | LRRC4 | 127671993-127672310 | GTT AAT TTC GCG AGG TAG GCG ACG (SEQ ID NO: 27) | CGT AAT ACA ATA CTC TTA TAT ATT AAC GCC GCT (SEQ ID NO: 28) |
| 190 | 19 | ZNF569 | 37957760-37958046 | TGT GGA ATC GGG GTT TGT GTT CGC (SEQ ID NO: 29) | CCC ACC CAA CAC AAA AAA TCC GAC G (SEQ ID NO: 30) |
| 21 | 19 | ZNF682 | 20149796-20149923 | GGA GTT TAT TTT GGG AAG AGT CGC (SEQ ID NO: 31) | CCC CGC AAT CGA AAC AAA CG (SEQ ID NO: 32) |
| 191 | 14 | PTGDR | 52735290-52735389 | GGG TAG AGA ATA TAT AGT GAA GAG TAC GG (SEQ ID NO: 33) | ACT AAA TCA CCT CCT ACT ACT AAC GCT (SEQ ID NO: 34) |
| 192 | 10 | SFMBT2 | 7452029-7452452 | GCG ACG TAG TCG TCG TTG T (SEQ ID NO: 35) | CCA ACG CGA AAA AAA CGC G (SEQ ID NO: 36) |

Example II

This example describes the materials and methods utilized in generating Tables 1 and 7.

18 Barrett's esophagus (BE) and 18 normal esophagus tissue samples were selected from institutional cancer registries at Mayo Clinic Rochester and were reviewed by an expert pathologist to confirm correct classification. Normal leukocyte controls were provided by the Mayo Biospecimens Linking Investigators and Clinicians to GIH Cell Signaling Research Clinical Core.

Library Preparation: Genomic DNA (300 ng) was fragmented by digestion with 10 Units of MspI, a methylation-specific restriction enzyme which recognizes CpG-containing motifs, to enrich sample CpG content and eliminates redundant areas of the genome. Digested fragments were end-repaired and A-tailed with 5 Units of Klenow fragment (3'-5' exo-), and ligated overnight to methylated TruSeq adapters (Illumina, San Diego CA) containing barcode sequences (to link each fragment to its sample ID.) Size selection of 160-340 bp fragments (40-220 bp inserts) was performed using Agencourt AMPure XP SPRI beads/buffer (Beckman Coulter, Brea CA). Buffer cutoffs were 0.7×-1.1× sample volumes of beads/buffer. Final elution volume was 22 uL (EB buffer—Qiagen, Germantown MD); qPCR was used to gauge ligation efficiency and fragment quality on a small sample aliquot. Samples then underwent bisulfite conversion (twice) using a modified EpiTect protocol (Qiagen). qPCR and conventional PCR (PfuTurbo Cx hotstart—Agilent, Santa Clara CA) followed by Bioanalyzer 2100 (Agilent) assessment on converted sample aliquots determined the optimal PCR cycle number prior to final library amplification. The following conditions were used for final PCR: 1.) each 50 uL reaction contained 5 uL of 10× buffer, 1.25 uL of 10 mM each deoxyribonucleotide triphosphate (dNTP), 5 uL primer cocktail (~5 uM), 15 uL template (sample), 1 uL PfuTurbo Cx hotstart and 22.75 water; temperatures and times were 95 C-5 min; 98 C-30 sec; 16 cycles of 98 C-10 sec, 65 C-30 sec, 72 C-30 sec, 72 C-5 min and 4 C hold, respectively. Samples were combined (equimolar) into 4-plex libraries based on the randomization scheme and tested with the bioanalyzer for final size verification, and with qPCR using phiX standards and adaptor-specific primers.

Sequencing and Bioinformatics: Samples were loaded onto flow cells according to a randomized lane assignment with additional lanes reserved for internal assay controls. Sequencing was performed by the Next Generation Sequencing Core at the Mayo Clinic Medical Genome Facility on the Illumina HiSeq 2000. Reads were unidirectional for 101 cycles. Each flow cell lane generated 100-120 million reads, sufficient for a median coverage of 30-50 fold sequencing depth (read number per CpG) for aligned sequences. Standard Illumina pipeline software called bases and sequenced read generation in the fastq format. As described previously, (28) SAAP-RRBS, a streamlined analysis and annotation pipeline for reduced representation bisulfite sequencing, was used for sequence alignment and methylation extraction.

MSP Primer design: Primers for 6 top markers from the sequencing results were designed and ordered (IDT, Coralville IA) to target specific bisulfite-modified methylated sequences (table 7). The designs were done by either Methprimer software (University of California, San Francisco CA) or MSPPrimer (Johns Hopkins University, Baltimore, MD). Assays were tested and optimized by qPCR with SYBR Green on dilutions of universally methylated and unmethylated genomic DNA controls.

Methylation specific PCR: Quantitative MSP reactions were performed on independent tissue-extracted DNA: 108 BE samples—36 with high grade dysplasia, 36 with low grade dysplasia, and 36 with no dysplasia, 18 normal esophagus samples, and 36 normal leukocyte samples.

Statistical Analysis: Candidate CpGs were filtered by a priori read-depth and variance criteria, significance of differential %-methylation percentages between cases and controls and discrimination of cases from controls based on area under the receiver operating characteristics curve (AUC) and target to background ratio.

For the RRBS discovery phase, the primary comparison of interest was the methylation difference between Barrett's cases, esophagus controls and leukocyte controls at each mapped CpG. CpG islands are biochemically defined by an observed to expected CpG ratio >0.6.(30) However, for this model, tiled units of CpG analysis "differentially methylated region (DMR)" were created based on distance between CpG site locations for each chromosome. Islands with only single CpGs were excluded. Individual CpG sites were considered for differential analysis only if the total depth of coverage per disease group was ≥200 reads (an average of 10 reads/subject) and the variance of %-methylation was >0 (non-informative CpGs were excluded). Read-depth criteria were based on the desired statistical power to detect a 10% difference in the %-methylation between any two groups in which the sample size of each group was 18 individuals. Statistical significance was determined by logistic regression of the methylation percentage per DMR, based on read counts. To account for varying read depths across individual subjects, an over-dispersed logistic regression model was used, where dispersion parameter was estimated using the Pearson Chi-square statistic of the residuals from fitted model. DMRs, ranked according to their significance level, were further considered if %-methylation in benign esophagus and leukocyte controls, combined, was ≤1% but ≥10% in Barrett's cases. This resulted in 78 markers (Table 1). All had AUCs greater than 0.90 and fold changes greater than 25.

For the 6 marker qMSP validation study (Table 7), the primary outcome was the area under the receiver operating characteristics curve (AUC) for each marker, as calculated from logistic regression models of the % methylated copy number per sample with BE in comparison to normal esophagus and normal leukocytes. For each marker, AUCs were again >0.90 and the quantitative difference in mean values of candidate genomic copy number per sample between cases and controls were at least 50-fold.

Example III

This example describes the materials and methods utilized in generating Tables 2 and 6.

36 Barrett's esophagus with high and low dysplasia (BED) and 18 Barrett's esophagus with no dysplasia (BE) tissue samples were selected from institutional cancer registries at Mayo Clinic Rochester and were reviewed by an expert pathologist to confirm correct classification. 18 Normal leukocyte controls were provided by the Mayo Biospecimens Linking Investigators and Clinicians to GIH Cell Signaling Research Clinical Core.

Library Preparation: Genomic DNA (300 ng) was fragmented by digestion with 10 Units of MspI, a methylation-specific restriction enzyme which recognizes CpG-containing motifs, to enrich sample CpG content and eliminates redundant areas of the genome. Digested fragments were end-repaired and A-tailed with 5 Units of Klenow fragment (3'-5' exo-), and ligated overnight to methylated TruSeq adapters (Illumina, San Diego CA) containing barcode sequences (to link each fragment to its sample ID.) Size selection of 160-340 bp fragments (40-220 bp inserts) was performed using Agencourt AMPure XP SPRI beads/buffer (Beckman Coulter, Brea CA). Buffer cutoffs were 0.7×-1.1× sample volumes of beads/buffer. Final elution volume was 22 uL (EB buffer—Qiagen, Germantown MD); qPCR was used to gauge ligation efficiency and fragment quality on a small sample aliquot. Samples then underwent bisulfite conversion (twice) using a modified EpiTect protocol (Qiagen). qPCR and conventional PCR (PfuTurbo Cx hotstart—Agilent, Santa Clara CA) followed by Bioanalyzer 2100 (Agilent) assessment on converted sample aliquots determined the optimal PCR cycle number prior to final library amplification. The following conditions were used for final PCR: 1.) each 50 uL reaction contained 5 uL of 10× buffer, 1.25 uL of 10 mM each deoxyribonucleotide triphosphate (dNTP), 5 uL primer cocktail (~5 uM), 15 uL template (sample), 1 uL PfuTurbo Cx hotstart and 22.75 water; temperatures and times were 95 C-5 min; 98 C-30 sec; 16 cycles of 98 C-10 sec, 65 C-30 sec, 72 C-30 sec, 72 C-5 min and 4 C hold, respectively. Samples were combined (equimolar) into 4-plex libraries based on the randomization scheme and tested with the bioanalyzer for final size verification, and with qPCR using phiX standards and adaptor-specific primers.

Sequencing and Bioinformatics: Samples were loaded onto flow cells according to a randomized lane assignment with additional lanes reserved for internal assay controls. Sequencing was performed by the Next Generation Sequencing Core at the Mayo Clinic Medical Genome Facility on the Illumina HiSeq 2000. Reads were unidirectional for 101 cycles. Each flow cell lane generated 100-120 million reads, sufficient for a median coverage of 30-50 fold sequencing depth (read number per CpG) for aligned sequences. Standard Illumina pipeline software called bases and sequenced read generation in the fastq format. As described previously, (28) SAAP-RRBS, a streamlined analysis and annotation pipeline for reduced representation bisulfite sequencing, was used for sequence alignment and methylation extraction.

MSP Primer design: Primers for the top 66 markers from the sequencing results were designed and ordered (IDT, Coralville Iowa) to target specific bisulfite-modified methylated sequences (table 7). The designs were done by either Methprimer software (University of California, San Francisco CA) or MSPPrimer (Johns Hopkins University, Baltimore, MD). Assays were tested and optimized by qPCR with SYBR Green on dilutions of universally methylated and unmethylated genomic DNA controls.

Methylation specific PCR: Quantitative MSP reactions were performed on independent tissue-extracted DNA: 108 BE samples—36 with high grade dysplasia, 36 with low grade dysplasia, and 36 with no dysplasia, 18 normal esophagus samples, and 36 normal leukocyte samples.

Statistical Analysis: Candidate CpGs were filtered by a priori read-depth and variance criteria, significance of differential %-methylation percentages between cases and controls and discrimination of cases from controls based on area under the receiver operating characteristics curve (AUC) and target to background ratio.

For the RRBS discovery phase, the primary comparison of interest was the methylation difference between Barrett's cases with high and low grade dysplasia, Barrett's with no dysplasia controls, and leukocyte controls at each mapped CpG. CpG islands are biochemically defined by an observed to expected CpG ratio >0.6.(30) However, for this model, tiled units of CpG analysis "differentially methylated region (DMR)" were created based on distance between CpG site locations for each chromosome. Islands with only single CpGs were excluded. Individual CpG sites were considered for differential analysis only if the total depth of coverage per disease group was ≥200 reads (an average of 10 reads/subject) and the variance of %-methylation was >0 (non-informative CpGs were excluded). Read-depth criteria were based on the desired statistical power to detect a 10% difference in the %-methylation between any two groups in which the sample size of each group was 18 individuals. Statistical significance was determined by logistic regression of the methylation percentage per DMR, based on read counts. To account for varying read depths across individual subjects, an over-dispersed logistic regression model was used, where dispersion parameter was estimated using the Pearson Chi-square statistic of the residuals from fitted model. DMRs, ranked according to their significance level, were further considered if %-methylation in benign esophagus and leukocyte controls, combined, was ≤1% but ≥10% in Barrett's cases. This resulted in 57 markers (Table 2). All had AUCs between 0.60 and 0.87 and fold changes between 2 and 10. A second sorting of the data was performed, loosening the island restriction metrics and focusing on groupings of highly discriminate single CpGs. A batch to batch effect on the leukocyte controls was also removed which increased the overall coverage. This resulted in 52 additional markers with increased fold changes (7-52) and similar AUCs (Table 6).

For the 66 DMR qMSP validation study, the primary outcome was the area under the receiver operating characteristics curve (AUC) for each marker, as calculated from logistic regression models of the % methylated copy number per sample with BED in comparison to BE and normal leukocytes. 12 markers demonstrated superior performance (Table 3). AUCs were 0.86-0.97 and fold changes 2-24. 10 of the 12 markers, along with BMP3 and NDRG4, were carried into the esophageal brushing feasibility study.

Example IV

This example describes the materials and methods utilized in generating Tables 3, 4 and 5.

Consenting BE subjects scheduled for endoscopic BE surveillance or endoscopic assessment of BE related cancers underwent whole esophageal brushings using a high capacity cytology brush (Hobbs Medical, Stafford Springs, CT) with circumferential sampling from the cardia through the full esophageal length (BE+squamous mucosa). The cytology brush was removed from the handle and placed into a vial of stability/cell lysis solution and frozen until processing. DNA was extracted using the Gentra Puregene Buccal procedure (Qiagen, Valencia, CA). 2 ug of DNA from each patient sample was treated with sodium bisulfite and purified using the EZ DNA Methylation kit (Zymo Research, Irvine, CA). MSP was performed using 20 ng of converted DNA on the 10 of the 12 validated DMRs from the BED vs. BE study (Table 3). The primer sequences are highlighted in Table 4. In addition the BMP3 and NDRG4 Cologuard QuARTs assays were run. The method of DeLong, DeLong and Clarke-Pearson was used to compare AUCs and measure significance of differences. A Bonferroni correction was used to avoid bias from multiple comparisons. The 3 markers which (in combination) demonstrated the highest discrimination for BED vs. BE are listed in Table 5.

Example V

This example demonstrates the discovery, validation and feasibility testing of methylated DNA markers for detection of Barrett's Esophagus.

Phase 1 Methods and Results:

Pathologist verified FFPE tissues were provided by the Mayo Clinic Tissue Registry. Clinical groups consisted of patients with Barrett's HGD (N=34), Barrett's LGD (N=34), Barrett's no dysplasia (N=34), esophageal adenocarcinomas (N=12), esophageal squamous cell carcinomas (N=12), normal cardia (N=13), normal esophagus (N=25). DNA was purified using the Qiagen Mini kit and quantified by absorbance and picogreen analysis. Bisulfite conversion was performed using the Zymo method. Methylation markers consisted of top candidates from 3 categories of RRBS subsets: 1) 45 BED vs. BE DMRs (differentially methylated regions), 2) 5 BE vs. normal esophagus DMRs, and 3) 33 previously validated esophageal cancer markers. (Note: All of these DMRs were previously filtered against normal leukocytes for <1% background methylation.) Methylation specific PCR (MSP) primers were designed for each of these genomic regions and tested on 3 sets of methylation controls for performance. Table 8 provides DMR information including chromosome number, gene annotation, and DMR start/stop position for such markers identified to separate BE from normal tissue. QMSP (SYBR Green) was performed using Roche 480 LightCyclers. Serially diluted universal methylated DNA was used as a standard. In addition, QuARTs assays were run on the markers BMP3, NDRG4, SFMBT2, and VAV3. These latter 4 include 2 reference genes β-actin and ZDHHC1 in their triplex assay formats.

Results were normalized against β-actin and ZDHHC1 and analyzed logistically in JMP. Areas under the ROC curve (AUC) were calculated along with fold changes and p-values. Performance cut-offs for phase 2 were AUC≥0.95, fold change ≥25, and p-value ≤0.1. 13 markers passed these criteria: CDKN2A, SFMBT2, VAV3, DIO3, ELMO1, FEM1B, HUNK, ADCY1, CD1D, ST3GAL6, LRRC4, NDRG4, and BMP3 (Table 9 provides the identity and primer sequences for these assays including OPLAH).

TABLE 8

Information for DMRs distinguishing BE and normal tissue

| DMR No. | Gene Annotation | Chromosome No. | DMR Start and End Position |
|---|---|---|---|
| 2 | ZNF568 | 19 | 37407197-37407284 |
| 3 | IRX4 | 5 | 1883238-1883312 |
| 4 | RGS17 | 6 | 153451813-153451881 |
| 6 | EPHA5 | 4 | 66536122-66536220 |
| 7 | SFMBT2.1869 | 10 | 7451771-7451869 |
| 14 | A1BG | 19 | 58859193-58859258 |
| 30 | DPY19L2 | 12 | 64061896-64062007 |
| 77 | DIO3 | 14 | 102026104-102026145 |
| 80 | WNT2 | 7 | 116964596-116964659 |
| 82 | RGL3 | 19 | 11529371-11529430 |
| 83 | FEM1B | 15 | 68569729-68569799 |
| 84 | ARNT2 | 1S | 80696170-80696177 |
| 85 | LARP6 | 15 | 71146759-71146820 |
| 86 | ZC3HAV1L | 7 | 138720915-138720957 |
| 88 | Max.chr15.41877531.41877548 | 15 | 41877531-41877548 |
| 90 | Max.chr20.2188420.2188480 | 20 | 2188420-2188480 |
| 91 | KLHL14 | 18 | 30351268-30351486 |
| 92 | HUNK | 21 | 33246580-33246650 |
| 93 | LOC100131691 | 19 | 59073783-59073952 |
| 94 | Max.chr13.95620964.95621061 | 13 | 95620964-95621061 |
| 95 | Max.chr5.926920.927009 | 5 | 926920-927009 |
| 96 | C6orf114 | 6 | 13488436-13488530 |
| 97 | ARHGEF10 | 8 | 1771362-1771477 |
| 98 | VSTM2L | 20 | 36531194-36531312 |
| 99 | ACAD11 | 3 | 132378234-132378296 |
| 100 | WSB2 | 12 | 118500206-118500305 |
| 101 | CDKN2A | 9 | 21974710-21974763 |
| 102 | Max.chr6.27064706.27064783 | 6 | 27064706-27064783 |
| 108 | WIF1 | 12 | 65514995-65515089 |
| 122 | DLX5 | 7 | 96653893-96653955 |
| 135 | NDRG4 | 16 | 58497395-58497451 |
| 136 | VSX2 | 14 | 74724254-74724300 |
| 141 | HOMER2 | 15 | 83621577-83621602 |
| 142 | DSCR6 | 21 | 38379205-38379295 |
| 144 | C4orf48 | 4 | 2043778-2043860 |
| 146 | TOX | 8 | 60031838-60032005 |
| 148 | DENND5A | 11 | 9286532-9286607 |
| 149 | INFRSF19 | 13 | 24153164-24153364 |
| 152 | FBXO10 | 9 | 37576336-37576403 |
| 154 | CDKN2A | 9 | 21975053-21975199 |
| 156 | LRP3 | 19 | 33685030-33685057 |
| 164 | IGFBP2 | 2 | 217497874-217497957 |
| 166 | LPAR1 | 9 | 113801112-113801189 |
| 171 | ST3GAL6 | 3 | 98451352-98451466 |
| 173 | NEURL | 10 | 105254137-105254241 |
| 175 | PRIMA1 | 14 | 94255128-94255181 |
| 178 | MAX.chr4.184718755-184718789 | 4 | 184718755-184718789 |
| 179 | TTLL7 | 1 | 84464797-84464851 |
| 181 | DIDO1 | 20 | 61560714-61560835 |
| 185 | PRR5L | 11 | 36398162-36398218 |
| 187 | MAX.chr5.60921709-60921808 | 5 | 60921709-60921808 |
| 193 | BMP3 | 4 | 81952348-81952402 |
| 194 | VAV3 | 1 | 108507608-108507679 |
| 195 | CYP26C1.F | 10 | 94822416-94822607 |
| 196 | EMX1.F | 2 | 73147710-73147772 |
| 197 | LOC645323.R | 7 | 25896389-25896501 |
| 198 | ELOVL2.F | 6 | 11044395-11044834 |
| 199 | FLI1.F | 11 | 128563956-128564209 |

TABLE 8-continued

Information for DMRs distinguishing BE and normal tissue

| DMR No. | Gene Annotation | Chromosome No. | DMR Start and End Position |
|---|---|---|---|
| 200 | KCNK12 | 2 | 47797187-47797452 |
| 201 | SFMBT2.893 | 10 | 7450242-7450831 |
| 202 | SFMBT2.895 | 10 | 7452029-7452452 |
| 203 | ZNF625.F | 19 | 12267378-12267677 |
| 204 | ELMO1.F | 7 | 37487755-37488477 |
| 205 | ST8SIA1.F | 12 | 22487528-22487620 |
| 206 | ZNF568.R | 19 | 37407197-37407365 |
| 207 | GRIN2D.R | 19 | 48918144-48918350 |
| 208 | TBX15.F | 1 | 119527066-119527655 |
| 209 | TSPYL5.F | 8 | 98289858-98290220 |
| 210 | ZNF610.R | 19 | 52839503-52840013 |
| 211 | ZNF671.F | 19 | 58238810-58238955 |
| 212 | ZNF781.F | 19 | 38182950-38183127 |
| 213 | ADCY11 | 7 | 45613877-45614572 |
| 214 | C13orf18 | 13 | 46960767-46961669 |
| 215 | CD1D | 1 | 158150797-158151205 |
| 216 | AK055957 (chr12.133) | 12 | 133484978-133485739 |
| 217 | CLEC11A | 19 | 51228217-51228732 |
| 218 | RSPO3 | 6 | 127440492-127441039 |
| 219 | TOX2 | 20 | 42544780-42544835 |
| 220 | VWC2 | 7 | 49813135-49814168 |
| 221 | DOCK10.F | 2 | 225907226-225907322 |
| 222 | LRRC4.R | 7 | 127671993-127672310 |
| 223 | MAX.chr11.123301058.123301255.R | 11 | 123301058-123301255 |
| 224 | STC.ZNF569.R | 19 | 37957760-37958046 |
| 225 | ZNF682.R | 19 | 20149796-20149923 |
| 226 | GRM8.F | 7 | 126891703-126892479 |
| 227 | PTGDR.R | 14 | 52735290-52735389 |
| 228 | OPLAH | 8 | 145106349-145106456 |
| 229 | SFMBT2 | 10 | 7452885-7452956 |

TABLE 9

Primers for specific DMRs Provided Described in Example V.

| DMR No. | Marker | Forward Primer (5'-3') | Reverse Primer (5'-3') | Probe |
|---|---|---|---|---|
| 204 | ELMO1.F | TTA TAT TTT TCG TTT TTA GTA ATT TCG CGT TAG C (SEQ ID NO: 11) | GAA AAC CCG CCG AAA CAT TTC GA (SEQ ID NO: 12) | |
| 213 | ADCY1 | GGT TCG GTT GTC GTA GCG C (SEQ ID NO: 25) | CCG ACC GTA ATC CTC GAC GA (SEQ ID NO: 26) | |
| 215 | CD1D | GCG CGT AGC GGC GTT TC (SEQ ID NO: 9) | CCC ATA TCG CCC GAC GTA A (SEQ ID NO: 10) | |
| 222 | LRRC4.R | GTT AAT TTC GCG AGG TAG GCG ACG (SEQ ID NO: 27) | CGT AAT ACA ATA CTC TTA TAT ATT AAC GCC GCT (SEQ ID NO: 28) | |
| 228 | OPLAH | TGC GTA GGT GAT AGG GAG GGT TTA C (SEQ ID NO: 47) | ACA AAA CAC ATC CTA TTA ACG CGA A (SEQ ID NO: 48) | |
| 101 | CDKN2A | GGGGCGTTGTTTAA CGTATCGAATAGTTA C (SEQ ID NO: 17) | GCTACAAACCCTCT ACCCACCTAAATCG AC (SEQ ID NO: 18) | |
| 77 | DIO3 | GtTCGtCGttCGGGtC (SEQ ID NO: 21) | TCCTTCGCTaCCGA AAaCG (SEQ ID NO: 22) | |
| 83 | FEM1B | tTttAtATTTCGGGAAt TtAGAAACGtC (SEQ ID NO: 49) | TaAaCCGaaaTTAaaa AAaaaaTTaCGCG (SEQ ID NO: 50) | |

TABLE 9-continued

Primers for specific DMRs Provided Described in Example V.

| DMR No. | Marker | Forward Primer (5'-3') | Reverse Primer (5'-3') | Probe |
|---|---|---|---|---|
| 92 | HUNK | GttTCGttACGGATtCGtC (SEQ ID NO: 23) | TaCTCGTaaAAaaaCGCC (SEQ ID NO: 24) | |
| 171 | ST3GAL6 | GTTTCGTTCGAAAGGTAGGGGTTCG (SEQ ID NO: 37) | CGAATCTCCCGAAAAATAAAACGTT (SEQ ID NO: 38) | |
| 193 | BMP3 | GTTTAATTTTCGGTTTCGTCGTC (SEQ ID NO: 13) | CGCTACGAAACACTCCGA (SEQ ID NO: 14) | CGCCGAGGCGGTTTTTTGCG (SEQ ID NO: 43) |
| 135 | NDRG4 | CGGTTTTCGTTCGTTTTTTCG (SEQ ID NO: 15) | CCGCCTTCTACGCGACTA (SEQ ID NO: 16) | CCACGGACGGTTCGTTTATCG (SEQ ID NO: 44) |
| 194 | VAV3 | TCGGAGTCGAGTTTAGCGC (SEQ ID NO: 39) | CGAAATCGAAAAACAAAAACCGC (SEQ ID NO: 40) | CGCCGAGGCGGCGTTCGCGA (SEQ ID NO: 45) |
| 229 | SFMBT2 | GTCGTCGTTCGAGAGGGTA (SEQ ID NO: 41) | CGAACAAAAACGAACGAACGAA (SEQ ID NO: 42) | CCACGGACGATCGGTTTCGTT (SEQ ID NO: 46) |

Phase 2 Methods and Results:

49 cases with and 36 controls without BE were recruited prior to endoscopy. Median age was 69 (range 63-73) and 59 (45-67) and men comprised 92% and 42%, respectively. BE cases had >1 cm (median=2 cm; IQR 4-8) of circumferential columnar mucosa with confirmed intestinal metaplasia; controls had no BE endoscopically. Specimens were obtained using a high capacity endoscopic cytology brush (Hobbs Medical, Stafford Springs CT); the cardia, BE (in cases), and full esophageal length were brushed to simulate a swallowed sponge sampling device. The brush was placed in a 2 ml vial containing lysis buffer and promptly frozen at −80 C. Samples were thawed and processed as a batch in blinded fashion. Following vigorous vortexing of the vial to remove all cellular material from the brush, DNA was purified using the Gentra Puregene kit (Qiagen). This method allows for the simultaneous harvesting of both free and cellular DNA. Samples were then treated with sodium bisulfite and recovered using the EZ DNA methylation kit (Zymo Research).

Figure 2:
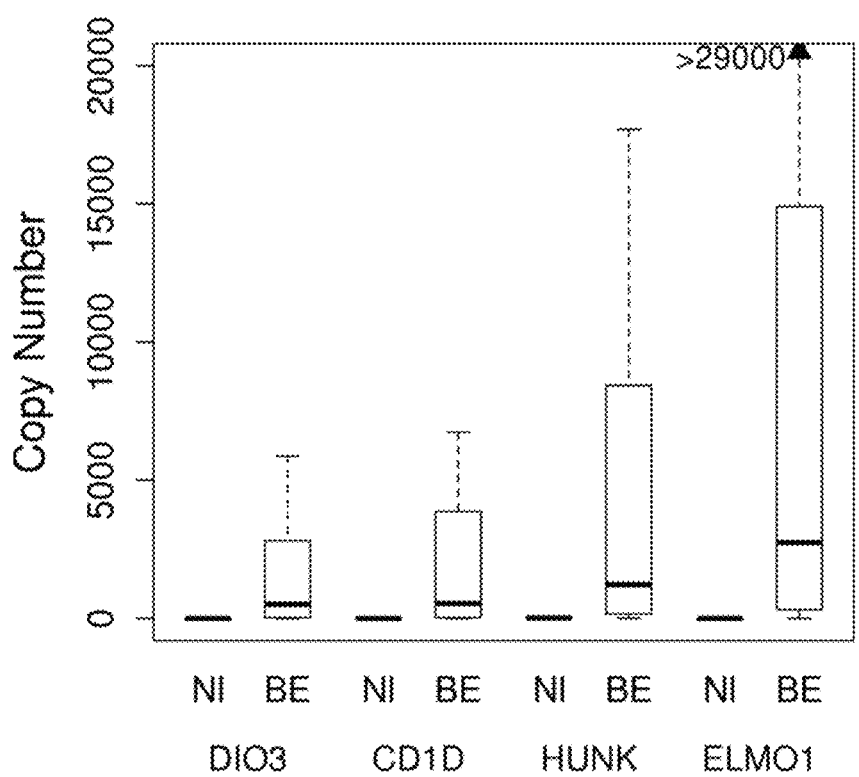
FIG. 2: Methylated DNA marker levels (PCR copies/20 ng DNA) in BE cases and normal (Nl) controls from Phase 2 (endoscopic brush study) (Example V).
Figure 3:
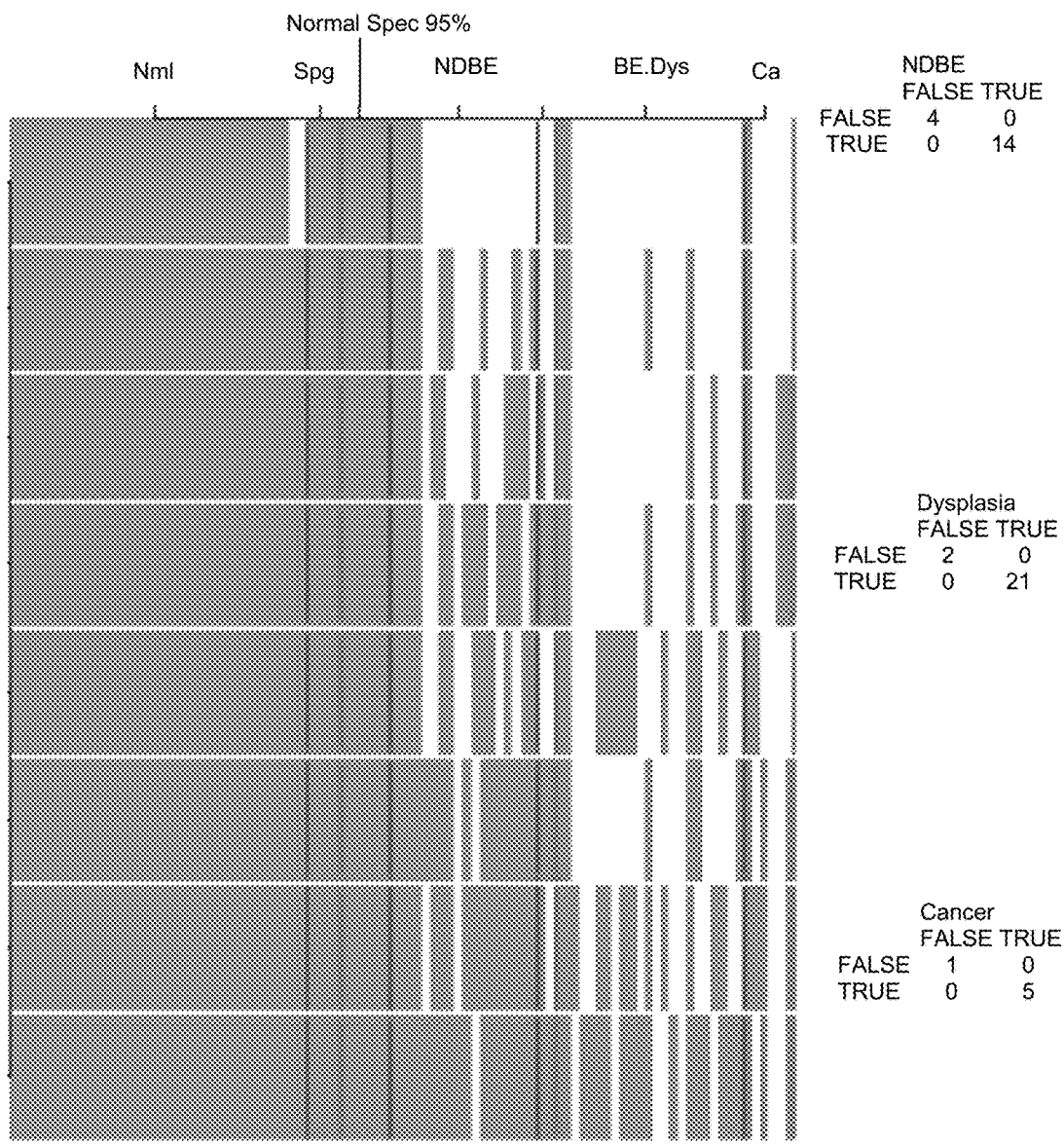
FIG. 3: Hit Matrix of Top Methylated DNA markers from Phase 2 highlighting complementarity (endoscopic brush study) (Example V).

Methylation of the 13 target genes was assayed by QMSP and QuARTs as before on Roche 480 LightCyclers. β-actin and ZDHHC1 were also quantified as markers for total human DNA. Several markers (e.g. BMP3, CDKN2A, CD1D, HUNK, ELMO1, DIO3) showed exceptional discrimination for BE with AUCs 0.91-0.97; methylation level distributions from BE cases and controls differed substantially (FIG. 2). Methylation levels correlated with BE length and presence of dysplasia, p<0.05. FIG. 3 shows a hit matrix of top methylated DNA markers from Phase 2 highlighting complementarity (endoscopic brush study).

10 Barrett's specific markers were chosen for phase 3 testing: BMP3, NDRG4, VAV3, SFMBT2, D103, HUNK, ELMO1, CD1D, CDKN2A, and OPLAH. OPLAH was not included in the earlier phases, but was added here due to its excellent performance in discriminating esophageal cancers from normal tissue.

Phase 3 Methods and Results:

A capsule sponge device (EsophaCap, Capnostics) was swallowed and withdrawn in 10 cases with BE and 12 controls without apparent BE followed by endoscopy within 24 hours. Among 10 cases and 12 controls, median age was 65 (59-69) and 40 (34-61) and men comprised 70% and 45%, respectively. Median BE length was 4.5 cm (IQR 2-9). The device was then placed in a vial containing 20 mL of cell preservation buffer (PreservCyt). Samples were vortexed and transferred into a 50 mL centrifuge tube. This step was repeated with an additional aliquot of PreservCyt for a total of 40 ml. The cells were pelleted and lysed in 1 mL of buffer (Puregene Buccal Cell Kit) and extracted following the manufacturer's directions. A second extraction method (Maxwell-Promega) was also tested. Following bisulfite conversion (Zymo Research), the samples were assayed by QPCR as before. Distributions of top markers from the sponge were highly discriminant for BE. At 100% specificity, a panel of markers detected all 9 BE cases (1 did not meet inclusion criteria) meeting inclusion criteria (100% sensitivity).

Figure 4:
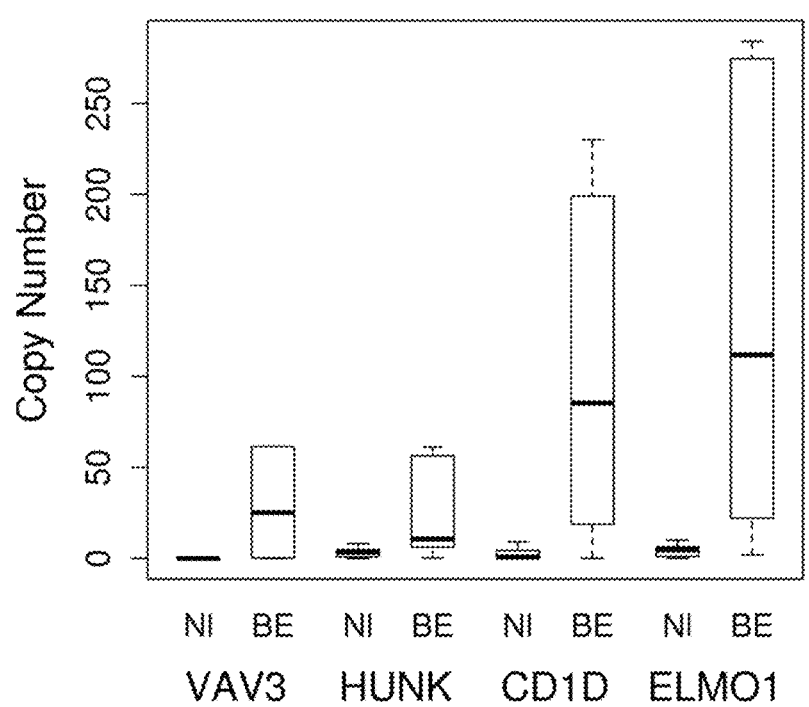
FIG. 4: Methylated DNA marker levels (PCR copies/30 ng DNA) in BE cases and normal (Nl) controls from Phase 3 (capsule sponge study) (Example V).

FIG. 4 shows methylated DNA marker levels (PCR copies/30 ng DNA) in BE cases and normal (Nl) controls from Phase 3 (capsule sponge study).

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A method comprising:
   extracting genomic DNA from a biological sample from a human individual suspected of having or having an esophageal disorder,
   treating the extracted genomic DNA with bisulfite,
   amplifying the bisulfite-treated genomic DNA using primers specific for each of ten or fewer markers, and
   measuring a methylation level of at least one differentially methylated region (DMR) in each of the ten or fewer markers using methylation-specific PCR, quantitative methylation-specific PCR, methylation-sensitive DNA restriction enzyme analysis, or bisulfite genomic sequencing PCR,
   wherein the ten or fewer markers comprise VAV3.

2. The method of claim 1, wherein the ten or fewer markers comprise one or both of NDRG4 and ZNF682.

3. The method of claim 2, wherein the primers specific for NDRG4 are capable of binding an amplicon bound by a sequence comprising SEQ ID NOs: 15 and 16.

4. The method of claim 2, wherein the primers specific for NDRG4 comprise SEQ ID NOs: 15 and 16.

5. The method of claim 2, wherein the primers specific for ZNF682 are capable of binding an amplicon bound by a sequence comprising SEQ ID NOs: 31 and 32.

6. The method of claim 2, wherein the primers specific for ZNF682 comprise SEQ ID NOs: 31 and 32.

7. The method of claim 1, wherein the biological sample comprises cells, tissues, and/or secretions from the upper gastrointestinal tract and/or the lower gastrointestinal tract.

8. The method of claim 1, wherein the biological sample is a stool sample, a tissue sample, a blood sample, or a urine sample.

9. The method of claim 8, wherein the tissue sample comprise esophageal tissue.

10. The method of claim 1, wherein the esophageal disorder is Barrett's esophagus (BE).

11. The method of claim 10, wherein the methylation level of the at least one DMR in each of the ten or fewer markers distinguishes BE from normal tissue.

12. The method of claim 1, wherein the primers specific for VAV3 are capable of binding an amplicon bound by a sequence comprising SEQ ID NOs: 39 and 40.

13. The method of claim 1, wherein the primers specific for VAV3 comprise SEQ ID NOs: 39 and 40.

14. The method of claim 1, wherein the ten or fewer markers comprise BMP3, SFMBT2, DIO3, HUNK, ELMO1, CD1D, CDKN2A, and/or OPLAH.

* * * * *